US008747845B2

(12) United States Patent
Wong et al.

(10) Patent No.: US 8,747,845 B2
(45) Date of Patent: Jun. 10, 2014

(54) METHODS OF TREATMENT BY ADMINISTERING ANTIBODIES THAT BIND COLONY STIMULATING FACTOR 1 RECEPTOR (CSF1R)

(75) Inventors: Justin Wong, Oakland, CA (US); Maximiliano Vasquez, Palo Alto, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 131 days.

(21) Appl. No.: 13/464,503

(22) Filed: May 4, 2012

(65) Prior Publication Data

US 2012/0219524 A1    Aug. 30, 2012

Related U.S. Application Data

(62) Division of application No. 13/100,990, filed on May 4, 2011, now Pat. No. 8,206,715.

(60) Provisional application No. 61/331,177, filed on May 4, 2010.

(51) Int. Cl.
*A61K 39/395* (2006.01)
*A61K 39/00* (2006.01)

(52) U.S. Cl.
USPC ............... 424/130.1; 424/133.1; 424/135.1

(58) Field of Classification Search
None
See application file for complete search history.

(56) References Cited

U.S. PATENT DOCUMENTS

| | | | |
|---|---|---|---|
| 5,866,114 | A | 2/1999 | Pandit et al. |
| 6,184,354 | B1 | 2/2001 | Koths et al. |
| 7,108,852 | B2 | 9/2006 | Devalaraja et al. |
| 7,247,618 | B2 | 7/2007 | Rajavashisth |
| 7,455,836 | B2 | 11/2008 | Hamilton et al. |
| 7,807,389 | B2 | 10/2010 | Ritchlin et al. |
| 7,919,594 | B2 | 4/2011 | Smith et al. |
| 8,206,715 | B2 | 6/2012 | Wong et al. |
| 8,513,199 | B2 | 8/2013 | Brasel et al. |
| 2002/0119494 | A1 | 8/2002 | Jung et al. |
| 2002/0193575 | A1 | 12/2002 | Holmes et al. |
| 2003/0103976 | A1 | 6/2003 | Serizawa et al. |
| 2006/0286102 | A1 | 12/2006 | Jin et al. |
| 2007/0072797 | A1 | 3/2007 | Robinson et al. |
| 2007/0148172 | A1 | 6/2007 | Lawson et al. |
| 2007/0166788 | A1 | 7/2007 | Jin et al. |
| 2008/0219971 | A1 | 9/2008 | Smith et al. |
| 2009/0148883 | A1 | 6/2009 | Manthey |
| 2009/0155164 | A1 | 6/2009 | Brasel et al. |
| 2010/0136006 | A1 | 6/2010 | Lin et al. |
| 2010/0136007 | A1 | 6/2010 | Lin et al. |
| 2011/0243947 | A1 | 10/2011 | Doody et al. |
| 2013/0302322 | A1 | 11/2013 | Wong et al. |

FOREIGN PATENT DOCUMENTS

| | | |
|---|---|---|
| CA | 2388298 | 5/2001 |
| EP | 2241333 A1 | 10/2010 |
| WO | WO 89/03687 | 5/1989 |
| WO | WO 99/29345 | 6/1999 |
| WO | WO 01/34177 | 5/2001 |
| WO | WO 2002/102972 | 12/2002 |
| WO | WO 2004/045532 | 6/2004 |
| WO | WO 2005/070447 | 8/2005 |
| WO | WO 2006/012451 | 2/2006 |
| WO | WO 2007/075933 | 7/2007 |
| WO | WO 2007/081879 | 7/2007 |
| WO | WO 2007/120252 | 10/2007 |
| WO | WO 2008/060610 | 5/2008 |
| WO | WO 2008/124858 | 10/2008 |
| WO | WO 2008/150383 | 12/2008 |
| WO | WO 2009/026303 | 2/2009 |
| WO | WO 2009/058968 | 5/2009 |
| WO | 2009075344 | 6/2009 |
| WO | WO 2009/112245 | 9/2009 |
| WO | WO 2010/062399 | 6/2010 |
| WO | WO 2010/062401 | 6/2010 |
| WO | WO 2011/070024 | 6/2011 |
| WO | WO 2011/107553 | 9/2011 |
| WO | WO 2011/131407 | 10/2011 |
| WO | 2011140249 | 11/2011 |
| WO | 2012082573 | 6/2012 |
| WO | WO 2012/110360 | 8/2012 |
| WO | 2013057281 | 4/2013 |
| WO | 2013057290 | 4/2013 |

OTHER PUBLICATIONS

Bloom et al., Colony stimulating factor-1 in the induction of lupus nephritis, Kidney International, 1993, 43:1000-1009.
Carayannopoulos & Capra, Immunoglobulins: Structure and Function, Fundamental Immunology, 3rd Edition, Paul ed., Raven Press, NY, 1993, 292-295.
Chara et al., Monocyte populations as markers of response to adalimumab plus MTX in rheumatoid arthritis, Arthritis Research & Therapy, 2012, 14:R175 including supplemental data, 13 pages.
Chemel et al., Interleukin 34 expression is associated with synovitis severity in rheumatoid arthritis patients, Ann Rheum Dis, 2012, 71(4150-154.
Colman, Effects of amino acid sequence changes on antibody-antigen interactions, Research in Immunology, 1994, 145:33-36.
Cooper et al., FcεRIIIa Expression on Monocytes in Rheumatoid Arthritis: Role in Immune-Complex Stimulated TNF Production and Non-Response to Methotrexate Therapy, PLoS One, 2012, 7(1):e28918, 10 pages.
Cros et al., Human CD14dim Monocytes Patrol and Sense Nucleic Acids and Viruses via TLR7 and TLR8 Receptors, Immunity, 2010, 33:375-386.

(Continued)

*Primary Examiner* — Robert Landsman
(74) *Attorney, Agent, or Firm* — Casimir Jones S.C.

(57) ABSTRACT

Antibodies that bind CSF1R are provided. Antibody heavy chains and light chains that are capable of forming antibodies that bind CSF1R are also provided. Polynucleotides encoding antibodies to CSF1R are provided. Polynucleotides encoding antibody heavy chains and lights chains are also provided. Methods of treatment using antibodies to CSF1R are provided. Such methods include, but are not limited to, methods of treating rheumatoid arthritis, bone loss, and multiple sclerosis.

13 Claims, 16 Drawing Sheets

(56) References Cited

OTHER PUBLICATIONS

Garcia et al., Colony-Stimulating Factor (CSF)-1 Receptor Blockade Overcomes Overlapping Effects of M-CSF and IL-34 on Myeloid Differentiation and Gene Expression to Reduce Inflammation in Human and Murine Models of Rheumatoid Arthritis, ACR Poster, Nov. 2012, 1 page.
Garnero et al., Biochemical markers of joint tissue turnover in early rheumatoid arthritis, Clin Exp Rheumatol, 2003, 21(Suppl. 31):S54-S58.
Kawanaka et al., CD14+, CD16+ Blood Monocytes and Joint Inflammation in Rheumatoid Arthritis, Arthritis & Rheumatism, 2002, 46(10):2578-2586.
Kelley, Leukocyte—Renal Epithelial Cell Interactions Regulate Lupus Nephritis, Semin Nephrol, 27:59-68, (2007).
Koch et al., Investigating the role of proinflammatory CD16+ monocytes in the pathogenesis of inflammatory bowel disease, Clin Exper Immunol, 2010, 161:332-341.
Kutzelnigg et al., Cortical demyelination and diffuse white matter injury in multiple sclerosis, Brain, 2005, 128:2705-2712.
Le Meur et al., Macrophage accumulation at a site of renal inflammation is dependent on the M-CSF/c-fms pathway, J Leukoc Biol, 2002, 72(3):530-537.
Lenda et al., Negative role of colony-stimulating factor-1 in macrophage, T cell, and B cell mediated autoimmune disease in MRL-Fas(Ipr) mice, J Immunol, 2004, 173(7):4744-4754.
Menke et al., Circulating CSF-1 Promotes Monocyte and Macrophage Phenotypes that Enhance Lupus Nephritis, J Am Soc Nephrol, 2009, 20:2581-2592.
Menke et al., CSF-1 signals directly to renal tubular epithelial cells to mediate repair in mice, J Clin Invest, 2009, 119 (8):2330-2342.
Patel & Player, Colony-Stimulating Factor-1 Receptor Inhibitors for the Treatment of Cancer and Inflammatory Disease, Cuff Topics Med Chem, 2009, 9:599-610.
Rauen & Mertens, Unravelling the pathogenesis of lupus nephritis: novel genetic study confirms decisive contribution of circulating colony-stimulating factor-1 (CSF-1), Int Urol Nephrol, 2010, 42:419-521.
Rossol et al., The CD14-bright CD16+ Monocyte Subset Is Expanded in Rheumatoid Arthritis and Promotes Expansion of the Th17 Cell Population, Arthritis & Rheumatism, 2012, 64(3):671-677.
Rudikoff et al., Single amino acid substitution alterin antigen-binding specificity, PNAS, 1982, 73:1979-1983.
Seshan & Jennette, Renal Disease in Systemic Lupus Erythematosus With Emphasis on Classification of Lupus Glomerulonephritis, Arch Pathol Lab Med, 2009, 133:233-248.
Subimerb et al., Circulating CD14+CD16+ monocyte levels predict tissue invasive character of cholangiocarcinoma, Clinical and Experimental Immunology, 2010, 161:471-479.
TECOmedical Group, TRAP5b Tartrate-Resistant Acid Phosphatase active isoform 5b, A biomarker for osteoclastic bone-resrporption activity, Bone-resorption in renal insufficiency, Catalog, Jul. 2011, 20 pages.
Toh et al., Colony Stimulating Factor 1 Receptor Inhibition Has Anti-Inflammatory and Potent Early Onset Bone and Cartilage Protective Effects, Abstract, ACR/ARHP Scientific Meeting, Nov. 7, 2011, 1 page.
Wada et al., Systemic autoimmune nephritogenic components induce CSF-1 and TNF-alpha in MRL kidneys, Kidney International, 1997, 52:934-941.
Wentworth & Davis, Systemic lupus erythematosus, Nature Rev, 2009, 8:103-104.
Wijngaarden et al., Fc-gamma receptor expression levels on monocytes are elevated in rheumatoid arthritis patients with high erythrocyte sedimentation rate who do not use anti-rheumatic drugs, Rheumatology, 2003, 42:681-688.
Yang et al., Increase in the level of macrophage colony-stimulating factor in patients with systemic lupus erythematosus, Ann Rheum Dis, 2008, 67:429-430.
Zhang et al., Hyper-Activated Pro-Inflammatory CD16+ Monocytes Correlate with the Severity of Liver Injury and Fibrosis in Patients with Chronic Hepatitis B, PLoS One, 2011, 6:(3):e17484, 10 pages.
Ziegler-Heitbrock, The CD14 CD16 blood monocytes: their role in infection and inflammation, J Leuko Biol, 2007, 81:584-592.
International Search Report and Written Opinion mailed Sep. 7, 2012 for Application No. PCT/US2012/037520, filed May 11, 2012, 13 pages.
Liu et al., The mechanism of shared but distinct CSF-1R signaling by the non-homologous cytokines IL-34 and CSF-1, Biochimica et Biophysica Acta, 2012, 1824:938-945.
Wei et al., Functional overlap but differential expression of CSF-1 and IL-34 in their CSF-1 receptor-mediated regulation of myeloid cells, J Leukoc Biol, 2010, 88(3):495-505.
Aharinejad et al., Colony-stimulating Factor-1 Blockade by Antisense Oligonucleotides and Small Interfering RNAs Suppresses Growth of Human Mammary Tumor Xenografts in Mice, Cancer Research, vol. 64, Aug. 2004, pp. 5378-5384.
Aharinejad et al., Colony-stimulating Factor-1 Antisense Treatment Suppresses Growth of Human Tumor Xenografts in Mice, Cancer Research, vol. 62, Sep. 2002, pp. 5317-5324.
Ando et al., Imatinib Mesylate Inhibits Osteoclastogenesis and Joint Destruction in Rats with Collagen-induced Arthritis, J. Bone Miner. Metab., vol. 24, Jan. 2006, pp. 274-282.
Apollo Cytokine Research, Human hcx™ M-CSF R, Fc Chimera, Product Information Sheet from http://www.biocompare.com/itemdetails.asp?itemid=837066, Feb. 4, 2008.
Birchenall-Roberts, Inhibition of Murine Monocyte Proliferation by a Colony-stimulating Factor-1 Antisense Oligodeoxynucleotide, J. Immunol., vol. 15, Nov. 1990, pp. 3290-3296.
Bischof et al., Exacerbation of Acute Inflammatory Arthritis by the Colony-stimulating Factors CSF-1 and Granulocyte Macrophage (GM)-CSF: Evidence of Macrophage Infiltration and Local Proliferation, Clin. Exp. Immunol., vol. 119, 2000, pp. 361-367.
Campbell et al., The Colony-stimulating Factors and Collagen-induced Arthritis: Exacerbation of Disease by M-CSF and G-CSF and Requirement for Endogenous M-CSF, Journal of Leukocyte Biology, vol. 68, Jul. 2000.
Chaika et al., CSF-1 Receptor/Insulin Chimera Permits CSF-1-dependent Differentiation of 3T3-L1 Preadipocytes, J. Biol. Chem., vol. 272, No. 18, May 1997, pp. 11968-11974.
Chitu et al, Colony-stimulating Factor-1 in Immunity and Inflammation, Current Opinion in Immunology, vol. 18, No. 1, Feb. 2006, pp. 39-48.
Conway et al., Inhibition of Colony-stimulating-factor-1 Signaling in Vivo with the Orally Bioavailable cFMS Kinase Inhibitor GW2580, PNAS, vol. 102, Nov. 2005, pp. 16078.
Conway et al., Effects of the cFMS Kinase Inhibitor 5-(3-Methoxy-4-((4-methoxybenzyl)oxy)benzyl)pyrimidine-2,4-diamine (GW2580) in Normal and Arthritic Rats, J. Pharmacology and Experimental Therapeutics, vol. 326, No. 1, Apr. 2008, pp. 41-50.
Dandekar et al., Comparison of the Signaling Abilities of the Cytoplasmic Domains of the Insulin Receptor and the Insulin Receptor-related Receptor in 3T3-L1 Adipocytes, Endocrinology, vol. 139, No. 8, Jan. 2008, pp. 3578-3584.
Dewar et al., Imatinib as a Potential Antiresorptive Therapy for Bone Disease, Blood, vol. 107, No. 11, Jun. 2006, pp. 4334-4337.
Goswami et al., Macrophages Promote the Invasion of Breast Carcinoma Cells via a Colony-stimulating Factor-1/Epidermal Growth Factor . . . , Cancer Research., vol. 65, Jun. 2005.
Hamilton, CSF-1 Signal Transduction, Journal of Leukocyte Biology, vol. 62, Aug. 1997, pp. 145-155.
Hamilton, Colony-stimulating Factors in Inflammation and Autoimmunity, Nature Reviews, vol. 8, Jul. 2008, pp. 533-544.
Hegen et al., Utility of Animal Models for Identification of Potential Therapeutics for Rheumatoid Arthritis, Ann. Rheum. Dis., vol. 67, published online Nov. 2007, pp. 1505-1515.
Ide et al., Expression of Colony-stimulating Factor 1 Receptor During Prostate Development and Prostate Cancer Progression, PNAS, vol. 99, No. 22, Oct. 2002, pp. 14404-14409.
Ide et al., Serum Level of Macrophage Colony-stimulating Factor is Increased in Prostate Cancer Patients with Bone Metastasis, Human Cell, vol. 21, No. 1, Feb. 2008, pp. 1-6.

(56) References Cited

OTHER PUBLICATIONS

Irvine et al., A CSF-1 Receptor Kinase Inhibitor Targets Effector Functions and Inhibits Pro-inflammatory Cytokine Production . . . , FASEB, vol. 20, Sep. 2006, pp. E1315-E1326.
Kingsley et al., Molecular Biology of Bone Metastasis, Mol. Cancer Ther., vol. 6, No. 10, Oct. 2007, pp. 2609-2617.
Kitaura et al., M-CSF Mediates TNF-induced Inflammatory Osteolysis, The Journal of Clinical Investigation, vol. 115, No. 12, Dec. 2005, pp. 3418-3427.
Kitaura et al., An M-CSF Receptor c-FMS Antibody Inhibits Mechanical Stress-Induced Root Resorption during Orthodontic Tooth Movement in Mice, Angle Orthodontist, vol. 79, No. 5, 2009, pp. 835-841.
Kluger et al., Macrophage Colony-stimulating Factor-1 Receptor Expression is Associated with Poor Outcome in Breast Cancer by Large Cohort Tissue Microarray Analysis, Clinical Cancer Res, vol. 10, Jan. 2004, pp. 173.
Kubota et al., M-CSF Inhibition Selectively Targets Pathological Angiogenesis and Lymphangiogenesis, J. Exp. Med., vol. 206, No. 5, Apr. 2009, pp. 1089-1102.
Kutza et al., Macrophage Colony-stimulating Factor Antagonists Inhibit Replication of HIV-1 in Human Macrophages, The Journal of Immunology, 2000, vol. 164, pp. 4955-4960.
Lee et al., Functional Dissection of Structural Domains in the Receptor for Colony-stimulating Factor-1, J. Biol. Chem., vol. 267, Aug. 1992, pp. 16472-16483.
Li et al., Conditional Deletion of the Colony Stimulating Factor-1 Receptor (c-fms Proto-Oncogene) in Mice, Genesis, vol. 44, May 2006, pp. 328-335.
Li et al., Role of Dimerization and Modification of the CSF-1 Receptor in its Activation and Internalization During the CSF-1 Response, The EMBO Journal, 1991, pp. 277-288.
Lim et al., Antibody blockade of c-fms suppresses the progression of inflammation and injury in early diabetic nephropathy in obese db/db mice, Diabetologia, vol. 52, 2009, pp. 1669-1679.
Lin et al., Colony-stimulating Factor 1 Promotes Progression of Mammary Tumors to Malignancy, J. Exp. Med., vol. 193, No. 6, Mar. 2001, pp. 727-739.
Lin et al., The Macrophage Growth Factor CSF-1 in Mammary Gland Development and Tumor Progression, J. Mammary Gland Biology and Neoplasia, vol. 7, Apr. 2002, pp. 147-162.
Lin et al., Discovery of a Cytokine and Its Receptor by Functional Screening of the Extracellular Proteome, Science, vol. 320, May 2008, pp. 807-811.
Lin et al. Regulation of Myeloid Growth and Differentiation by a Novel Cytokine, Interleukin-34 (IL-34), via the CSF-1 Receptor, poster presented at Cytokines in Health & Disease, Fifteenth Annual Conference of the International Cytokine Society (San Francisco, CA, Oct. 26-30, 2007, 1 page.
Lipton, Future Treatment of Bone Metastases, Clin. Cancer Res., vol. 12, 20 Suppl., Oct. 2006, pp. 6305s-6308s.
Lopez-Diego et al., Novel Therapeutic Strategies for Multiple Sclerosis—A Multifaceted Adversary, Nature Reviews Drug Discovery, vol. 7, Nov. 2008, pp. 909-925.
MacDonald et al., An Antibody Against the Colony-stimulating Factor 1 Receptor Depletes the Resident Subset of Monocytes and Tissue- and Tumor-associated Macrophages But Does Not Inhibit Inflammation, Blood, vol. 116, Aug. 2010, pp. 3955-3963.
Mancino et al., Breast Cancer Increases Osteoclastogenesis by Secreting M-CSF and Upregulating RANKL in Stromal Cells, J. Surgical Research, vol. 100, Jul. 2001, pp. 18-24.
Mroczko et al., Serum Macrophage-colony Stimulating Factor Levels in Colorectal Cancer Patients Correlate with Lymph Node Metastasis and Poor Prognosis, Clinica Chimica Acta., vol. 380, Feb. 2007, pp. 208-212.
Montell, Metastasis Movies, Macrophages, Molecules and More, EMBO Reports, vol. 4, No. 5, Apr. 2003, pp. 458-462.
Murray et al., SU11248 Inhibits Tumor Growth and CSF-1 R-dependent Osteolysis in an Experimental Breast Cancer Bone Metastasis Model, Clinical & Experimental Metastasis, vol. 2, Aug. 2003, pp. 757-766.
Ohno et al., A c-Fms Tyrosine Kinase Inhibitor, Ki20227, Suppresses Osteoclast Differentiation and Osteolytic Bone Destruction in a Bone Metastasis, Mol. Cancer Ther., vol. 5, Nov. 2006, pp. 2634.
Ohno et al., The Orally-active and Selective c-FMS tyrosine Kinase Inhibitor Ki20227 Inhibits Disease Progression in a Collagen-induced Arthritis Mouse Model, Eur. J. Immunol., 2008, vol. 38:283-291.
Paniagua et al., c-Fms-mediated Differentiation and Priming of Monocyte Lineage Cells Plays a Central Role in Autoimmune Arthritis, Arthritis Research & Therapy, vol. 12, No. R32, Feb. 2010, pp. 1-45.
Paulus et al., Colony-stimulating Factor-1 Antibody Reverses Chemoresistance in Human MCF-7 Breast Cancer Xenografts, Cancer Res., vol. 66, No. 8, Apr. 2006, pp. 4349-4356.
Pederson et al., Identification of Breast Cancer Cell Line-derived Paracrine Factors That Stimulate Osteoclast Activity, Cancer Research, vol. 59, Nov. 1999, pp. 5849-5855.
Pixley et al., CSF-1 Regulation of the Wandering Macrophage: Complexity in Action, Trends in Cell Biology, vol. 14, No. 11, Nov. 2004, pp. 628-638.
Prince et al., 8: Disorders of Bone and Mineral Other Than Osteoporosis, MJA, vol. 180, Apr. 2004, pp. 354-359.
Qiu et al., Primary Structure of c-kit: Relationship with the CSF-1/PDGF Receptor Kinase Family—Oncogenic Activation of v-kit Involves Deletion of Extracellular Domain and C Terminus, The EMBO Journal, vol. 7, No. 4, Jan. 1988, pp. 1003-1011.
R&D Systems, Inc., Recombinant Human M-CSF R/Fc Chimera, Specifications and Use, Catalog No. 329-MR, Nov. 2007, 2 pages.
Rahimi et al., Receptor Chimeras Indicate that the Vascular Endothelial Growth Factor Receptor-1 (VEGFR-1) Modulates Mitogenic Activity of VEGFR-2 in Endothelial Cells, J. Biol. Chem., vol. 275, No. 22, Jun. 2000, pp. 16986-16992.
Ross, M-CSF, c-Fms, and Signaling in Osteoclasts and Their Precursors, Annals NY Acad. Sci., vol. 1068, 2006, pp. 110-116.
Roussel et al., Colony-stimulating Factor 1-mediated Regulation of a Chimeric c-fms/ v-fms Receptor Containing the v-fms-encoded Tyrosine Kinase Domain, PNAS, vol. 85, Aug. 1988, pp. 5903-5907.
Sapi, The Role of CSF-1 in Normal Physiology of Mammary Gland and Breast Cancer: An Update, Exp. Biol. Med., vol. 229, 2004, pp. 1-11.
Sarma et al., Macrophage Colony-stimulating Factor Induces Substantial Osteoclast Generation and Bone Resorption in Human Bone Marrow Cultures, Blood, vol. 88, No. 7, Oct. 1996, pp. 2531-2540.
Shaposhink et al., Arterial Colony Stimulating Factor-1 Influences Atherosclerotic Lesions by Regulating Monocyte Migration and Apoptosis, J. Lipid Research, vol. 51, 2010, pp. 1962-1970.
Sherr et al., Inhibition of Colony-Stimulating Factor-1 Activity by Monoclonal Antibodies to the Human CSF-1 Receptor, Blood, vol. 73, No. 7, May 1989, pp. 1786-1793.
Sherr, Colony-Stimulating Factor-1 Receptor, Blood, vol. 75, No. 1, Jan. 1990, pp. 1-12.
Steinman et al., Virtues and Pitfalls of EAE for the Development of Therapies for Multiple Sclerosis, Trends in Immunology, 2005, 26(11):565-571.
Suzuki et al., Differences in Bone Responses to Recombinant Human Granulocyte Colony-stimulating Factor Between Mice and Rats, J. Toxicol. Sci., vol. 33, No. 2, 2008, pp. 245-249.
Sweet et al., CSF-1 as a Regulator of Macrophage Activation and Immune Response, AI&TE, vol. 51, 2003, pp. 169-177.
Tamura et al., Tyrosine Kinase as Targets for Anti-inflammatory Therapy, Anti-Inflammatory & Anti-Allergy Agents in Medicinal Chemistry, vol. 6, No. 1, 2007, pp. 47-60.
Tanaka et al., Macrophage Colony-stimulating Factor is Indispensable for Both Proliferation and Differentiation of Osteoclast Progenitors, J. Clin. Invest., vol. 91, Jan. 1993, pp. 257-263.
Teitelbaum, Osteoclasts: What Do They Do and How Do They Do It? Am. J. Pathol., vol. 170, No. 2, Feb. 2007, pp. 427-435.

(56) References Cited

OTHER PUBLICATIONS

Uemura et al., The Selective M-CSF Receptor Tyrosine Kinase Inhibitor Ki20227 Suppresses Experimental Autoimmune Encephalomyelitis, J. Neuroimmunology, vol. 195, Jan. 2008, pp. 73-80.
Usbiological, CD115, Recombinant, Human, Fc Chimera (BSA Free) (c-fms, Fms, CSF-1R, M-CSFR), from Google's cache of http://usbio.net/Product.spx?ProdSku+C2447-52E1.
Van Daalen Wetters et al., Random Mutagenesis of CSF-1 Receptor (FMS) Reveals Multiple Sites for Activating Mutations within the Extracellular Domain, The EMBO Journal, 1992, 11:551-557.
Virk et al., Tumor Metastasis to Bone, Arthritis Research & Therapy, vol. 9, Suppl. 1, 2007, S5, pp. 1-10.
Walsh et al., Post-translational Modifications in the Context of Therapeutic Proteins, Nature Biotechnology, vol. 24, No. 10, Oct. 2006, pp. 1241-1252.
Wang et al., Identification of the Ligand-binding Regions in the Macrophage Colony-stimulating Factor Receptor Extracellular Domain, Mol. Cell Biol., Sep. 1993, pp. 5348-5359.
Weihofen et al., Release of Signal Peptide Fragments Into the Cytosol Requires Cleavage in the Transmembrane Region by a Protease Activity That is Specifically Blocked by a Novel Cysteine Protease Inhibitor, J. Biol. Chem., vol. 275, No. 40, Oct. 2000, pp. 30951-30956.
Wu et al., Enhancement of J6-1 Human Leukemic Cell Proliferation by Membrane-bound M-CSF Through a Cell-Cell Contact Mechanism II. Role of an M-CSF Receptor-like Membrane Protein, Leukemia Research, vol. 22, 1998, pp. 55-60.
Wyckoff et al., A Paracrine Loop Between Tumor Cells and Macrophages is Required for Tumor Cell Migration in Mammary Tumors, Cancer Research, vol. 64, Oct. 2004, pp. 7022-7029.
Yano et al., Macrophage Colony-stimulating Factor Gene Transduction into Human Lung Cancer Cells Differentially Regulates Metastasis . . . , Cancer Research, Feb. 1997, pp. 784.
Yao et al., Tumor Necrosis Factor-α Increases Circulating Osteoclast Precursor Numbers By Promoting Their Proliferation and Differentiation in the Bone Marrow Through Up-regulation of c-Fms Expression, J. Biol Chem., vol. 281, Apr. 2006, pp. 11846.
Yoshimoto et al., Elevated levels of Fractalkine Expression and Accumulation of CD16+ Monocytes in Glomeruli of Active Lupus Nephritis, Am. J. Kidney Disease, vol. 50, No. 1, Jul. 2007, pp. 47-58.
Zheng et al., Expression of Bioactive Human M-Csf Soluble Receptor in Transgenic Tobacco Products, Protein Expression and Purification, 2006, 46:367-373; available online Aug. 15, 2005.
International Search Report and the Written Opinion mailed Jan. 31, 2012 for International Patent Application PCT/US2011/035231, filed May 4, 2011.
International Search Report and Written Opinion mailed May 24, 2010 for Application No. PCT/US2009/006301, filed Nov. 25, 2009.
International Search Report and Written Opinion mailed Jun. 9, 2010 for Application No. PCT/US2009/006299, filed Nov. 25, 2009.
Response to Restriction Election Requirement filed May 3, 2011, for U. S. Appl. No. 12/626,583 (3 pages).
Office Action mailed Jun. 21, 2011, for U.S. Appl. No. 12/626,583 (14 pages).
Reply to Office Action filed Aug. 1, 2011, for U.S. Appl. No. 12/626,583 (15 pages).
Notice of Allowance and Fees Due and Examiner initiated interview summary mailed Dec. 8, 2011, for U.S. Appl. No. 12/626,583 (9 pages).
Office Action mailed Nov. 16, 2010, for U.S. Appl. No. 12/626,598 (7 pages).
Amendment and Response to Restriction Requirement filed Feb. 16, 2011, for U.S. Appl. No. 12/626,598 (7 pages).
Office Action mailed Mar. 16, 2001, for U.S. Appl. No. 12/626,598 (12 pages).
Reply to Office Action filed Jun. 16, 2011 for U.S. Appl. No. 12/626,598 (7 pages).
Final Office Action mailed Aug. 3, 2011, for U.S. Appl. No. 12/626,598 (6 pages).
Amendment After Final filed Aug. 16, 2011, for U.S. Appl. No. 12/626,598 (8 pages).
Notice of Allowance and Fees Due mailed Oct. 13, 2011, for U.S. Appl. No. 12/626,598 (6 pages).
Burns & Wilks, c-FMS inhibitors: a patent review, Expert Opin Ther Pat., 2011, 21(2):147-165.
File History of U.S. Appl. No. 13/891,455, filed May 10, 2013.
File History of U.S. Appl. No. 14/014,446, filed Aug. 30, 2013.
Priceman et al., Targeting distinct tumor-infiltrating myeloid cells by inhibiting CSF-1 receptor: combating tumor evasion of antiangiogenic therapy, Blood, 2010 115(7):1461-1471.
Sasmono et al., Mouse neutrophilic granulocytes express mRNA encoding the macrophage colony-stimulating factor receptor (CSF-1R) as well as many other macrophage-specific transcripts and can transdifferentiate into macrophages in vitro in response to CSF-1, J Leukoc Biol, 2007, 82(1):111-123.
Sigma Product Information, "Macrophage Cologny Stimulating Factor Receptor/Fc Chimera (M-CSF R, CD115) Human, Recombinant, Expressed in mouse NSO cells," Product No. M 7559, 2011, 2 pages.
Aikawa et al., PU.1-mediated upregulation of CSF1R is crucial for leukemia stem cell potential induced by MOZ-TIF2, Nature Medicine, vol. 16, May 2010, pp. 580-585.
Pasternak et al., ACC/AHA/NHLBI Clinical Advisory on the Use and Safety of Statins, J Am College Cardiology, 2002, 40(3):567-572.
Seeff, Should There Be a Standard of Care (SOC) for Drug-Induced Liver Injury (DILI)?, Presentation, Drug-Induced Liver Injury: Are We Ready to Look, Mar. 23-24, 2011, AASLD, FDA/CDER, PhRMA, 20 pages.
International Search Report and Written Opinion mailed Jan. 7, 2014, for Application No. PCT/US2013/057442, filed Aug. 30, 2013, 15 pages.

| Ab ID | L/H chains | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 |
|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | CDRL2 | | | | | | | | | | | | | | | | |
| cAb0301 | parental | W | Y | Q | Q | K | P | G | Q | A | P | K | L | L | I | Y | A | A | S | N | L | E | S | G | I | P | A | R | F | S | G | S | G | S | G | T | D |
| | human acceptor D | W | Y | Q | Q | K | P | G | Q | A | P | R | L | L | I | Y | A | A | S | N | L | E | S | G | I | P | A | R | F | S | G | S | G | S | G | T | D |
| Ab1 | h0301-L0H0 | W | Y | Q | Q | K | P | G | Q | A | P | R | L | L | I | Y | A | A | S | N | L | E | S | G | I | P | A | R | F | S | G | S | G | S | G | T | D |
| Ab2 | h0301-L0H1 | W | Y | Q | Q | K | P | G | Q | A | P | R | L | L | I | Y | A | A | S | N | L | E | S | G | I | P | A | R | F | S | G | S | G | S | G | T | D |
| Ab3 | h0301-L0H2 | W | Y | Q | Q | K | P | G | Q | A | P | R | L | L | I | Y | A | A | S | N | L | E | S | G | I | P | A | R | F | S | G | S | G | S | G | T | D |
| Ab4 | h0301-L1H0 | W | Y | Q | Q | K | P | G | Q | A | P | R | L | L | I | Y | A | A | S | N | L | E | S | G | I | P | A | R | F | S | G | S | G | S | G | T | D |
| Ab5 | h0301-L1H1 | W | Y | Q | Q | K | P | G | Q | A | P | R | L | L | I | Y | A | A | S | N | L | E | S | G | I | P | A | R | F | S | G | S | G | S | G | T | D |
| Ab6 | h0301-L1H2 | W | Y | Q | Q | K | P | G | Q | A | P | R | L | L | I | Y | A | A | S | N | L | E | S | G | I | P | A | R | F | S | G | S | G | S | G | T | D |
| cAb0302 | parental | W | P | Q | Q | K | P | G | Q | A | P | K | L | L | I | Y | T | A | S | N | L | E | S | G | I | P | A | R | F | S | G | S | G | S | G | T | D |
| | human acceptor E | W | Y | Q | Q | K | P | G | Q | A | P | R | L | L | I | Y | A | A | S | N | L | E | S | G | I | P | A | R | F | S | G | S | G | S | G | T | D |
| Ab7 | h0302-L0H1 | W | Y | Q | Q | K | P | G | Q | A | P | R | L | L | I | Y | T | A | S | N | L | E | S | G | I | P | A | R | F | S | G | S | G | S | G | T | D |
| Ab8 | h0302-L1H1 | W | Y | Q | Q | K | P | G | Q | A | P | R | L | L | I | Y | T | A | S | N | L | E | S | G | I | P | A | R | F | S | G | S | G | S | G | R | T | D |
| Ab9 | h0302-L2H1 | W | F | Q | Q | K | P | G | Q | A | P | R | L | L | I | Y | T | A | S | N | L | E | S | G | I | P | A | R | F | S | G | S | G | S | G | R | T | D |
| Ab10 | h0302-L0H2 | W | Y | Q | Q | K | P | G | Q | A | P | R | L | L | I | Y | T | A | S | N | L | E | S | G | I | P | A | R | F | S | G | S | G | S | G | T | D |
| Ab11 | h0302-L1H2 | W | Y | Q | Q | K | P | G | Q | A | P | R | L | L | I | Y | T | A | S | N | L | E | S | G | I | P | A | R | F | S | G | S | G | S | G | R | T | D |
| Ab12 | h0302-L2H2 | W | F | Q | Q | K | P | G | Q | A | P | R | L | L | I | Y | T | A | S | N | L | E | S | G | I | P | A | R | F | S | G | S | G | S | G | R | T | D |
| cAb0311 | parental | W | Y | Q | Q | K | P | G | Q | A | P | K | L | L | I | Y | A | A | S | N | L | E | S | G | I | P | A | R | F | S | G | S | G | S | G | A | D |
| | human acceptor F | W | Y | Q | Q | K | P | G | Q | A | P | R | L | L | I | Y | T | A | S | N | L | E | S | G | I | P | A | R | F | S | G | S | G | S | G | T | D |
| Ab13 | h0311-L0H1 | W | Y | Q | Q | K | P | G | Q | A | P | R | L | L | I | Y | A | A | S | N | L | E | S | G | I | P | A | R | F | S | G | S | G | S | G | A | D |
| Ab14 | h0311-L1H1 | W | Y | Q | Q | K | P | G | Q | A | P | R | L | L | I | Y | A | A | S | N | L | E | S | G | I | P | A | R | F | S | G | S | G | S | G | T | D |
| Ab15 | h0311-L0H2 | W | Y | Q | Q | K | P | G | Q | A | P | R | L | L | I | Y | A | A | S | N | L | E | S | G | I | P | A | R | F | S | G | S | G | S | G | A | D |
| Ab16 | h0311-L1H2 | W | Y | Q | Q | K | P | G | Q | A | P | R | L | L | I | Y | A | A | S | N | L | E | S | G | I | P | A | R | F | S | G | S | G | S | G | T | D |

FIG. 2C

| Ab ID | L/H chains | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | SEQ ID NO |
|---|---|---|---|---|---|---|---|---|---|---|---|---|---|---|---|---|---|---|---|---|---|---|---|---|---|---|---|---|---|---|---|---|---|---|---|---|---|---|---|
| cAb0301 | parental | F | T | L | N | I | H | P | V | E | E | E | D | A | A | T | Y | Y | C | H | L | S | N | E | D | L | S | T | P | G | Q | G | T | K | L | E | I | K | 10 |
| | human acceptor D | P | T | L | T | I | S | S | L | E | P | E | D | F | A | V | Y | Y | C | | | | | | | | | | | | | | | | | | | | 81-84 |
| Ab1 | h0301-L0H0 | F | T | L | T | I | S | S | L | E | P | E | D | F | A | V | Y | Y | C | H | L | S | N | E | D | L | S | T | P | G | Q | G | T | K | V | E | I | K | 46 |
| Ab2 | h0301-L0H1 | F | T | L | T | I | S | S | L | E | P | E | D | F | A | V | Y | Y | C | H | L | S | N | E | D | L | S | T | P | G | Q | G | T | K | V | E | I | K | 46 |
| Ab3 | h0301-L0H2 | F | T | L | T | I | S | S | L | E | P | E | D | F | A | V | Y | Y | C | H | L | S | N | E | D | L | S | T | P | G | Q | G | T | K | V | E | I | K | 46 |
| Ab4 | h0301-L1H0 | F | T | L | T | I | S | S | L | E | P | E | D | F | A | V | Y | Y | C | H | L | S | N | E | D | L | T | T | P | G | Q | G | T | K | V | E | I | K | 47 |
| Ab5 | h0301-L1H1 | F | T | L | T | I | S | S | L | E | P | E | D | F | A | V | Y | Y | C | H | L | S | N | E | D | L | T | T | P | G | Q | G | T | K | V | E | I | K | 47 |
| Ab6 | h0301-L1H2 | F | T | L | T | I | S | S | L | E | P | E | D | F | A | V | Y | Y | C | H | L | S | N | E | D | L | T | T | P | G | Q | G | T | K | V | E | I | K | 47 |
| cAb0302 | parental | F | T | L | T | I | D | P | V | E | A | D | D | A | A | T | Y | F | C | O | Q | S | K | E | L | P | W | T | P | G | Q | G | T | K | L | E | I | K | 12 |
| | human acceptor E | P | T | L | T | I | S | S | L | E | P | E | D | F | A | V | Y | Y | C | | | | | | | | | | | | | | | | | | | | 85-88 |
| Ab7 | h0302-L0H1 | F | T | L | T | I | S | S | L | E | P | E | D | F | A | V | Y | Y | C | Q | Q | S | K | E | L | P | W | T | P | G | Q | G | T | K | V | E | I | K | 48 |
| Ab8 | h0302-L0H2 | F | T | L | T | I | S | S | L | E | P | E | D | F | A | V | Y | Y | C | Q | Q | S | K | E | L | P | W | T | P | G | Q | G | T | K | V | E | I | K | 49 |
| Ab9 | h0302-L1H1 | F | T | L | T | I | S | S | L | E | P | E | D | F | A | V | Y | Y | C | Q | Q | S | K | E | L | P | W | T | P | G | Q | G | T | K | V | E | I | K | 50 |
| Ab10 | h0302-L1H2 | F | T | L | T | I | S | S | L | E | P | E | D | F | A | V | Y | Y | C | Q | Q | S | K | E | L | P | W | T | P | G | Q | G | T | K | V | E | I | K | 48 |
| Ab11 | h0302-L2H1 | F | T | L | T | I | S | S | L | E | P | E | D | F | A | V | Y | Y | C | Q | Q | S | K | E | L | P | W | T | P | G | Q | G | T | K | V | E | I | K | 49 |
| Ab12 | h0302-L2H2 | F | T | L | T | I | S | S | L | E | P | E | D | F | A | V | Y | Y | C | Q | Q | S | K | E | L | P | W | T | P | G | Q | G | T | K | V | E | I | K | 50 |
| cAb0311 | parental | F | T | L | T | I | S | P | V | E | E | E | D | A | A | T | Y | Y | C | Q | Q | G | N | E | D | P | W | T | P | G | G | G | T | K | L | E | I | K | 14 |
| | human acceptor F | P | T | L | T | I | S | S | L | E | P | E | D | F | A | V | Y | Y | C | | | | | | | | | | | | | | | | | | | | 89-92 |
| Ab13 | h0311-L0H1 | F | T | L | T | I | S | S | L | E | P | E | D | F | A | V | Y | Y | C | Q | Q | G | N | E | D | P | W | T | P | G | Q | G | T | K | V | E | I | K | 51 |
| Ab14 | h0311-L1H1 | F | T | L | T | I | S | S | L | E | P | E | D | F | A | V | Y | Y | C | Q | Q | G | N | E | D | P | W | T | P | G | Q | G | T | K | V | E | I | K | 52 |
| Ab15 | h0311-L1H2 | F | T | L | T | I | S | S | L | E | P | E | D | F | A | V | Y | Y | C | Q | Q | G | N | E | D | P | W | T | P | G | Q | G | T | K | V | E | I | K | 51 |
| Ab16 | h0311-L2H2 | F | T | L | T | I | S | S | L | E | P | E | D | F | A | V | Y | Y | C | Q | Q | G | N | E | D | P | W | T | P | G | Q | G | T | K | V | E | I | K | 52 |

(Columns 89–97 correspond to CDRL3)

US 8,747,845 B2

METHODS OF TREATMENT BY ADMINISTERING ANTIBODIES THAT BIND COLONY STIMULATING FACTOR 1 RECEPTOR (CSF1R)

This application is a divisional of U.S. patent application Ser. No. 13/100,990, filed May 5, 2011, now U.S. Pat. No. 8,206,715, which claims the benefit of U.S. Provisional Application No. 61/331,177, filed May 4, 2010, each of which is incorporated by reference herein in its entirety for any purpose.

TECHNICAL FIELD

Antibodies that bind CSF1R are provided. Antibody heavy chains and light chains that are capable of forming antibodies that bind CSF1R are also provided. In addition, antibodies, heavy chains, and light chains comprising one or more particular complementarity determining regions (CDRs) are provided. Polynucleotides encoding antibodies to CSF1R are provided. Polynucleotides encoding antibody heavy chains or lights chains are also provided. Methods of treatment using antibodies to CSF1R are provided. Such methods include, but are not limited to, methods of treating rheumatoid arthritis, bone loss, and multiple sclerosis.

BACKGROUND

Colony stimulating factor 1 receptor (referred to herein as CSF1R; also referred to in the art as FMS, FIM2, C-FMS, and CD115) is a single-pass transmembrane receptor with an N-terminal extracellular domain (ECD) and a C-terminal intracellular domain with tyrosine kinase activity. Ligand binding of CSF1 or the interleukin 34 ligand (referred to herein as IL34; Lin et al., Science 320: 807-11 (2008)) to CSF1R leads to receptor dimerization, upregulation of CSF1R protein tyrosine kinase activity, phosphorylation of CSF1R tyrosine residues, and downstream signaling events. Both CSF1 and IL34 stimulate monocyte survival, proliferation, and differentiation into macrophages.

Many tumor cells have been found to secrete CSF1, which activates monocyte/macrophage cells through CSF1R. The level of CSF1 in tumors has been shown to correlate with the level of tumor-associated macrophages (TAMs) in the tumor. Higher levels of TAMs have been found to correlate with poorer patient prognoses. In addition, CSF1 has been found to promote tumor growth and progression to metastasis in, for example, human breast cancer xenografts in mice. See, e.g., Paulus et al., Cancer Res. 66: 4349-56 (2006). Further, CSF1R appears to play a role in osteolytic bone destruction in bone metastasis, as a small molecule inhibitor of receptor tyrosine kinase activity suppresses that destruction. See, e.g., Ohno et al., Mol. Cancer Ther. 5: 2634-43 (2006).

CSF1 and its receptor have also been found to be involved in various inflammatory and autoimmune diseases. See, e.g., Hamilton, Nat. Rev. 8: 533-44 (2008). For example, synovial endothelial cells from joints afflicted with rheumatoid arthritis have been found to produce CSF1, suggesting a role for CSF1 and its receptor in the disease. Blocking CSF1R activity with an antibody results in positive clinical effects in mouse models of arthritis, including a reduction in the destruction of bone and cartilage and a reduction in macrophage numbers. See, e.g., Kitaura et al., J. Clin. Invest. 115: 3418-3427 (2005).

Mature differentiated myeloid lineage cells such as macrophages, microglial cells, and osteoclasts contribute to pathology of various diseases such as rheumatoid arthritis, multiple sclerosis and diseases of bone loss. Differentiated myeloid lineage cells are derived from peripheral blood monocyte intermediates. CSF1R stimulation contributes to development of monocytes from bone marrow precursors, to monocyte proliferation and survival, and to differentiation of peripheral blood monocytes into differentiated myeloid lineage cells such as macrophages, microglial cells, and osteoclasts. CSF1R stimulation thus contributes to proliferation, survival, activation, and maturation of differentiated myeloid lineage cells, and in the pathologic setting, CSF1R stimulation contributes to the ability of differentiated myeloid lineage cells to mediate disease pathology.

Additional antagonists of CSF1R signaling would therefore be useful in the treatment of various CSF1R-related diseases, such as cancer, inflammatory conditions, and autoimmune diseases.

SUMMARY

The present inventors have invented a new set of antibodies, including humanized antibodies, directed against human CSF1R extracellular domain (CSF1R ECD). A Fab phage display library was made from spleens of mice that were immunized with a human CSF1R ECD-Fc fusion protein. 1056 phage clones expressing Fabs that bind to CSF-1R ECD-Fc were isolated through panning of this library. When the 1056 Fabs were expressed as purified protein, 668 were found to bind to CSF1R ECD. Of those 668 binding Fabs, only 121 Fabs blocked binding of CSF1 and/or IL34 to CSF1R. Only 33 of those Fabs were found to block binding of both CSF1 and IL34 to CSF1R. Upon sequencing, the 33 Fabs represented 19 unique sets of sequences. Eleven Fabs with subnanomolar affinity for human CSF1R ECD were chosen to make chimeric antibodies for further study. Based on the human and cynomolgus monkey CSF1R binding affinities, blocking of CSF1 and IL34 binding to CSF1R, and inhibition of ligand-induced phorphorylation of CSF1R, three chimeric antibodies were selected for humanization, and sixteen humanized antibodies were made based on those three chimeric antibodies.

Fourteen of the sixteen humanized antibodies retained subnanomolar binding affinities for human CSF1R ECD. See, e.g., Table 5. These humanized antibodies block binding of both ligands CSF1 and IL34 to human CSF1R, and many also block binding of both CSF1 and IL34 to cynomolgus monkey CSF1R. See, e.g., Table 4.

For therapeutic drug development, it is beneficial to have antibodies that bind to both human and cynomolgus monkey antigens with similar affinity. The three chimeric antibodies chosen for humanization were selected in part because they had similar binding affinities for human and cynomolgus CSF1R ECD. Most of the humanized versions of one of the chimeric antibodies, 0302, however, lost significant binding affinity for cynomolgus monkey CSF1R ECD upon humanization, although they retained strong human CSF1R ECD binding affinity. See, e.g., Table 3. Humanized versions of 0301 and 0311 retained similarly strong binding to both human and cynomolgus monkey CSF1R ECD, with binding affinity differences for the two species of less than about 2-fold.

Based on CSF1R binding affinities, ligand inhibition, and the potential for immunogenicity, three humanized antibodies were selected for additional studies. The three humanized antibodies were derived from the two chimeric antibodies that did not significantly lose cynomolgus monkey CSF1R binding affinity upon humanization. Those three humanized antibodies inhibit ligand-induced phosphorylation of human CSF1R, and also block ligand-induced proliferation and survival responses in primary human monocytes. See, e.g., Tables 6 and 7, and FIGS. 10 and 11. Thus, these antibodies are useful for treating diseases involving, for example, ligand-induced proliferation and survival responses in primary human monocytes.

Blocking CSF1R-induced responses with an anti-CSF1R antibody should inhibit proliferation, survival, activation, maturation of differentiated myeloid lineage cells and attenuate their ability to mediate disease pathology. In addition, blocking CSF1R-induced responses with an anti-CSF1R antibody should inhibit differentiation of peripheral blood monocyte intermediates into differentiated myeloid lineage cells, decreasing the number of pathology-mediating differentiated myeloid lineage cells.

Accordingly, the humanized anti-CSF1R antibodies described herein can be used to treat chronic diseases with extant symptoms by inhibiting the ability of differentiated myeloid lineage cells to mediate disease pathology. The humanized antibodies can also be used to treat chronic diseases that are relapsing and remitting in nature by inhibiting the development of new pathology-mediating myeloid lineage cells differentiated from peripheral blood monocytes during the remitting phase of the disease, thus attenuating the number of and new formation of the pathology-mediating cells.

In some embodiments, an isolated antibody comprising a heavy chain and a light chain is provided, wherein the antibody binds to CSF1R. In some embodiments, the heavy chain and/or light chain have the following structure.

In some embodiments, the heavy chain comprises a sequence that is at least 90%, at least 95%, at least 97%, at least 99%, or 100% identical to a sequence selected from SEQ ID NOs: 9, 11, 13, and 39 to 45. In some embodiments, the light chain comprises a sequence that is at least 90%, at least 95%, at least 97%, at least 99%, or 100% identical to a sequence selected from SEQ ID NOs: 10, 12, 14, and 46 to 52. In some embodiments, the heavy chain comprises a sequence that is at least 90%, at least 95%, at least 97%, at least 99%, or 100% identical to a sequence selected from SEQ ID NOs: 9, 11, 13, and 39 to 45, and the light chain comprises a sequence that is at least 90%, at least 95%, at least 97%, at least 99%, or 100% identical to a sequence selected from SEQ ID NOs: 10, 12, 14, and 46 to 52.

In some embodiments, the HC CDR1, HC CDR2, and HC CDR3 comprise a set of sequences selected from: (a) SEQ ID NOs: 15, 16, and 17; (b) SEQ ID NOs: 21, 22, and 23; and (c) SEQ ID NOs: 27, 28, and 29. In some embodiments, the LC CDR1, LC CDR2, and LC CDR3 comprise a set of sequences selected from: (a) SEQ ID NOs: 18, 19, and 20; (b) SEQ ID NOs: 24, 25, and 26; and (c) SEQ ID NOs: 30, 31, and 32.

In some embodiments, the heavy chain comprises an HC CDR1, HC CDR2, and HC CDR3, wherein the HC CDR1, HC CDR2, and HC CDR3 comprise a set of sequences selected from: (a) SEQ ID NOs: 15, 16, and 17; (b) SEQ ID NOs: 21, 22, and 23; and (c) SEQ ID NOs: 27, 28, and 29; and the light chain comprises an LC CDR1, LC CDR2, and LC CDR3, wherein the LC CDR1, LC CDR2, and LC CDR3 comprise a set of sequences selected from: (a) SEQ ID NOs: 18, 19, and 20; (b) SEQ ID NOs: 24, 25, and 26; and (c) SEQ ID NOs: 30, 31, and 32.

In some embodiments, an isolated antibody is provided, wherein the antibody comprises a heavy chain and a light chain, wherein the antibody comprises:

(a) a heavy chain comprising a sequence that is at least 95%, at least 97%, at least 99%, or 100% identical to SEQ ID NO: 9 and a light chain comprising a sequence that is at least 95%, at least 97%, at least 99%, or 100% identical to SEQ ID NO: 10;

(b) a heavy chain comprising a sequence that is at least 95%, at least 97%, at least 99%, or 100% identical to SEQ ID NO: 11 and a light chain comprising a sequence that is at least 95%, at least 97%, at least 99%, or 100% identical to SEQ ID NO: 12;

(c) a heavy chain comprising a sequence that is at least 95%, at least 97%, at least 99%, or 100% identical to SEQ ID NO: 13 and a light chain comprising a sequence that is at least 95%, at least 97%, at least 99%, or 100% identical to SEQ ID NO: 14;

(d) a heavy chain comprising a sequence that is at least 95%, at least 97%, at least 99%, or 100% identical to SEQ ID NO: 39 and a light chain comprising a sequence that is at least 95%, at least 97%, at least 99%, or 100% identical to SEQ ID NO: 46;

(e) a heavy chain comprising a sequence that is at least 95%, at least 97%, at least 99%, or 100% identical to SEQ ID NO: 40 and a light chain comprising a sequence that is at least 95%, at least 97%, at least 99%, or 100% identical to SEQ ID NO: 46;

(f) a heavy chain comprising a sequence that is at least 95%, at least 97%, at least 99%, or 100% identical to SEQ ID NO: 41 and a light chain comprising a sequence that is at least 95%, at least 97%, at least 99%, or 100% identical to SEQ ID NO: 46;

(g) a heavy chain comprising a sequence that is at least 95%, at least 97%, at least 99%, or 100% identical to SEQ ID NO: 39 and a light chain comprising a sequence that is at least 95%, at least 97%, at least 99%, or 100% identical to SEQ ID NO: 47;

(h) a heavy chain comprising a sequence that is at least 95%, at least 97%, at least 99%, or 100% identical to SEQ ID NO: 40 and a light chain comprising a sequence that is at least 95%, at least 97%, at least 99%, or 100% identical to SEQ ID NO: 47;

(i) a heavy chain comprising a sequence that is at least 95%, at least 97%, at least 99%, or 100% identical to SEQ ID NO: 41 and a light chain comprising a sequence that is at least 95%, at least 97%, at least 99%, or 100% identical to SEQ ID NO: 47;

and (j) a heavy chain comprising a sequence that is at least 95%, at least 97%, at least 99%, or 100% identical to SEQ ID NO: 42 and a light chain comprising a sequence that is at least 95%, at least 97%, at least 99%, or 100% identical to SEQ ID NO: 48;

(k) a heavy chain comprising a sequence that is at least 95%, at least 97%, at least 99%, or 100% identical to SEQ ID NO: 42 and a light chain comprising a sequence that is at least 95%, at least 97%, at least 99%, or 100% identical to SEQ ID NO: 49;

(l) a heavy chain comprising a sequence that is at least 95%, at least 97%, at least 99%, or 100% identical to SEQ ID NO: 42 and a light chain comprising a sequence that is at least 95%, at least 97%, at least 99%, or 100% identical to SEQ ID NO: 50;

(m) a heavy chain comprising a sequence that is at least 95%, at least 97%, at least 99%, or 100% identical to SEQ ID NO: 43 and a light chain comprising a sequence that is at least 95%, at least 97%, at least 99%, or 100% identical to SEQ ID NO: 48;

(n) a heavy chain comprising a sequence that is at least 95%, at least 97%, at least 99%, or 100% identical to SEQ ID NO:

43 and a light chain comprising a sequence that is at least 95%, at least 97%, at least 99%, or 100% identical to SEQ ID NO: 49;

(o) a heavy chain comprising a sequence that is at least 95%, at least 97%, at least 99%, or 100% identical to SEQ ID NO: 43 and a light chain comprising a sequence that is at least 95%, at least 97%, at least 99%, or 100% identical to SEQ ID NO: 50;

(p) a heavy chain comprising a sequence that is at least 95%, at least 97%, at least 99%, or 100% identical to SEQ ID NO: 44 and a light chain comprising a sequence that is at least 95%, at least 97%, at least 99%, or 100% identical to SEQ ID NO: 51;

(q) a heavy chain comprising a sequence that is at least 95%, at least 97%, at least 99%, or 100% identical to SEQ ID NO: 44 and a light chain comprising a sequence that is at least 95%, at least 97%, at least 99%, or 100% identical to SEQ ID NO: 52;

(r) a heavy chain comprising a sequence that is at least 95%, at least 97%, at least 99%, or 100% identical to SEQ ID NO: 45 and a light chain comprising a sequence that is at least 95%, at least 97%, at least 99%, or 100% identical to SEQ ID NO: 51;

or (s) a heavy chain comprising a sequence that is at least 95%, at least 97%, at least 99%, or 100% identical to SEQ ID NO: 45 and a light chain comprising a sequence that is at least 95%, at least 97%, at least 99%, or 100% identical to SEQ ID NO: 52.

In some embodiments, an antibody is provided, wherein the antibody comprises a heavy chain and a light chain, wherein the antibody comprises: (a) a heavy chain comprising a heavy chain (HC) CDR1 having the sequence of SEQ ID NO: 15, an HC CDR2 having the sequence of SEQ ID NO: 16, and an HC CDR3 having the sequence of SEQ ID NO: 17, and a light chain comprising a light chain (LC) CDR1 having the sequence of SEQ ID NO: 18, a LC CDR2 having the sequence of SEQ ID NO: 19, and a LC CDR3 having the sequence of SEQ ID NO: 20; (b) a heavy chain comprising a heavy chain (HC) CDR1 having the sequence of SEQ ID NO: 21, an HC CDR2 having the sequence of SEQ ID NO: 22, and an HC CDR3 having the sequence of SEQ ID NO: 23, and a light chain comprising a light chain (LC) CDR1 having the sequence of SEQ ID NO: 24, a LC CDR2 having the sequence of SEQ ID NO: 25, and a LC CDR3 having the sequence of SEQ ID NO: 26; or (c) a heavy chain comprising a heavy chain (HC) CDR1 having the sequence of SEQ ID NO: 27, an HC CDR2 having the sequence of SEQ ID NO: 28, and an HC CDR3 having the sequence of SEQ ID NO: 29, and a light chain comprising a light chain (LC) CDR1 having the sequence of SEQ ID NO: 30, a LC CDR2 having the sequence of SEQ ID NO: 31, and a LC CDR3 having the sequence of SEQ ID NO: 32.

In some embodiments, an antibody comprises a heavy chain and a light chain, wherein the antibody comprises: (a) a heavy chain comprising a sequence of SEQ ID NO: 53 and a light chain comprising a sequence of SEQ ID NO: 60; (b) a heavy chain comprising a sequence of SEQ ID NO: 53 and a light chain comprising a sequence of SEQ ID NO: 61; or (c) a heavy chain comprising a sequence of SEQ ID NO: 58 and a light chain comprising a sequence of SEQ ID NO: 65. In some embodiments, an antibody comprises a heavy chain and a light chain, wherein the antibody comprises: (a) a heavy chain consisting of the sequence of SEQ ID NO: 53 and a light chain consisting of the sequence of SEQ ID NO: 60; (b) a heavy chain consisting of the sequence of SEQ ID NO: 53 and a light chain consisting of the sequence of SEQ ID NO: 61; or (c) a heavy chain consisting of the sequence of SEQ ID NO: 58 and a light chain consisting of the sequence of SEQ ID NO: 65.

In some embodiments, an antibody is a humanized antibody. In some embodiments, an antibody is selected from a Fab, an Fv, an scFv, a Fab', and a (Fab')$_2$. In some embodiments, an antibody is a chimeric antibody. In some embodiments, an antibody is selected from an IgA, an IgG, and an IgD. In some embodiments, an antibody is an IgG. In some embodiments, an antibody is an IgG4. In some embodiments, an antibody is an IgG4 comprising an S241P mutation in at least one IgG4 heavy chain constant region.

In some embodiments, an antibody binds to human CSF1R and/or binds to cynomolgus CSF1R. In some embodiments, an antibody blocks ligand binding to CSF1R. In some embodiments, an antibody blocks binding of CSF1 and/or IL34 to CSF1R. In some embodiments, an antibody inhibits ligand-induced CSF1R phosphorylation. In some embodiments, an antibody inhibits CSF1- and/or IL34-induced CSF1R phosphorylation. In some embodiments, an antibody binds to human CSF1R with an affinity ($K_D$) of less than 1 nM. In some embodiments, antibody inhibits monocyte proliferation and/or survival responses in the presence of CSF1 or IL34.

In some embodiments, a pharmaceutical composition comprising an antibody that binds CSF1R is provided.

In some embodiments, an isolated nucleic acid is provided, wherein the isolated nucleic acid comprises a polynucleotide sequence that encodes a heavy chain described above. In some embodiments, an isolated nucleic acid encodes a light chain described above. In some embodiments, an isolated nucleic acid encodes a heavy chain described above and a light chain described above. In some embodiments, a composition is provided, wherein the composition comprises a first nucleic acid that comprises a polynucleotide sequence that encodes a heavy chain described above, and a second nucleic acid that comprises a polynucleotide sequence that encodes a light chain described above. In some embodiments, a host cell comprising a nucleic acid or a composition described above is provided. In some embodiments, a host cell is a eukaryotic host cell. In some embodiments, a host cell is a mammalian host cell. In some embodiments, a host cell is selected from a CHO cell, a 293 cell, an NSO cell, and a PER.C6 cell. In some embodiments, a host cell is a 293-6E cell or a DG44 cell.

In some embodiments, methods of treating disease comprising administering to a patient a pharmaceutical composition comprising an antibody that binds CSF1R is provided. In some embodiments, a method of treating multiple sclerosis comprising administering to a patient a pharmaceutical composition comprising an antibody that binds CSF1R is provided. In some embodiments, a method of treating rheumatoid arthritis comprising administering to a patient a pharmaceutical composition comprising an antibody that binds CSF1R is provided. In some embodiments, a method of treating osteolytic bone loss comprising administering to a patient a pharmaceutical composition comprising an antibody that binds CSF1R is provided. In some embodiments, the osteolytic bone loss is selected from osteoporosis, metastasis-induced osteolytic bone loss, and rheumatoid arthritis-induced bone loss. In some embodiments, a method of treating cancer comprising administering to a patient a pharmaceutical composition comprising an antibody that binds CSF1R is provided. In some embodiments, the cancer is selected from breast cancer, prostate cancer, endometrial cancer, bladder cancer, kidney cancer, esophageal cancer, squamous cell carcinoma, uveal melanoma, follicular lymphoma, renal cell carcinoma, cervical cancer, ovarian cancer, lung cancer, colorectal cancer, brain cancer, pancreatic cancer, head and neck cancer, liver cancer, leukemia, lymphoma, Hodgkin's disease, multiple myeloma, melanoma, astrocytoma, stomach cancer, and pulmonary adenocarcinoma.

In some embodiments, a method of treating an inflammatory condition comprising administering to a patient a pharmaceutical composition comprising an antibody that binds CSF1R is provided.

In some embodiments, antibodies that bind CSF1R and compositions comprising antibodies that bind CSF1R are provided for use in methods of treatment of human or animals. In some embodiments, antibodies that bind CSF1R and compositions comprising antibodies that bind CSF1R are provided for use in a method of treating rheumatoid arthritis in a human or animal. In some embodiments, antibodies that bind CSF1R and compositions comprising antibodies that bind CSF1R are provided for use in a method of treating multiple sclerosis in a human or animal. In some embodiments, antibodies that bind CSF1R and compositions comprising antibodies that bind CSF1R are provided for use in a method of treating cancer in a human or animal. In some embodiments, antibodies that bind CSF1R and compositions comprising antibodies that bind CSF1R are provided for use in a method of treating an inflammatory condition in a human or animal.

BRIEF DESCRIPTION OF THE FIGURES

FIGS. 1A-C show an alignment of the humanized heavy chain variable regions for each of humanized antibodies Ab1 to Ab16, as discussed in Example 4. Boxed residues are amino acids in the human acceptor sequence that were changed back to the corresponding mouse residue.

FIGS. 2A-C show an alignment of the humanized light chain variable regions for each of humanized antibodies Ab1 to Ab 16, as discussed in Example 4 Boxed amino acids are residues in the human acceptor sequence that were changed back to the corresponding mouse residue.

FIG. 3A shows binding curves for parental chimeric antibodies (cAb) 0301 and humanized antibodies (huAb) 0301.1, 0301.2, 0302.3, 0301.4, 0301.5, and 0301.6 (h0301-L0H0, h0301-L0H1, h0301-L0H2, h0301-L1H0, h0301-L1H1, and h0301-L1H2, respectively). FIG. 3B shows binding curves for parental cAb 0302 and humanized antibodies (huAb) 0302.1, 0302.2, 0302.3, 0302.4, 0302.5, and 0302.6 (h0302-L0H1, h0302-L1H1, h0302-L2H1, h0302-L0H2, h0302-L1H2, and h0302-L2H2, respectively). FIG. 3C shows binding curves for parental cAb 0311 and humanized antibodies (huAb) 0311.1, 0311.2, 0311.3, and 0311.4 (h0311-L0H1, h0311-L1H1, h0311-L0H2, and h0311-L1H2, respectively).

FIG. 4A shows binding curves for parental cAb 0301 and humanized antibodies (huAb) 0301.1, 0301.2, 0302.3, 0301.4, 0301.5, and 0301.6 (h0301-L0H0, h0301-L0H1, h0301-L0H2, h0301-L1H0, h0301-L1H1, and h0301-L1H2, respectively). FIG. 4B shows binding curves for parental cAb 0302 and humanized antibodies (huAb) 0302.1, 0302.2, 0302.3, 0302.4, 0302.5, and 0302.6 (h0302-L0H1, h0302-L1H1, h0302-L2H1, h0302-L0H2, h0302-L1H2, and h0302-L2H2, respectively). FIG. 4C shows binding curves for parental cAb 0311 and humanized antibodies (huAb) 0311.1, 0311.2, 0311.3, and 0311.4 (h0311-L0H1, h0311-L1H1, h0311-L0H2, and h0311-L1H2, respectively).

FIG. 5A shows binding curves for parental cAb 0301 and humanized antibodies (huAb) 0301.1, 0301.2, 0302.3, 0301.4, 0301.5, and 0301.6 (h0301-L0H0, h0301-L0H1, h0301-L0H2, h0301-L1H0, h0301-L1H1, and h0301-L1H2, respectively). FIG. 5B shows binding curves for parental cAb 0302 and humanized antibodies (huAb) 0302.1, 0302.2, 0302.3, 0302.4, 0302.5, and 0302.6 (h0302-L0H1, h0302-L1H1, h0302-L2H1, h0302-L0H2, h0302-L1H2, and h0302-L2H2, respectively). FIG. 5C shows binding curves for parental cAb 0311 and humanized antibodies (huAb) 0311.1, 0311.2, 0311.3, and 0311.4 (h0311-L0H1, h0311-L1H1, h0311-L0H2, and h0311-L1H2, respectively).

FIG. 6A shows blocking curves for parental cAb 0301 and humanized antibodies (huAb) 0301.1, 0301.2, 0302.3, 0301.4, 0301.5, and 0301.6 (h0301-L0H0, h0301-L0H1, h0301-L0H2, h0301-L1H0, h0301-L1H1, and h0301-L1H2, respectively). FIG. 6B shows blocking curves for parental cAb 0302 and humanized antibodies (huAb) 0302.1, 0302.2, 0302.3, 0302.4, 0302.5, and 0302.6 (h0302-L0H1, h0302-L1H1, h0302-L2H1, h0302-L0H2, h0302-L1H2, and h0302-L2H2, respectively). FIG. 6C shows blocking curves for parental cAb 0311 and humanized antibodies (huAb) 0311.1, 0311.2, 0311.3, and 0311.4 (h0311-L0H1, h0311-L1H1, h0311-L0H2, and h0311-L1H2, respectively).

FIG. 7A shows blocking curves for parental cAb 0301 and humanized antibodies (huAb) 0301.1, 0301.2, 0302.3, 0301.4, 0301.5, and 0301.6 (h0301-L0H0, h0301-L0H1, h0301-L0H2, h0301-L1H0, h0301-L1H1, and h0301-L1H2, respectively). FIG. 7B shows blocking curves for parental cAb 0302 and humanized antibodies (huAb) 0302.1, 0302.2, 0302.3, 0302.4, 0302.5, and 0302.6 (h0302-L0H1, h0302-L1H1, h0302-L2H1, h0302-L0H2, h0302-L1H2, and h0302-L2H2, respectively). FIG. 7C shows blocking curves for parental cAb 0311 and humanized antibodies (huAb) 0311.1, 0311.2, 0311.3, and 0311.4 (h0311-L0H1, h0311-L1H1, h0311-L0H2, and h0311-L1H2, respectively).

FIG. 8A shows blocking curves for parental cAb 0301 and humanized antibodies (huAb) 0301.1, 0301.2, 0302.3, 0301.4, 0301.5, and 0301.6 (h0301-L0H0, h0301-L0H1, h0301-L0H2, h0301-L1H0, h0301-L1H1, and h0301-L1H2, respectively). FIG. 8B shows blocking curves for parental cAb 0302 and humanized antibodies (huAb) 0302.1, 0302.2, 0302.3, 0302.4, 0302.5, and 0302.6 (h0302-L0H1, h0302-L1H1, h0302-L2H1, h0302-L0H2, h0302-L1H2, and h0302-L2H2, respectively). FIG. 8C shows blocking curves for parental cAb 0311 and humanized antibodies (huAb) 0311.1, 0311.2, 0311.3, and 0311.4 (h0311-L0H1, h0311-L1H1, h0311-L0H2, and h0311-L1H2, respectively).

FIG. 9A shows blocking curves for parental cAb 0301 and humanized antibodies (huAb) 0301.1, 0301.2, 0302.3, 0301.4, 0301.5, and 0301.6 (h0301-L0H0, h0301-L0H1, h0301-L0H2, h0301-L1H0, h0301-L1H1, and h0301-L1H2, respectively). FIG. 9B shows blocking curves for parental cAb 0302 and humanized antibodies (huAb) 0302.1, 0302.2, 0302.3, 0302.4, 0302.5, and 0302.6 (h0302-L0H1, h0302-L1H1, h0302-L2H1, h0302-L0H2, h0302-L1H2, and h0302-L2H2, respectively). FIG. 9C shows blocking curves for parental cAb 0311 and humanized antibodies (huAb) 0311.1, 0311.2, 0311.3, and 0311.4 (h0311-L0H1, h0311-L1H1, h0311-L0H2, and h0311-L1H2, respectively).

DETAILED DESCRIPTION

Figure 3:
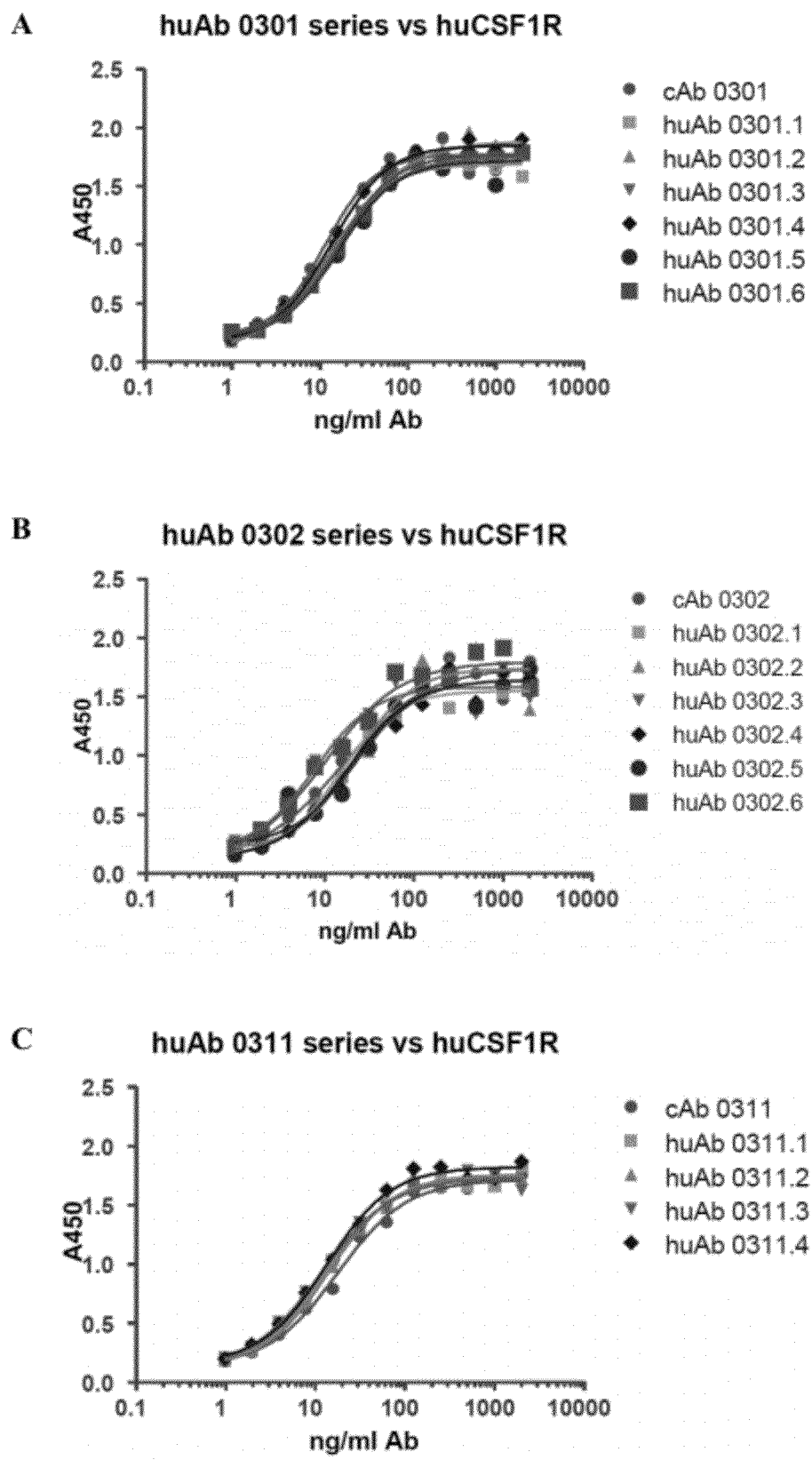
FIGS. 3A-C show binding curves for certain humanized antibodies binding to human CSF1R ECD, as described in Example 5.

Methods of treating diseases comprising administering novel antibodies to CSF1R are provided. All of the antibodies have binding affinities for human CSF1R ECD of less than 2 nM, and all but two of the humanized antibodies have sub-nanomolar binding affinities for human CSF1R ECD. Further, the new antibodies block binding of both CSF1 and IL34 to human CSF1R, and inhibit ligand-induced phosphorylation of human CSF1R. Many of the new antibodies also block binding of CSF1 and IL34 to cynomolgus CSF1R, which facilitates in vivo experiments to support the development of anti-CSF1R antibody therapeutics. The new antibodies are therefore well suited for therapeutic use in human diseases, including, but not limited to, cancer, autoimmune diseases, and inflammatory conditions.

The section headings used herein are for organizational purposes only and are not to be construed as limiting the subject matter described.

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Exemplary techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (2nd ed., Cold Spring Harbor Laboratory Press, Cold Spring Harbor, N.Y. (1989)), among other places. In addition, exemplary techniques for chemical syntheses, chemical analyses, pharmaceutical preparation, formulation, and delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "CSF1R" refers herein to the full-length CSF1R, which includes the N-terminal ECD, the transmembrane domain, and the intracellular tyrosine kinase domain, with or without an N-terminal leader sequence. In some embodiments, the CSF1R is a human CSF1R having the amino acid sequence of SEQ ID NO: 1 or SEQ ID NO: 2.

The term "CSF1R extracellular domain" ("CSF1R ECD") as used herein refers to a CSF1R polypeptide that lacks the intracellular and transmembrane domains. CSF1R ECDs include the full-length CSF1R ECD and CSF1R ECD fragments that are capable of binding CSF1R and/or IL34. The human full-length CSF1R ECD is defined herein as comprising either amino acids 1 to 512 (i.e., including the leader sequence) or amino acids 20 to 512 (i.e., lacking the leader sequence) of SEQ ID NO: 2. In some embodiments, a human CSF1R ECD fragment comprises amino acids 20 to 506 of SEQ ID NO: 2 (see SEQ ID NO:5). In some embodiments, a human CSF1R fragment ends at amino acid 507, 508, 509, 510, or 511. In some embodiments, a cynoCSF1R ECD comprises the sequence of SEQ ID NO: 7 (with leader sequence) or amino acids 20 to 506 of SEQ ID NO: 7 (without leader sequence).

The term "antibody" as used herein refers to a molecule comprising at least complementarity-determining region (CDR)1, CDR2, and CDR3 of a heavy chain and at least CDR1, CDR2, and CDR3 of a light chain, wherein the molecule is capable of binding to antigen. The term antibody includes, but is not limited to, fragments that are capable of binding antigen, such as Fv, single-chain Fv (scFv), Fab, Fab', and (Fab')$_2$. The term antibody also includes, but is not limited to, chimeric antibodies, humanized antibodies, and antibodies of various species such as mouse, human, cynomolgus monkey, etc.

In some embodiments, an antibody comprises a heavy chain variable region and a light chain variable region. In some embodiments, an antibody comprises at least one heavy chain comprising a heavy chain variable region and at least a portion of a heavy chain constant region, and at least one light chain comprising a light chain variable region and at least a portion of a light chain constant region. In some embodiments, an antibody comprises two heavy chains, wherein each heavy chain comprises a heavy chain variable region and at least a portion of a heavy chain constant region, and two light chains, wherein each light chain comprises a light chain variable region and at least a portion of a light chain constant region. As used herein, a single-chain Fv (scFv), or any other antibody that comprises, for example, a single polypeptide chain comprising all six CDRs (three heavy chain CDRs and three light chain CDRs) is considered to have a heavy chain and a light chain. In some such embodiments, the heavy chain is the region of the antibody that comprises the three heavy chain CDRs and the light chain in the region of the antibody that comprises the three light chain CDRs.

Figure 1A:
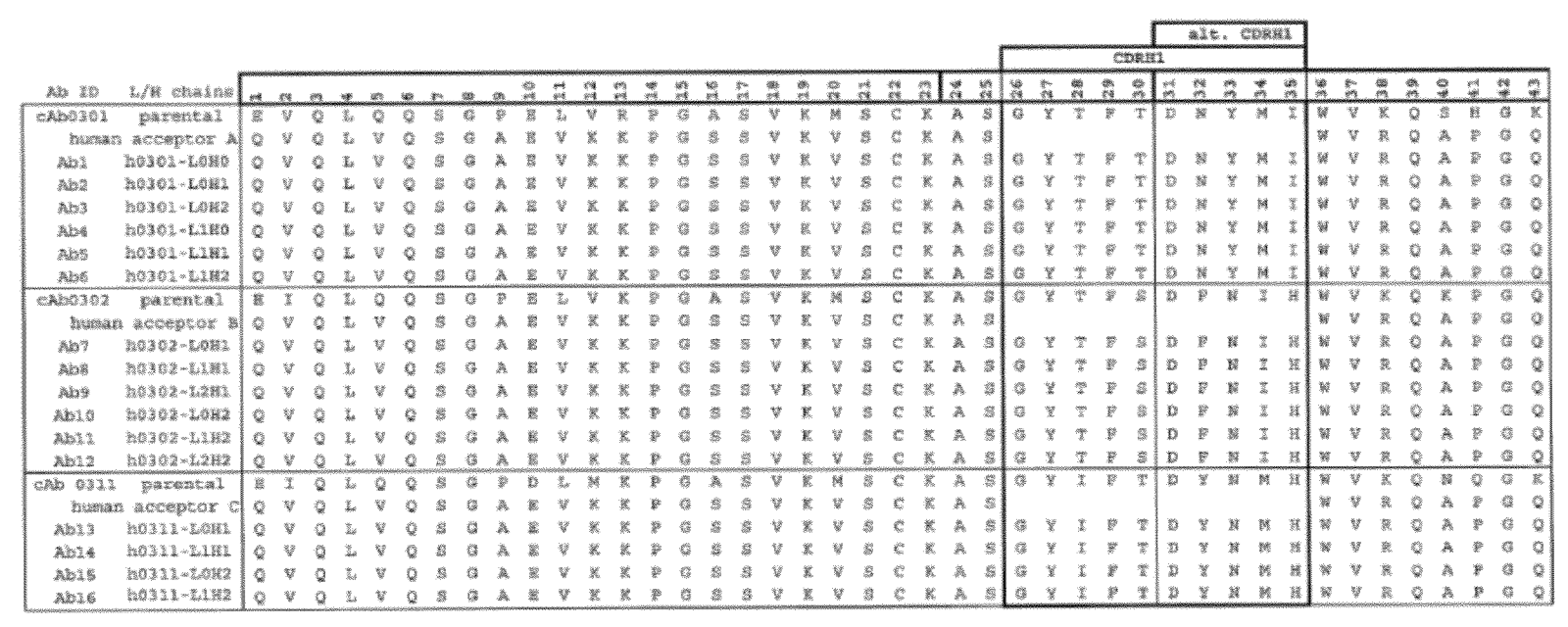

The term "heavy chain variable region" as used herein refers to a region comprising heavy chain CDR1, framework (FR)2, CDR2, FR3, and CDR3. In some embodiments, a heavy chain variable region also comprises at least a portion of an FR1 and/or at least a portion of an FR4. In some embodiments, a heavy chain CDR1 corresponds to Kabat residues 26 to 35; a heavy chain CDR2 corresponds to Kabat residues 50 to 65; and a heavy chain CDR3 corresponds to Kabat residues 95 to 102. See, e.g., Kabat Sequences of Proteins of Immunological Interest (1987 and 1991, NIH, Bethesda, Md.); and FIG. 1. In some embodiments, a heavy chain CDR1 corresponds to Kabat residues 31 to 35; a heavy chain CDR2 corresponds to Kabat residues 50 to 65; and a heavy chain CDR3 corresponds to Kabat residues 95 to 102. See id.

The term "heavy chain constant region" as used herein refers to a region comprising at least three heavy chain constant domains, $C_H1$, $C_H2$, and $C_H3$. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising an μ constant region is an IgM antibody, and an antibody comprising an ε constant region is an IgE antibody. Certain isotypes can be further subdivided into subclasses. For example, IgG antibodies include, but are not limited to, IgG1 (comprising a $\gamma_1$ constant region), IgG2 (comprising a $\gamma_2$ constant region), IgG3 (comprising a $\gamma_3$ constant region), and IgG4 (comprising a $\gamma_4$ constant region) antibodies; IgA antibodies include, but are not limited to, IgA1 (comprising an $\alpha_t$ constant region) and IgA2 (comprising an $\alpha_2$ constant region) antibodies; and IgM antibodies include, but are not limited to, IgM1 and IgM2.

In some embodiments, a heavy chain constant region comprises one or more mutations (or substitutions), additions, or deletions that confer a desired characteristic on the antibody. A nonlimiting exemplary mutation is the S241P mutation in the IgG4 hinge region (between constant domains $C_H1$ and $C_H2$), which alters the IgG4 motif CPSCP to CPPCP, which is similar to the corresponding motif in IgG1. That mutation, in some embodiments, results in a more stable IgG4 antibody. See, e.g., Angal et al., *Mol. Immunol.* 30: 105-108 (1993); Bloom et al., *Prot. Sci.* 6: 407-415 (1997); Schuurman et al., *Mol. Immunol.* 38: 1-8 (2001).

The term "heavy chain" as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence.

The term "light chain variable region" as used herein refers to a region comprising light chain CDR1, framework (FR)2, CDR2, FR3, and CDR3. In some embodiments, a light chain variable region also comprises an FR1 and/or an FR4. In some embodiments, a light chain CDR1 corresponds to Kabat residues 24 to 34; a light chain CDR2 corresponds to Kabat residues 50 to 56; and a light chain CDR3 corresponds to Kabat residues 89 to 97. See, e.g., Kabat Sequences of Proteins of Immunological Interest (1987 and 1991, NIH, Bethesda, Md.); and FIG. 1.

The term "light chain constant region" as used herein refers to a region comprising a light chain constant domain, $C_L$. Nonlimiting exemplary light chain constant regions include λ and κ.

The term "light chain" as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

A "chimeric antibody" as used herein refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, all of the variable regions of a chimeric antibody are from a first species and all of the constant regions of the chimeric antibody are from a second species.

A "humanized antibody" as used herein refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is an Fab, an scFv, a $(Fab')_2$, etc.

A "CDR-grafted antibody" as used herein refers to a humanized antibody in which the complementarity determining regions (CDRs) of a first (non-human) species have been grafted onto the framework regions (FRs) of a second (human) species.

A "human antibody" as used herein refers to antibodies produced in humans, antibodies produced in non-human animals that comprise human immunoglobulin genes, such as XenoMouse®, and antibodies selected using in vitro methods, such as phage display, wherein the antibody repertoire is based on a human immunoglobulin sequences.

The term "leader sequence" refers to a sequence of amino acid residues located at the N terminus of a polypeptide that facilitates secretion of a polypeptide from a mammalian cell. A leader sequence may be cleaved upon export of the polypeptide from the mammalian cell, forming a mature protein. Leader sequences may be natural or synthetic, and they may be heterologous or homologous to the protein to which they are attached. Exemplary leader sequences include, but are not limited to, antibody leader sequences, such as, for example, the amino acid sequences of SEQ ID NOs.: 3 and 4, which correspond to human light and heavy chain leader sequences, respectively. Nonlimiting exemplary leader sequences also include leader sequences from heterologous proteins. In some embodiments, an antibody lacks a leader sequence. In some embodiments, an antibody comprises at least one leader sequence, which may be selected from native antibody leader sequences and heterologous leader sequences.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E and DG44 cells, respectively.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The terms "subject" and "patient" are used interchangeably herein to refer to a human. In some embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided.

The term "rheumatoid arthritis" ("RA") refers to a chronic autoimmune disease characterized primarily by inflammation of the lining (synovium) of the joints, which can lead to joint damage, resulting in chronic pain, loss of function, and disability. Because RA can affect multiple organs of the body, including skin, lungs, and eyes, it is referred to as a systemic illness.

The term "multiple sclerosis" ("MS") refers to the chronic, autoimmune, demyelinating disease of the CNS in which the body generates antibodies and white blood cells against the cells that produce the myelin sheath. "Demyelination" occurs when the myelin sheath becomes inflamed, injured, and detaches from the nerve fiber.

The term "cancer" refers to a proliferative disorder associated with uncontrolled cell proliferation, unrestrained cell growth, and decreased cell death/apoptosis. Cancer includes, but is not limited to, breast cancer, prostate cancer, lung cancer, kidney cancer, thyroid cancer, esophageal cancer, melanoma, follicular lymphomas, uveal melanoma, brain cancer, head and neck cancer, pulmonary adenocarcinoma, including, but not limited to, colon cancer, cardiac tumors, pancreatic cancer, retinoblastoma, glioblastoma, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, Kaposi's sarcoma, ovarian cancer, leukemia (including acute leukemias (for example, acute lymphocytic leukemia, acute myelocytic leukemia, including myeloblastic, promyelocytic, myelomonocytic, monocytic, and erythroleukemia)) and chronic leukemias (for example, chronic myelocytic (granulocytic) leukemia and chronic lymphocytic leukemia), myelodysplastic syndrome polycythemia vera, lymphomas (for example, Hodgkin's disease, non-Hodgkin's disease), multiple myeloma, Waldenstrom's macroglobulinemia, heavy chain diseases, and solid tumors including, but not limited to, sarcomas and carcinomas such as fibrosarcoma, myxosarcoma, liposarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, endometrial cancer, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, and menangioma. The terms "metastasis" and "cancer metastasis" are used interchangeably herein to refer to the ability of a cancer cell to spread to other tissues. For example, "metastasis to bone" refers to the ability of certain types of cancer including, but not limited to, breast, prostate, lung, kidney, thyroid, and melanoma, to metastasize to bone.

The term "osteolytic disorders" is used herein to refer to any condition that is caused by an increase in the activity of osteoclasts, which are cells responsible for bone resorption. The terms "osteolysis" and "osteolytic bone loss" may be used interchangeably to refer to osteoclast-mediated bone resorption or bone loss associated with an osteolytic disorder. Osteolytic disorders may occur in subjects with a predisposition to develop an osteolytic disorder, or they may occur in subjects with a disease that leads to or contributes to an osteolytic disorder by stimulating osteoclast activity. In exemplary embodiments of the present invention, the osteolytic disorder may include osteolytic bone loss and cancer metastasis-induced osteolytic bone loss. In further exemplary embodiments of the present invention, the osteolytic bone disorder includes metabolic bone disease, including endocrinopathies, such as hypercortisolism, hypogonadism, primary or secondary hyperparathyroidism, and hyperthyroidism; dietary deficiency, including rickets, osteomalacia, scurvy, and malnutrition; osteoporosis; drug use, including glucocorticoids (glucocorticoid-induced osteoporosis), heparin, and alcohol; chronic disease, including malabsorption syndromes; chronic renal failure, including renal osteodystrophy; chronic liver disease, including hepatic osteodystrophy; inherited disease, including osteogenesis imperfecta and homocystinuria; and bone inflammation associated with arthritis, rheumatoid arthritis, psoriatic arthritis, fibrous dysplasia, periodontal disease, and Paget's disease.

The terms "metastasis-induced osteolytic bone loss," and "cancer metastasis-induced osteolytic bone loss," are used interchangeably herein to refer to osteolysis or osteolytic bone loss resulting from cancer cell metastasis to bone. The term "cancer metastasis-induced osteoclast activation" is used herein to refer to the ability of cancer cells that have metastasized to bone to induce the activation of osteoclasts.

The term "tumor" is used herein to refer to a group of cells that exhibit abnormally high levels of proliferation and growth. A tumor may be benign, pre-malignant, or malignant; malignant tumor cells are cancerous. Tumor cells may be solid tumor cells or leukemic tumor cells. The term "tumor growth" is used herein to refer to proliferation or growth by a cell or cells that comprise a tumor that leads to a corresponding increase in the size of the tumor. The term "CSFIR-dependent tumor growth" is used herein to refer to the requirement of a tumor cell or cells for CSFIR-mediated function(s) in order for the tumor cell or cells to proliferate or grow.

"Treatment," as used herein, covers any administration or application of a therapeutic for disease in a mammal, including a human, and includes inhibiting the disease or progression of the disease, inhibiting or slowing the disease or its progression, arresting its development, partially or fully relieving the disease, or curing the disease, for example, by causing regression, or restoring or repairing a lost, missing, or defective function; or stimulating an inefficient process.

The terms "inhibition" or "inhibit" refer to a decrease or cessation of any phenotypic characteristic or to the decrease or cessation in the incidence, degree, or likelihood of that characteristic.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

Anti-CSF1R Antibodies

The present inventors have invented a new set of antibodies directed against CSF1R. Anti-CSF1R antibodies include, but are not limited to, humanized antibodies, chimeric antibodies, mouse antibodies, human antibodies, and antibodies comprising the heavy chain and/or light chain CDRs discussed herein.

Exemplary Humanized Antibodies

In some embodiments, humanized antibodies that bind CSF1R are provided. Humanized antibodies are useful as therapeutic molecules because humanized antibodies reduce or eliminate the human immune response to non-human antibodies (such as the human anti-mouse antibody (HAMA) response), which can result in an immune response to an antibody therapeutic, and decreased effectiveness of the therapeutic.

Nonlimiting exemplary humanized antibodies include Ab1 through Ab16, described herein. Nonlimiting exemplary humanized antibodies also include antibodies comprising a heavy chain variable region of an antibody selected from Ab1 to Ab16 and/or a light chain variable region of an antibody selected from Ab1 to Ab16. Nonlimiting exemplary humanized antibodies include antibodies comprising a heavy chain variable region selected from SEQ ID NOs: 39 to 45 and/or a light chain variable region selected from SEQ ID NOs: 46 to 52. Exemplary humanized antibodies also include, but are not limited to, humanized antibodies comprising heavy chain CDR1, CDR2, and CDR3, and/or light chain CDR1, CDR2, and CDR3 of an antibody selected from 0301, 0302, and 0311.

In some embodiments, a humanized anti-CSF1R antibody comprises heavy chain CDR1, CDR2, and CDR3 and/or a light chain CDR1, CDR2, and CDR3 of an antibody selected from 0301, 0302, and 0311. Nonlimiting exemplary humanized anti-CSF1R antibodies include antibodies comprising sets of heavy chain CDR1, CDR2, and CDR3 selected from: SEQ ID NOs: 15, 16, and 17; SEQ ID NOs: 21, 22, and 23; and SEQ ID NOs: 27, 28, and 29. Nonlimiting exemplary humanized anti-CSF1R antibodies also include antibodies comprising sets of light chain CDR1, CDR2, and CDR3 selected from: SEQ ID NOs: 18, 19, and 20; SEQ ID NOs: 24, 25, and 26; and SEQ ID NOs: 30, 31, and 32.

Nonlimiting exemplary humanized anti-CSF1R antibodies include antibodies comprising the sets of heavy chain CDR1, CDR2, and CDR3, and light chain CDR1, CDR2, and CDR3 in Table 1 (SEQ ID NOs shown; see Table 8 for sequences). Each row of Table 1 shows the heavy chain CDR1, CDR2, and CDR3, and light chain CDR1, CDR2, and CDR3 of an exemplary antibody.

TABLE 1

Heavy chain and light chain CDRs

| Heavy chain | | | Light chain | | |
|---|---|---|---|---|---|
| CDR1 SEQ ID | CDR2 SEQ ID | CDR3 SEQ ID | CDR1 SEQ ID | CDR2 SEQ ID | CDR3 SEQ ID |
| 15 | 16 | 17 | 18 | 19 | 20 |
| 21 | 22 | 23 | 24 | 25 | 26 |
| 27 | 28 | 29 | 30 | 31 | 32 |

Further Exemplary Humanized Antibodies

In some embodiments, a humanized anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45, and wherein the antibody binds CSF1R. In some embodiments, a humanized anti-CSF1R antibody comprises a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52, wherein the antibody binds CSF1R. In some embodiments, a humanized anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45; and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52; wherein the antibody binds CSF1R.

As used herein, whether a particular polypeptide is, for example, at least 95% identical to an amino acid sequence can be determined using, e.g., a computer program. When determining whether a particular sequence is, for example, 95% identical to a reference sequence, the percentage of identity is calculated over the full length of the reference amino acid sequence.

In some embodiments, a humanized anti-CSF1R antibody comprises at least one of the CDRs discussed herein. That is, in some embodiments, a humanized anti-CSF1R antibody comprises at least one CDR selected from a heavy chain CDR1 discussed herein, a heavy chain CDR2 discussed herein, a heavy chain CDR3 discussed herein, a light chain CDR1 discussed herein, a light chain CDR2 discussed herein, and a light chain CDR3 discussed herein. Further, in some embodiments, a humanized anti-CSF1R antibody comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the antibody comprising the mutated CDR.

Exemplary humanized anti-CSF1R antibodies also include antibodies that compete for binding to CSF1R with an antibody described herein. Thus, in some embodiments, a humanized anti-CSF1R antibody is provided that competes for binding to CSF1R with an antibody selected from Fabs 0301, 0302, and 0311; and bivalent (i.e., having two heavy chains and two light chains) antibody versions of those Fabs.

Exemplary Humanized Antibody Constant Regions

In some embodiments, a humanized antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, a humanized antibody described herein comprises a human IgG constant region. In some embodiments, a humanized antibody described herein comprises a human IgG4 heavy chain constant region. In some such embodiments, a humanized antibody described herein comprises an S241P mutation in the human IgG4 constant region. In some embodiments, a humanized antibody described herein comprises a human IgG4 constant region and a human κ light chain.

The choice of heavy chain constant region can determine whether or not an antibody will have effector function in vivo. Such effector function, in some embodiments, includes antibody-dependent cell-mediated cytotoxicity (ADCC) and/or complement-dependent cytotoxicity (CDC), and can result in killing of the cell to which the antibody is bound. In some methods of treatment, including methods of treating some cancers, cell killing may be desirable, for example, when the antibody binds to a cell that supports the maintenance or growth of the tumor. Exemplary cells that may support the maintenance or growth of a tumor include, but are not limited to, tumor cells themselves, cells that aid in the recruitment of vasculature to the tumor, and cells that provide ligands, growth factors, or counter-receptors that support or promote tumour growth or tumour survival. In some embodiments, when effector function is desirable, an anti-CSF1R antibody comprising a human IgG1 heavy chain or a human IgG3 heavy chain is selected.

In some methods of treatment, effector function may not be desirable. For example, in some embodiments, it may be desirable that antibodies used in the treatment of MS and/or RA and/or osteolysis do not have effector function. Thus, in some embodiments, anti-CSF1R antibodies developed for the treatment of cancer may not be suitable for use in treatment of MS and/or RA and/or osteolysis. Accordingly, in some embodiments, an anti-CSF1R antibody that lacks significant effector function is used in treatment of MS and/or RA and/or osteolysis. In some embodiments, an anti-CSF1R antibody for treatment of MS and/or RA and/or osteolysis comprises a human IgG4 or IgG2 heavy chain constant region. In some embodiments, an IgG4 constant region comprises an S241P mutation.

An antibody may be humanized by any method. Nonlimiting exemplary methods of humanization include methods described, e.g., in U.S. Pat. Nos. 5,530,101; 5,585,089; 5,693,761; 5,693,762; 6,180,370; Jones et al., *Nature* 321: 522-525 (1986); Riechmann et al., *Nature* 332: 323-27 (1988); Verhoeyen et al., Science 239: 1534-36 (1988); and U.S. Publication No. US 2009/0136500.

As noted above, a humanized antibody is an antibody in which at least one amino acid in a framework region of a non-human variable region has been replaced with the amino acid from the corresponding location in a human framework region. In some embodiments, at least two, at least three, at least four, at least five, at least six, at least seven, at least eight, at least nine, at least 10, at least 11, at least 12, at least 15, or at least 20 amino acids in the framework regions of a non-human variable region are replaced with an amino acid from one or more corresponding locations in one or more human framework regions.

In some embodiments, some of the corresponding human amino acids used for substitution are from the framework regions of different human immunoglobulin genes. That is, in some such embodiments, one or more of the non-human amino acids may be replaced with corresponding amino acids from a human framework region of a first human antibody or encoded by a first human immunoglobulin gene, one or more of the non-human amino acids may be replaced with corresponding amino acids from a human framework region of a second human antibody or encoded by a second human immunoglobulin gene, one or more of the non-human amino acids may be replaced with corresponding amino acids from a human framework region of a third human antibody or encoded by a third human immunoglobulin gene, etc. Further, in some embodiments, all of the corresponding human amino acids being used for substitution in a single framework region, for example, FR2, need not be from the same human framework. In some embodiments, however, all of the corresponding human amino acids being used for substitution are from the same human antibody or encoded by the same human immunoglobulin gene.

In some embodiments, an antibody is humanized by replacing one or more entire framework regions with corresponding human framework regions. In some embodiments, a human framework region is selected that has the highest level of homology to the non-human framework region being replaced. In some embodiments, such a humanized antibody is a CDR-grafted antibody.

In some embodiments, following CDR-grafting, one or more framework amino acids are changed back to the corresponding amino acid in a mouse framework region. Such "back mutations" are made, in some embodiments, to retain one or more mouse framework amino acids that appear to contribute to the structure of one or more of the CDRs and/or that may be involved in antigen contacts and/or appear to be involved in the overall structural integrity of the antibody. In some embodiments, ten or fewer, nine or fewer, eight or fewer, seven or fewer, six or fewer, five or fewer, four or fewer, three or fewer, two or fewer, one, or zero back mutations are made to the framework regions of an antibody following CDR grafting.

In some embodiments, a humanized antibody also comprises a human heavy chain constant region and/or a human light chain constant region.

Exemplary Chimeric Antibodies

In some embodiments, an anti-CSF1R antibody is a chimeric antibody. In some embodiments, an anti-CSF1R antibody comprises at least one non-human variable region and at least one human constant region. In some such embodiments, all of the variable regions of an anti-CSF1R antibody are non-human variable regions, and all of the constant regions of an anti-CSF1R antibody are human constant regions. In some embodiments, one or more variable regions of a chimeric antibody are mouse variable regions. The human constant region of a chimeric antibody need not be of the same isotype as the non-human constant region, if any, it replaces. Chimeric antibodies are discussed, e.g., in U.S. Pat. No. 4,816, 567; and Morrison et al. *Proc. Natl. Acad. Sci. USA* 81: 6851-55 (1984).

Nonlimiting exemplary chimeric antibodies include chimeric antibodies comprising the heavy and/or light chain variable regions of an antibody selected from 0301, 0302, and 0311. Additional nonlimiting exemplary chimeric antibodies include chimeric antibodies comprising heavy chain CDR1, CDR2, and CDR3, and/or light chain CDR1, CDR2, and CDR3 of an antibody selected from 0301, 0302, and 0311.

Nonlimiting exemplary chimeric anti-CSF1R antibodies include antibodies comprising the following pairs of heavy and light chain variable regions: SEQ ID NOs: 9 and 10; SEQ ID NOs: 11 and 12; and SEQ ID NOs: 13 and 14.

Nonlimiting exemplary anti-CSF1R antibodies include antibodies comprising a set of heavy chain CDR1, CDR2, and CDR3, and light chain CDR1, CDR2, and CDR3 shown above in Table 1.

Further Exemplary Chimeric Antibodies

In some embodiments, a chimeric anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45, wherein the antibody binds CSF1R. In some embodiments, a chimeric anti-CSF1R antibody comprises a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52, wherein the antibody binds CSF1R. In some embodiments, a chimeric anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45; and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52; wherein the antibody binds CSF1R.

In some embodiments, a chimeric anti-CSF1R antibody comprises at least one of the CDRs discussed herein. That is, in some embodiments, a chimeric anti-CSF1R antibody comprises at least one CDR selected from a heavy chain CDR1 discussed herein, a heavy chain CDR2 discussed herein, a heavy chain CDR3 discussed herein, a light chain CDR1 discussed herein, a light chain CDR2 discussed herein, and a light chain CDR3 discussed herein. Further, in some embodiments, a chimeric anti-CSF1R antibody comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the antibody comprising the mutated CDR.

Exemplary chimeric anti-CSF1R antibodies also include chimeric antibodies that compete for binding to CSF1R with an antibody described herein. Thus, in some embodiments, a chimeric anti-CSF1R antibody is provided that competes for binding to CSF1R with an antibody selected from Fabs 0301, 0302, and 0311; and bivalent (i.e., having two heavy chains and two light chains) antibody versions of those Fabs.

Exemplary Chimeric Antibody Constant Regions

In some embodiments, a chimeric antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, a chimeric antibody described herein comprises a human IgG constant region. In some embodiments, a chimeric antibody described herein comprises a human IgG4 heavy chain constant region. In some such embodiments, a chimeric antibody described herein comprises an S241P mutation in the human IgG4 constant region. In some embodiments, a chimeric antibody described herein comprises a human IgG4 constant region and a human κ light chain.

As noted above, whether or not effector function is desirable may depend on the particular method of treatment intended for an antibody. Thus, in some embodiments, when effector function is desirable, a chimeric anti-CSF1R antibody comprising a human IgG1 heavy chain constant region or a human IgG3 heavy chain constant region is selected. In some embodiments, when effector function is not desirable, a chimeric anti-CSF1R antibody comprising a human IgG4 or IgG2 heavy chain constant region is selected.

Exemplary Human Antibodies

Human antibodies can be made by any suitable method. Nonlimiting exemplary methods include making human antibodies in transgenic mice that comprise human immunoglobulin loci. See, e.g., Jakobovits et al., *Proc. Natl. Acad. Sci. USA* 90: 2551-55 (1993); Jakobovits et al., *Nature* 362: 255-8 (1993); Lonberg et al., *Nature* 368: 856-9 (1994); and U.S. Pat. Nos. 5,545,807; 6,713,610; 6,673,986; 6,162,963; 5,545, 807; 6,300,129; 6,255,458; 5,877,397; 5,874,299; and 5,545, 806.

Nonlimiting exemplary methods also include making human antibodies using phage display libraries. See, e.g., Hoogenboom et al., *J. Mol. Biol.* 227: 381-8 (1992); Marks et al., *J. Mol. Biol.* 222: 581-97 (1991); and PCT Publication No. WO 99/10494.

In some embodiments, a human anti-CSF1R antibody binds to a polypeptide having the sequence of SEQ ID NO: 1.

Exemplary human anti-CSF1R antibodies also include antibodies that compete for binding to CSF1R with an antibody described herein. Thus, in some embodiments, a human anti-CSF1R antibody is provided that competes for binding to CSF1R with an antibody selected from Fabs 0301, 0302, and 0311, and bivalent (i.e., having two heavy chains and two light chains) antibody versions of those Fabs.

In some embodiments, a human anti-CSF1R antibody comprises one or more human constant regions. In some embodiments, the human heavy chain constant region is of an isotype selected from IgA, IgG, and IgD. In some embodiments, the human light chain constant region is of an isotype selected from κ and λ. In some embodiments, a human antibody described herein comprises a human IgG constant region. In some embodiments, a human antibody described herein comprises a human IgG4 heavy chain constant region. In some such embodiments, a human antibody described herein comprises an S241P mutation in the human IgG4 constant region. In some embodiments, a human antibody described herein comprises a human IgG4 constant region and a human κ light chain.

In some embodiments, when effector function is desirable, a human anti-CSF1R antibody comprising a human IgG1 heavy chain constant region or a human IgG3 heavy chain constant region is selected. In some embodiments, when effector function is not desirable, a human anti-CSF1R antibody comprising a human IgG4 or IgG2 heavy chain constant region is selected.

Additional Exemplary Anti-CSF1R Antibodies

Exemplary anti-CSF1R antibodies also include, but are not limited to, mouse, humanized, human, chimeric, and engineered antibodies that comprise, for example, one or more of the CDR sequences described herein. In some embodiments, an anti-CSF1R antibody comprises a heavy chain variable region described herein. In some embodiments, an anti-CSF1R antibody comprises a light chain variable region described herein. In some embodiments, an anti-CSF1R antibody comprises a heavy chain variable region described herein and a light chain variable region described herein. In some embodiments, an anti-CSF1R antibody comprises heavy chain CDR1, CDR2, and CDR3 described herein. In some embodiments, an anti-CSF1R antibody comprises light chain CDR1, CDR2, and CDR3 described herein. In some embodiments, an anti-CSF1R antibody comprises heavy chain CDR1, CDR2, and CDR3 described herein and light chain CDR1, CDR2, and CDR3 described herein.

In some embodiments, an anti-CSF1R antibody comprises a heavy chain variable region of an antibody selected from Fabs 0301, 0302, and 0311. Nonlimiting exemplary anti-CSF1R antibodies also include antibodies comprising a heavy chain variable region of an antibody selected from humanized antibodies Ab1 to Ab16. Nonlimiting exemplary anti-CSF1R antibodies include antibodies comprising a heavy chain variable region comprising a sequence selected from SEQ ID NOs: 9, 11, 13, and 39 to 45.

In some embodiments, an anti-CSF1R antibody comprises a light chain variable region of an antibody selected from Fabs 0301, 0302, and 311. Nonlimiting exemplary anti-CSF1R antibodies also include antibodies comprising a light chain variable region of an antibody selected from humanized antibodies Ab1 to Ab16. Nonlimiting exemplary anti-CSF1R antibodies include antibodies comprising a light chain variable region comprising a sequence selected from SEQ ID NOs: 10, 12, 14, and 46 to 52.

In some embodiments, an anti-CSF1R antibody comprises a heavy chain variable region and a light chain variable region of an antibody selected from Fabs 0301, 0302, and 0311. Nonlimiting exemplary anti-CSF1R antibodies also include antibodies comprising a heavy chain variable region and a light chain variable region of an antibody selected from humanized antibodies Ab1 to Ab16. Nonlimiting exemplary anti-CSF1R antibodies include antibodies comprising the following pairs of heavy and light chain variable regions: SEQ ID NOs: 9 and 10; SEQ ID NOs: 11 and 12; and SEQ ID NOs: 13 and 14; SEQ ID NOs: 39 and 40; SEQ ID NOs: 41 and 42; SEQ ID NOs: 43 and 44; SEQ ID NOs: 45 and 46; SEQ ID NOs: 47 and 48; SEQ ID NOs: 49 and 50; and SEQ ID NOs: 51 and 52. Nonlimiting exemplary anti-CSF1R antibodies also include antibodies comprising the following pairs of heavy and light chains: SEQ ID NOs: 33 and 34; SEQ ID NOs: 35 and 36; and SEQ ID NOs: 37 and 38.

In some embodiments, an anti-CSF1R antibody comprises heavy chain CDR1, CDR2, and CDR3 of an antibody selected from Fabs 0301, 0302, and 0311. Nonlimiting exemplary anti-CSF1R antibodies include antibodies comprising sets of heavy chain CDR1, CDR2, and CDR3 selected from: SEQ ID NOs: 15, 16, and 17; SEQ ID NOs: 21, 22, and 23; and SEQ ID NOs: 27, 28, and 29.

In some embodiments, an anti-CSF1R antibody comprises light chain CDR1, CDR2, and CDR3 of an antibody selected from Fabs 0301, 0302, and 0311. Nonlimiting exemplary anti-CSF1R antibodies include antibodies comprising sets of light chain CDR1, CDR2, and CDR3 selected from: SEQ ID NOs: 18, 19, and 20; SEQ ID NOs: 24, 25, and 26; and SEQ ID NOs: 30, 31, and 32.

In some embodiments, an anti-CSF1R antibody comprises heavy chain CDR1, CDR2, and CDR3, and light chain CDR1, CDR2, and CDR3 of an antibody selected from Fabs 0301, 0302, and 0311.

Nonlimiting exemplary anti-CSF1R antibodies include antibodies comprising the sets of heavy chain CDR1, CDR2, and CDR3, and light chain CDR1, CDR2, and CDR3 shown above in Table 1.

Further Exemplary Antibodies

In some embodiments, an anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45, wherein the antibody binds CSF1R. In some embodiments, an anti-CSF1R antibody comprises a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52, wherein the antibody binds CSF1R. In some embodiments, an anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45; and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52; wherein the antibody binds CSF1R.

In some embodiments, an anti-CSF1R antibody comprises at least one of the CDRs discussed herein. That is, in some embodiments, an anti-CSF1R antibody comprises at least one CDR selected from a heavy chain CDR1 discussed herein, a heavy chain CDR2 discussed herein, a heavy chain CDR3 discussed herein, a light chain CDR1 discussed herein, a light chain CDR2 discussed herein, and a light chain CDR3 discussed herein. Further, in some embodiments, an anti-CSF1R antibody comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the antibody comprising the mutated CDR.

Exemplary anti-CSF1R antibodies also include antibodies that compete for binding to CSF1R with an antibody described herein. Thus, in some embodiments, an anti-CSF1R antibody is provided that competes for binding to CSF1R with an antibody selected from Fabs 0301, 0302, and 0311, and bivalent (i.e., having two heavy chains and two light chains) antibody versions of those Fabs.

Exemplary Antibody Constant Regions

In some embodiments, an antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, an antibody described herein comprises a human IgG constant region. In some embodiments, an antibody described herein comprises a human IgG4 heavy chain constant region. In some such embodiments, an antibody described herein comprises an S241P mutation in the human IgG4 constant region. In some embodiments, an antibody described herein comprises a human IgG4 constant region and a human κ light chain.

As noted above, whether or not effector function is desirable may depend on the particular method of treatment intended for an antibody. Thus, in some embodiments, when effector function is desirable, an anti-CSF1R antibody comprising a human IgG1 heavy chain constant region or a human IgG3 heavy chain constant region is selected. In some embodiments, when effector function is not desirable, an anti-CSF1R antibody comprising a human IgG4 or IgG2 heavy chain constant region is selected.

Exemplary Anti-CSF1R Heavy Chain Variable Regions

In some embodiments, anti-CSF1R antibody heavy chain variable regions are provided. In some embodiments, an anti-CSF1R antibody heavy chain variable region is a mouse variable region, a human variable region, or a humanized variable region.

An anti-CSF1R antibody heavy chain variable region comprises a heavy chain CDR1, FR2, CDR2, FR3, and CDR3. In some embodiments, an anti-CSF1R antibody heavy chain variable region further comprises a heavy chain FR1 and/or FR4. Nonlimiting exemplary heavy chain variable regions include, but are not limited to, heavy chain variable regions having an amino acid sequence selected from SEQ ID NOs: 9, 11, 13, and 39 to 45.

In some embodiments, an anti-CSF1R antibody heavy chain variable region comprises a CDR1 comprising a sequence selected from SEQ ID NOs: 15, 21, and 27.

In some embodiments, an anti-CSF1R antibody heavy chain variable region comprises a CDR2 comprising a sequence selected from SEQ ID NOs: 16, 22, and 28.

In some embodiments, an anti-CSF1R antibody heavy chain variable region comprises a CDR3 comprising a sequence selected from SEQ ID NOs: 17, 23, and 29.

Nonlimiting exemplary heavy chain variable regions include, but are not limited to, heavy chain variable regions comprising sets of CDR1, CDR2, and CDR3 selected from: SEQ ID NOs: 15, 16, and 17; SEQ ID NOs: 21, 22, and 23; and SEQ ID NOs: 27, 28, and 29.

In some embodiments, an anti-CSF1R antibody heavy chain comprises a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45, wherein the heavy chain, together with a light chain, is capable of forming an antibody that binds CSF1R.

In some embodiments, an anti-CSF1R antibody heavy chain comprises at least one of the CDRs discussed herein. That is, in some embodiments, an anti-CSF1R antibody heavy chain comprises at least one CDR selected from a heavy chain CDR1 discussed herein, a heavy chain CDR2 discussed herein, and a heavy chain CDR3 discussed herein. Further, in some embodiments, an anti-CSF1R antibody heavy chain comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the heavy chain comprising the mutated CDR.

In some embodiments, a heavy chain comprises a heavy chain constant region. In some embodiments, a heavy chain comprises a human heavy chain constant region. In some embodiments, the human heavy chain constant region is of an isotype selected from IgA, IgG, and IgD. In some embodiments, the human heavy chain constant region is an IgG constant region. In some embodiments, a heavy chain comprises a human IgG4 heavy chain constant region. In some such embodiments, the human IgG4 heavy chain constant region comprises an S241P mutation.

In some embodiments, when effector function is desirable, a heavy chain comprises a human IgG1 or IgG3 heavy chain constant region. In some embodiments, when effector function is less desirable, a heavy chain comprises a human IgG4 or IgG2 heavy chain constant region.

Exemplary Anti-CSF1R Light Chain Variable Regions

In some embodiments, anti-CSF1R antibody light chain variable regions are provided. In some embodiments, an anti-CSF1R antibody light chain variable region is a mouse variable region, a human variable region, or a humanized variable region.

An anti-CSF1R antibody light chain variable region comprises a light chain CDR1, FR2, CDR2, FR3, and CDR3. In some embodiments, an anti-CSF1R antibody light chain variable region further comprises a light chain FR1 and/or FR4. Nonlimiting exemplary light chain variable regions include light chain variable regions having an amino acid sequence selected from SEQ ID NOs: 10, 12, 14, and 46 to 52.

In some embodiments, an anti-CSF1R antibody light chain variable region comprises a CDR1 comprising a sequence selected from SEQ ID NOs: 18, 24 and 30.

In some embodiments, an anti-CSF1R antibody light chain variable region comprises a CDR2 comprising a sequence selected from SEQ ID NOs: 19, 25, and 31.

In some embodiments, an anti-CSF1R antibody light chain variable region comprises a CDR3 comprising a sequence selected from SEQ ID NOs: 20, 26, and 32.

Nonlimiting exemplary light chain variable regions include, but are not limited to, light chain variable regions comprising sets of CDR1, CDR2, and CDR3 selected from:

SEQ ID NOs: 18, 19, and 20; SEQ ID NOs: 24, 25, and 26; and SEQ ID NOs: 30, 31, and 32.

In some embodiments, an anti-CSF1R antibody light chain comprises a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52, wherein the light chain, together with a heavy chain, is capable of forming an antibody that binds CSF1R.

In some embodiments, an anti-CSF1R antibody light chain comprises at least one of the CDRs discussed herein. That is, in some embodiments, an anti-CSF1R antibody light chain comprises at least one CDR selected from a light chain CDR1 discussed herein, a light chain CDR2 discussed herein, and a light chain CDR3 discussed herein. Further, in some embodiments, an anti-CSF1R antibody light chain comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the light chain comprising the mutated CDR.

In some embodiments, a light chain comprises a human light chain constant region. In some embodiments, a human light chain constant region is selected from a human κ and a human λ light chain constant region.

Exemplary Additional CSF1R Binding Molecules

In some embodiments, additional molecules that bind CSF1R are provided. Such molecules include, but are not limited to, non-canonical scaffolds, such as anti-calins, adnectins, ankyrin repeats, etc. See, e.g., Hosse et al., *Prot. Sci.* 15:14 (2006); Fiedler, M. and Skerra, A., "Non-Antibody Scaffolds," pp. 467-499 in Handbook of Therapeutic Antibodies, Dubel, S., ed., Wiley-VCH, Weinheim, Germany, 2007.

Exemplary Properties of Anti-CSF1R Antibodies

In some embodiments, an antibody having a structure described above binds to the CSF1R with a binding affinity ($K_D$) of less than 1 nM, blocks binding of CSF1 and/or IL34 to CSF1R, and inhibits CSF1R phosphorylation induced by CSF1 and/or IL34.

In some embodiments, an anti-CSF1R antibody binds to the extracellular domain of CSF1R(CSF1R-ECD). In some embodiments, an anti-CSF1R antibody has a binding affinity ($K_D$) for CSF1R of less than 1 nM, less than 0.5 nM, less than 0.1 nM, or less than 0.05 nM. In some embodiments, an anti-CSF1R antibody has a $K_D$ of between 0.01 and 1 nM, between 0.01 and 0.5 nM, between 0.01 and 0.1 nM, between 0.01 and 0.05 nM, or between 0.02 and 0.05 nM.

In some embodiments, an anti-CSF1R antibody blocks ligand binding to CSF1R. In some embodiments, an anti-CSF1R antibody blocks binding of CSF1 to CSF1R. In some embodiments, an anti-CSF1R antibody blocks binding of IL34 to CSF1R. In some embodiments, an anti-CSF1R antibody blocks binding of both CSF1 and IL34 to CSF1R. In some embodiments, an antibody that blocks ligand binding binds to the extracellular domain of CSF1R. An antibody is considered to "block ligand binding to CSF1R" when it reduces the amount of detectable binding of a ligand to CSF1R by at least 50%, using the assay described in Example 7. In some embodiments, an antibody reduces the amount of detectable binding of a ligand to CSF1R by at least 60%, at least 70%, at least 80%, or at least 90%, using the assay described in Example 7. In some such embodiments, the antibody is said to block ligand binding by at least 50%, at least 60%, at least 70%, etc.

In some embodiments, an anti-CSF1R antibody inhibits ligand-induced CSF1R phosphorylation. In some embodiments, an anti-CSF1R antibody inhibits CSF1-induced CSF1R phosphorylation. In some embodiments, an anti-CSF1R antibody inhibits IL34-induced CSF1R phosphorylation. In some embodiments, an anti-CSF1R antibody inhibits both CSF1-induced and IL34-induced CSF1R phosphorylation. An antibody is considered to "inhibit ligand-induced CSF1R phosphorylation" when it reduces the amount of detectable ligand-induced CSF1R phosphorylation by at least 50%, using the assay described in Example 6. In some embodiments, an antibody reduces the amount of detectable ligand-induced CSF1R phosphorylation by at least 60%, at least 70%, at least 80%, or at least 90%, using the assay described in Example 6. In some such embodiments, the antibody is said to inhibit ligand-induced CSF1R phosphorylation by at least at least 50%, at least 60%, at least 70%, etc.

In some embodiments, an antibody inhibits monocyte proliferation and/or survival responses in the presence of CSF1 and/or IL34. An antibody is considered to "inhibit monocyte proliferation and/or survival responses" when it reduces the amount of monocyte proliferation and/or survival responses in the presence of CSF1 and/or IL34 by at least 50%, using the assay described in Example 10. In some embodiments, an antibody reduces the amount of monocyte proliferation and/or survival responses in the presence of CSF1 and/or IL34 by at least 60%, at least 70%, at least 80%, or at least 90%, using the assay described in Example 10. In some such embodiments, the antibody is said to inhibit monocyte proliferation and/or survival responses by at least at least 50%, at least 60%, at least 70%, etc.

Exemplary Antibody Conjugates

In some embodiments, an anti-CSF1R antibody is conjugated to a label and/or a cytotoxic agent. As used herein, a label is a moiety that facilitates detection of the antibody and/or facilitates detection of a molecule to which the antibody binds. Nonlimiting exemplary labels include, but are not limited to, radioisotopes, fluorescent groups, enzymatic groups, chemiluminescent groups, biotin, epitope tags, metal-binding tags, etc. One skilled in the art can select a suitable label according to the intended application.

As used herein, a cytotoxic agent is a moiety that reduces the proliferative capacity of one or more cells. A cell has reduced proliferative capacity when the cell becomes less able to proliferate, for example, because the cell undergoes apoptosis or otherwise dies, the cell fails to proceed through the cell cycle and/or fails to divide, the cell differentiates, etc. Nonlimiting exemplary cytotoxic agents include, but are not limited to, radioisotopes, toxins, and chemotherapeutic agents. One skilled in the art can select a suitable cytotoxic according to the intended application.

In some embodiments, a label and/or a cytotoxic agent is conjugated to an antibody using chemical methods in vitro. Nonlimiting exemplary chemical methods of conjugation are known in the art, and include services, methods and/or reagents commercially available from, e.g., Thermo Scientific Life Science Research Produces (formerly Pierce; Rockford, Ill.), Prozyme (Hayward, Calif.), SACRI Antibody Services (Calgary, Canada), AbD Serotec (Raleigh, N.C.), etc. In some embodiments, when a label and/or cytotoxic agent is a polypeptide, the label and/or cytotoxic agent can be expressed from the same expression vector with at least one antibody chain to produce a polypeptide comprising the label and/or cytotoxic agent fused to an antibody chain. One skilled in the art can select a suitable method for conjugating a label and/or cytotoxic agent to an antibody according to the intended application.

Exemplary Leader Sequences

In order for some secreted proteins to express and secrete in large quantities, a leader sequence from a heterologous protein may be desirable. In some embodiments, a leader sequence is selected from SEQ ID NOs: 3 and 4, which are light chain and heavy chain leader sequences, respectively. In some embodiments, employing heterologous leader sequences may be advantageous in that a resulting mature polypeptide may remain unaltered as the leader sequence is removed in the ER during the secretion process. The addition of a heterologous leader sequence may be required to express and secrete some proteins.

Certain exemplary leader sequence sequences are described, e.g., in the online Leader sequence Database maintained by the Department of Biochemistry, National University of Singapore. See Choo et al., *BMC* Bioinformatics, 6: 249 (2005); and PCT Publication No. WO 2006/081430.

Nucleic Acid Molecules Encoding Anti-CSF1R Antibodies

Nucleic acid molecules comprising polynucleotides that encode one or more chains of anti-CSF1R antibodies are provided. In some embodiments, a nucleic acid molecule comprises a polynucleotide that encodes a heavy chain or a light chain of an anti-CSF1R antibody. In some embodiments, a nucleic acid molecule comprises both a polynucleotide that encodes a heavy chain and a polynucleotide that encodes a light chain, of an anti-CSF1R antibody. In some embodiments, a first nucleic acid molecule comprises a first polynucleotide that encodes a heavy chain and a second nucleic acid molecule comprises a second polynucleotide that encodes a light chain.

In some such embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an anti-CSF1R antibody comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

Nucleic acid molecules may be constructed using recombinant DNA techniques conventional in the art. In some embodiments, a nucleic acid molecule is an expression vector that is suitable for expression in a selected host cell.

Anti-CSF1R Antibody Expression and Production

Vectors

Vectors comprising polynucleotides that encode anti-CSF1R heavy chains and/or anti-CSF1R light chains are provided. Vectors comprising polynucleotides that encode anti-CSF1R heavy chains and/or anti-CSF1R light chains are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NS0 cells. Exemplary such vectors are described, e.g., in Running Deer et al., *Biotechnol. Prog.* 20:880-889 (2004).

In some embodiments, a vector is chosen for in vivo expression of anti-CSF1R heavy chains and/or anti-CSF1R light chains in animals, including humans. In some such embodiments, expression of the polypeptide is under the control of a promoter that functions in a tissue-specific manner. For example, liver-specific promoters are described, e.g., in PCT Publication No. WO 2006/076288.

Host Cells

In various embodiments, anti-CSF1R heavy chains and/or anti-CSF1R light chains may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S and DG44 cells; PER.C6® cells (Crucell); and NS0 cells. In some embodiments, anti-CSF1R heavy chains and/or anti-CSF1R light chains may be expressed in yeast. See, e.g., U.S. Publication No. US 2006/0270045 A1. In some embodiments, a particular eukaryotic host cell is selected based on its ability to make desired post-translational modifications to the anti-CSF1R heavy chains and/or anti-CSF1R light chains. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., *Molecular Cloning, A Laboratory Manual*, $3^{rd}$ ed. Cold Spring Harbor Laboratory Press (2001). Nucleic acids may be transiently or stably transfected in the desired host cells, according to any suitable method.

In some embodiments, one or more polypeptides may be produced in vivo in an animal that has been engineered or transfected with one or more nucleic acid molecules encoding the polypeptides, according to any suitable method.

Purification of Anti-CSF1R Antibodies

Anti-CSF1R antibodies may be purified by any suitable method. Such methods include, but are not limited to, the use of affinity matrices or hydrophobic interaction chromatography. Suitable affinity ligands include the CSF1R ECD and ligands that bind antibody constant regions. For example, a Protein A, Protein G, Protein A/G, or an antibody affinity column may be used to bind the constant region and to purify an anti-CSF1R antibody. Hydrophobic interactive chromatography, for example, a butyl or phenyl column, may also suitable for purifying some polypeptides. Many methods of purifying polypeptides are known in the art.

Cell-Free Production of Anti-CSF1R Antibodies

In some embodiments, an anti-CSF1R antibody is produced in a cell-free system. Nonlimiting exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

Therapeutic Compositions and Methods

Methods of Treating Diseases Using Anti-CSF1R Antibodies

Antibodies of the invention, and compositions comprising antibodies of the invention, are provided for use in methods of treatment for humans or animals. Methods of treating disease comprising administering anti-CSR1R antibodies are also provided. Nonlimiting exemplary diseases that can be treated with anti-CSF1R antibodies include, but are not limited to, RA, MS, cancer, metastasis-induced osteolytic bone loss, osteolytic disorders, and hypercalcemia-induced bone loss.

In some embodiments, methods of treating inflammatory conditions comprising administering an anti-CSF1R antibody are provided. In some embodiments, an inflammatory condition is selected from psoriasis, SLE (lupus), COPD, atopic dermatitis, and atherosclerosis, macrophage activation syndrome, and histiocytosis X.

In some embodiments, methods of treating an inflammatory condition comprising administering an anti-CSF1R antibody are provided, wherein the inflammatory condition is selected from: proliferative vascular disease, acute respiratory distress syndrome, cytokine-mediated toxicity, interleukin-2 toxicity, appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, inflammatory bowel disease, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, celiac disease, congestive heart failure, meningitis, encephalitis, cerebral infarction, cerebral embolism, Guillain-Barre syndrome, neuritis, neuralgia, spinal cord injury, paralysis, uveitis, arthritides, arthralgias, osteomyelitis, fasciitis, Paget's disease, gout, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, type I diabetes, type 2 diabetes, Berger's disease, Retier's syndrome, and Hodgkins disease, or in treating inflammation associated with these conditions.

In some embodiments, methods of treating cancer comprising administering an anti-CSF1R antibody are provided. In some embodiments, the cancer is a CSF1-secreting cancer. In some embodiments, the cancer is one or more cancers selected from breast cancer, prostate cancer, endometrial cancer, bladder cancer, kidney cancer, esophageal cancer, squamous cell carcinoma, uveal melanoma, follicular lymphoma, renal cell carcinoma, cervical cancer, and ovarian cancer. In some embodiments, an anti-CSF1R antibody is useful for treating one or more cancers selected from lung cancer, colorectal cancer, brain cancer, pancreatic cancer, head and neck cancer, liver cancer, leukemia, lymphoma, Hodgkin's disease, multiple myeloma, melanoma, astrocytoma, stomach cancer, and pulmonary adenocarcinoma.

Routes of Administration and Carriers

In various embodiments, anti-CSF1R antibodies may be administered in vivo by various routes, including, but not limited to, oral, intra-arterial, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. A nucleic acid molecule encoding an anti-CSF1R antibody may be coated onto gold microparticles and delivered intradermally by a particle bombardment device, or "gene gun," as described in the literature (see, e.g., Tang et al., *Nature* 356:152-154 (1992)). The appropriate formulation and route of administration may be selected according to the intended application.

In various embodiments, compositions comprising anti-CSF1R antibodies are provided in formulations with a wide variety of pharmaceutically acceptable carriers (see, e.g., Gennaro, *Remington: The Science and Practice of Pharmacy with Facts and Comparisons: Drugfacts Plus,* 20th ed. (2003); Ansel et al., *Pharmaceutical Dosage Forms and Drug Delivery Systems,* 7$^{th}$ ed., Lippencott Williams and Wilkins (2004); Kibbe et al., *Handbook of Pharmaceutical Excipients,* 3$^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In various embodiments, compositions comprising anti-CSF1R antibodies may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical packs and kits comprising one or more containers, each containing one or more doses of an anti-CSF1R antibody are also provided. In some embodiments, a unit dosage is provided wherein the unit dosage contains a predetermined amount of a composition comprising an anti-CSF1R antibody, with or without one or more additional agents. In some embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in some embodiments, the composition may be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition of the invention comprises heparin and/or a proteoglycan.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In general, anti-CSF1R antibodies may be administered in an amount in the range of about 10 µg/kg body weight to about 100 mg/kg body weight per dose. In some embodiments, anti-CSF1R antibodies may be administered in an amount in the range of about 50 µg/kg body weight to about 5 mg/kg body weight per dose. In some embodiments, anti-CSF1R antibodies may be administered in an amount in the range of about 100 µg/kg body weight to about 10 mg/kg body weight per dose. In some embodiments, anti-CSF1R antibodies may be administered in an amount in the range of about 100 µg/kg body weight to about 20 mg/kg body weight per dose. In some embodiments, anti-CSF1R antibodies may be administered in an amount in the range of about 0.5 mg/kg body weight to about 20 mg/kg body weight per dose.

The anti-CSF1R antibody compositions may be administered as needed to subjects. Determination of the frequency of administration may be made by persons skilled in the art, such as an attending physician based on considerations of the condition being treated, age of the subject being treated, severity of the condition being treated, general state of health of the subject being treated and the like. In some embodiments, an effective dose of an anti-CSF1R antibody is administered to a subject one or more times. In various embodiments, an effective dose of an anti-CSF1R antibody is administered to the subject once a month, more than once a month, such as, for example, every two months or every three months. In other embodiments, an effective dose of an anti-CSF1R antibody is administered less than once a month, such as, for example, every two weeks or every week. An effective dose of an anti-CSF1R antibody is administered to the subject at least once. In some embodiments, the effective dose of an anti-CSF1R antibody may be administered multiple times, including for periods of at least a month, at least six months, or at least a year.

Combination Therapy

Anti-CSF1R antibodies may be administered alone or with other modes of treatment. They may be provided before, substantially contemporaneous with, or after other modes of treatment, for example, surgery, chemotherapy, radiation therapy, or the administration of a biologic, such as another therapeutic antibody. For treatment of rheumatoid arthritis, anti-CSF1R antibodies may be administered with other therapeutic agents, for example, methotrexate, anti-TNF agents such as Remicade, Humira, Simponi, and Enbrel; glucocorticoids such as prednisone; Leflunomide; Azothioprine; JAK inhibitors such as CP 590690; SYK inhibitors such as R788; anti-IL-6 antibodies; anti-IL-6R antibodies; anti-CD-20 antibodies; anti-CD19 antibodies; anti-GM-CSF antibodies; and anti-GM-CSF-R antibodies. For treatment of multiple sclerosis, anti-CSF1R antibodies may be administered with other therapeutic agents, for example, interferon alpha; interferon beta; prednisone; anti-alpha4 integrin antibodies such as Tysabri; anti-CD20 antibodies such as Rituxan; FTY720 (Fingolimod); and Cladribine (Leustatin).

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Selection of Fabs that Bind CSF1R Extracellular Domain (ECD)

Mice were immunized with a human CSF1R extracellular domain Fc fusion, hCSF1R ECD.506-Fc (SEQ ID NO: 6). Spleens from immunized mice were isolated, and a Fab phage display library was created from the spenocytes. Fab-expressing phage were selected for binding to human CSF1R ECD. Fabs from positive-binding phage were expressed and purified from bacteria. A total of 1056 Fab clones were selected for further analysis.

Fabs were screened for the ability to bind human CSF1R ECD, block binding of human CSF1 to human CSF1R ECD, and block binding of human IL34 to human CSF1R ECD. Sequence analysis and clusertering of the Fabs that were selected from that screen was then performed and certain unique Fabs were selected.

The unique Fabs were further analyzed for the ability to bind human CSF1R ECD, the ability to bind cynomolgus CSF1R ECD, and the ability to bind mouse CSF1R ECD. The Fabs were also analyzed for the ability to block human CSF1 binding to human CSF1R ECD and the ability to block human IL34 binding to human CSF1R ECD, and the ability to inhibit ligand-induced CSF1R phosphorylation in the presence of CSF1 or IL34. (Data not shown.)

Example 2

Reformatting of Anti-CSF1R Fabs to Make Chimeric Antibodies

Following the Fab characterization, eleven of the Fabs were selected for reformatting to chimeric antibodies. Each Fab was reformatted to a chimeric antibody comprising a human IgG4 heavy chain constant region with the S241P mutation, and a human κ light chain constant region. Briefly, Fab VH regions cloned into and expressed from vector pTT5 (Biotechnology Research Institute, Montreal, Canada; and National Research Research Council of Canada, Ottawa, Canada) modified to contain a mouse IgH leader sequence (SEQ ID NO: 4) and a human IgG4 heavy chain constant region with the S241P mutation (SEQ ID NO: 94). Fab VL regions were cloned into and expressed from vector pTT5 modified to contain a mouse Igκ leader sequence (SEQ ID NO: 3) and a human Igκ light chain constant region (SEQ ID NO: 95). Fab V regions were inserted in such a way as not to introduce non-antibody derived amino acid sequences into the final proteins.

Example 3

Expression and Characterization of Chimeric Antibodies

The chimeric antibodies were transiently expressed and purified substantially as described below in Example 5.

The 11 chimeric antibodies were assayed for binding to human, cynomolgus, and mouse CSF1R ECD. The chimeric antibodies were also assayed for the ability to block binding of human CSF1 to human CSF1R ECD, the ability to block binding of human IL34 to human CSF1R ECD, the ability to block binding of human CSF1 to cynomolgus CSF1R ECD, and the ability to inhibit ligand-induced CSF1R phosphorylation in the presence of CSF1 or IL34. The chimeric antibodies were further assayed for binding to CSF1R on the surface of cells. Finally, the chimeric antibodies were assayed to confirm that they do not induce CSF1R phosphorylation in the absence of ligand. (Data not shown.)

Example 4

Humanization of Anti-CSF1R Antibodies

From the analyses described above, chimeric anti-CSF1R antibodies 0301, 0302, and 0311 were selected for humanization. The antibodies were humanized by changing certain amino acid residues in the framework regions of the heavy and light chain variable regions. The criteria used for humanization were as described previously, e.g., in U.S. Publication No. US 2009/0136500.

For cAb 0301, three humanized heavy chain variable regions and two humanized light chain variable regions were designed, for a total of six humanized antibodies, Ab1 to Ab6. For cAb 0302, two humanized heavy chain variable regions and three humanized light chain variable regions were designed, for a total of six humanized antibodies, Ab7 to Ab12. For cAb 0311, two humanized heavy chain variable regions and two humanized light chain variable regions were designed, for a total of four humanized antibodies, Ab13 to Ab16.

Figure 1B:
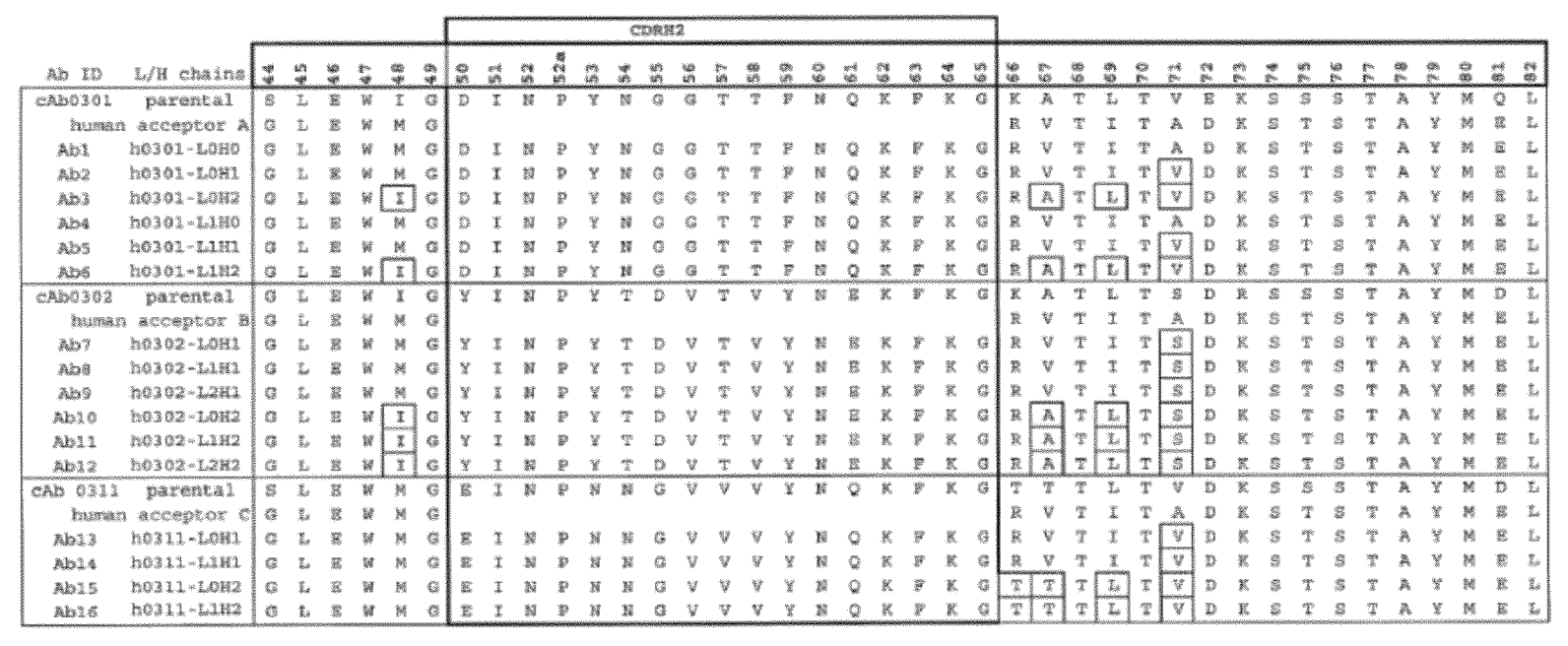
Figure 1C:
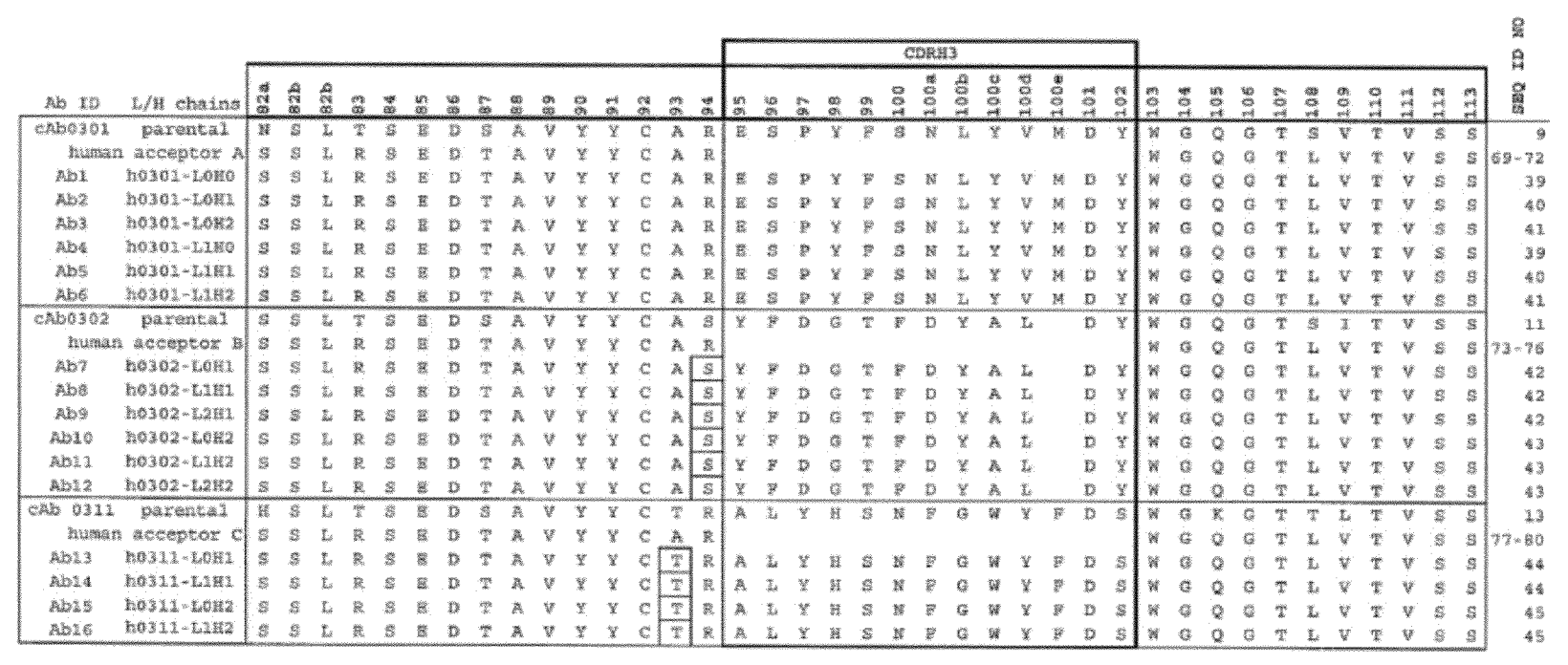

The sequences for each of the humanized heavy chain variable regions and humanized light chain variable regions, aligned with the sequences of the parental chimeric antibody variable regions and the sequences of the human acceptor variable framework regions are shown in FIG. 1 (heavy chains) and 2 (light chains). The changes in humanized variable region sequences relative to the human acceptor variable framework region sequences are boxed. Each of the CDRs for each of the variable regions is shown in a boxed region, and labeled as "CDR" above the boxed sequences.

Table 8, below, shows the full sequences for the humanized heavy chains and humanized light chains of antibodies Ab1 to Ab16. The name and SEQ ID NOs of the humanized heavy chain and humanized light chain of each of those antibodies is shown in Table 2.

TABLE 2

Humanized heavy chains and light chains of Ab1 to Ab16

| Humanized antibody | Humanized HC | SEQ ID NO | Humanized LC | SEQ ID NO |
| --- | --- | --- | --- | --- |
| Ab1 | h0301-H0 | 53 | h0301-L0 | 60 |
| Ab2 | h0301-H1 | 54 | h0301-L0 | 60 |
| Ab3 | h0301-H2 | 55 | h0301-L0 | 60 |
| Ab4 | h0301-H0 | 53 | h0301-L1 | 61 |
| Ab5 | h0301-H1 | 54 | h0301-L1 | 61 |
| Ab6 | h0301-H2 | 55 | h0301-L1 | 61 |
| Ab7 | h0302-H1 | 56 | h0302-L0 | 62 |
| Ab8 | h0302-H1 | 56 | h0302-L1 | 63 |
| Ab9 | h0302-H1 | 56 | h0302-L2 | 64 |
| Ab10 | h0302-H2 | 57 | h0302-L0 | 62 |
| Ab11 | h0302-H2 | 57 | h0302-L1 | 63 |
| Ab12 | h0302-H2 | 57 | h0302-L2 | 64 |
| Ab13 | h0311-H1 | 58 | h0311-L0 | 65 |
| Ab14 | h0311-H1 | 58 | h0311-L1 | 66 |
| Ab15 | h0311-H2 | 59 | h0311-L0 | 65 |
| Ab16 | h0311-H2 | 59 | h0311-L1 | 66 |

Example 5

Humanized Anti-CSF1R Antibodies Bind to Human and Cynomolgus CSF1R ECD, but not to Mouse CSF1R ECD The 16 humanized antibodies were transiently expressed in CHO cells, as follows. CHO-3E7 cells were co-transfected with individual heavy and light chain expression plasmids at a mass ratio of 1 heavy chain plasmid to 2 light chain plasmids using polyethyleneinimine (PEI) at a DNA:PEI ratio of 1:5. Total DNA used per transfection was 1.5 µg/ml of cells.

Humanized antibodies were purified from transfected cell supernatants using HiTrap Protein A HP columns (GE Healthcare) followed by further purification using Phenyl HP columns (GE Healthcare). Antibody containing supernatants were loaded onto HiTrap Protein A HP columns pre-equilibrated with PBS/0.5M NaCl. Antibody loaded columns were washed with 10 column volumes PBS/0.5M NaCl, and eluted with a mixed linear-step gradient of 0.1 M Glycine, pH 2.7/ 0.5 M NaCl directly into 100 ul of 1M Tris buffer, pH 8.0. Antibody containing eluates were dialyzed against PBS, after which 2.4 M $(NH_4)_2SO_4$ (Sigma) was added to achieve a conductivity equal to that of 10 mM Potassium Phosphate pH7.0/1.2 M $(NH_4)_2SO_4$. Antibodies were then loaded on 1 ml Phenyl HP columns (GE Healthcare) pre-equilibrated with 10 mM Potassium Phosphate pH7.0/1.2 M $(NH_4)_2SO_4$. Antibody loaded columns were washed with 15 column volumes 10 mM Potassium Phosphate pH7.0/1.2 M $(NH_4)_2SO_4$, and eluted with a 20 column volume gradient of 10 mM Potassium Phosphate, pH 7.0. Antibody containing fractions were pooled and dialyzed against PBS.

The humanized antibodies, along with their parental chimeric antibodies (cAbs), were assayed for binding to human, cynomolgus, and mouse CSF1R ECD, as follows.

Human CSF1R Binding Activity

Ninety-six well clear-bottom ELISA plates were coated overnight with 1 µg/ml recombinant hCSF1R ECD.506-Fc (SEQ ID NO: 6; FivePrime Therapeutics) or Human M-CSF R Fc Chimera (R&D Systems) in PBS. The next morning, wells were washed four times with 0.05% Tween20 in PBS (PBST) and blocked with Blocker-Blotto (Pierce). Fifty µl of 0.5× serial dilutions of the humanized antibody or parental chimeric antibody, beginning with 2000 ng/ml, diluted 1:1 in Blocker-Blotto were added to the CSF1R-coated wells. After incubation at room temperature (RT) for 90 min, wells were washed four times with PBST, and a 1:5000 dilution of a peroxidase-conjugated Goat anti-Human kappa Light chain antibody (Sigma) in Blocker-Blotto was added to each well. After incubation at RT for 60 min, wells were washed four times with PBST, and 50 µl o-phenylenediamine dihydrochloride peroxidase substrate (Sigma) was added to each well. After incubation at RT for 30 min, A450 values of each well were read directly on a SpectraMaxPlus spectrophotometer with SoftMaxPro software (Molecular Devices).

The results of that experiment is shown in FIG. 3. All of the humanized antibodies bound to human CSF1R ECD within the range of concentrations tested.

Cynomolgus CSF1R Binding Curve

The binding curve for each humanized antibody binding to cynomolgus CSF1R ECD was determined as described above for human CSF1R, except the wells of the clear-bottom ELISA plates were coated overnight with 2 µg/ml recombinant cynoCSF1R ECD-Fc (FivePrime Therapeutics, SEQ ID NO: 8, but without the 19 amino acid leader sequence).

Figure 4:
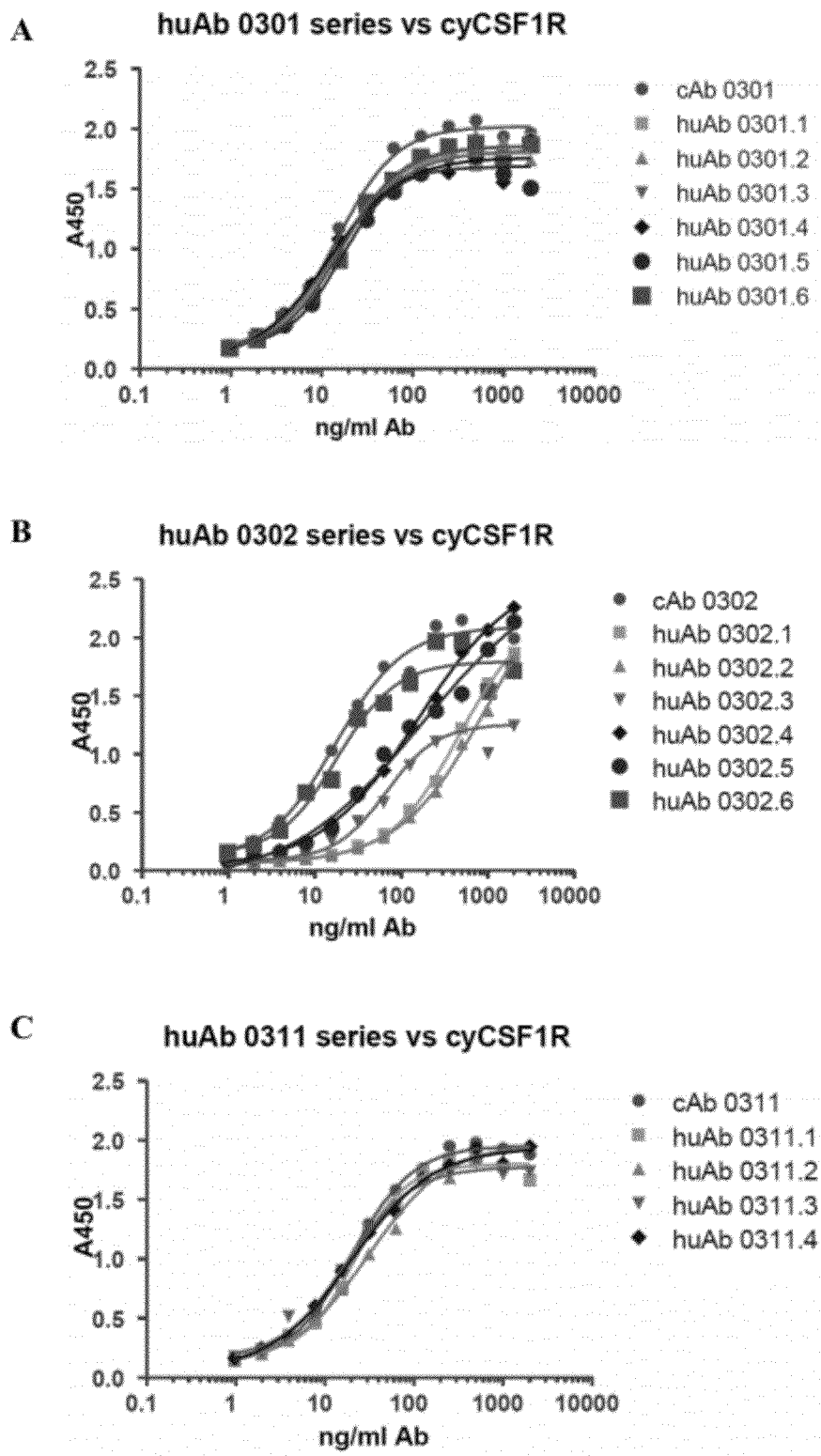
FIGS. 4A-C show binding curves for certain humanized antibodies binding to cynomolgus CSF1R ECD, as described in Example 5.

The results of that experiment are shown in FIG. 4. All of the humanized antibodies bound to cynomolgus CSF1R ECD within the range of concentrations tested.

Mouse CSF1R Binding Curve

The binding curve for each humanized antibody binding to mouse CSF1R ECD was determined as described above for human CSF1R, except the wells of the clear-bottom ELISA plates were coated overnight with 2 µg/ml recombinant mCSF1R ECD-Fc (FivePrime Therapeutics, SEQ ID NO: 93).

Figure 5:
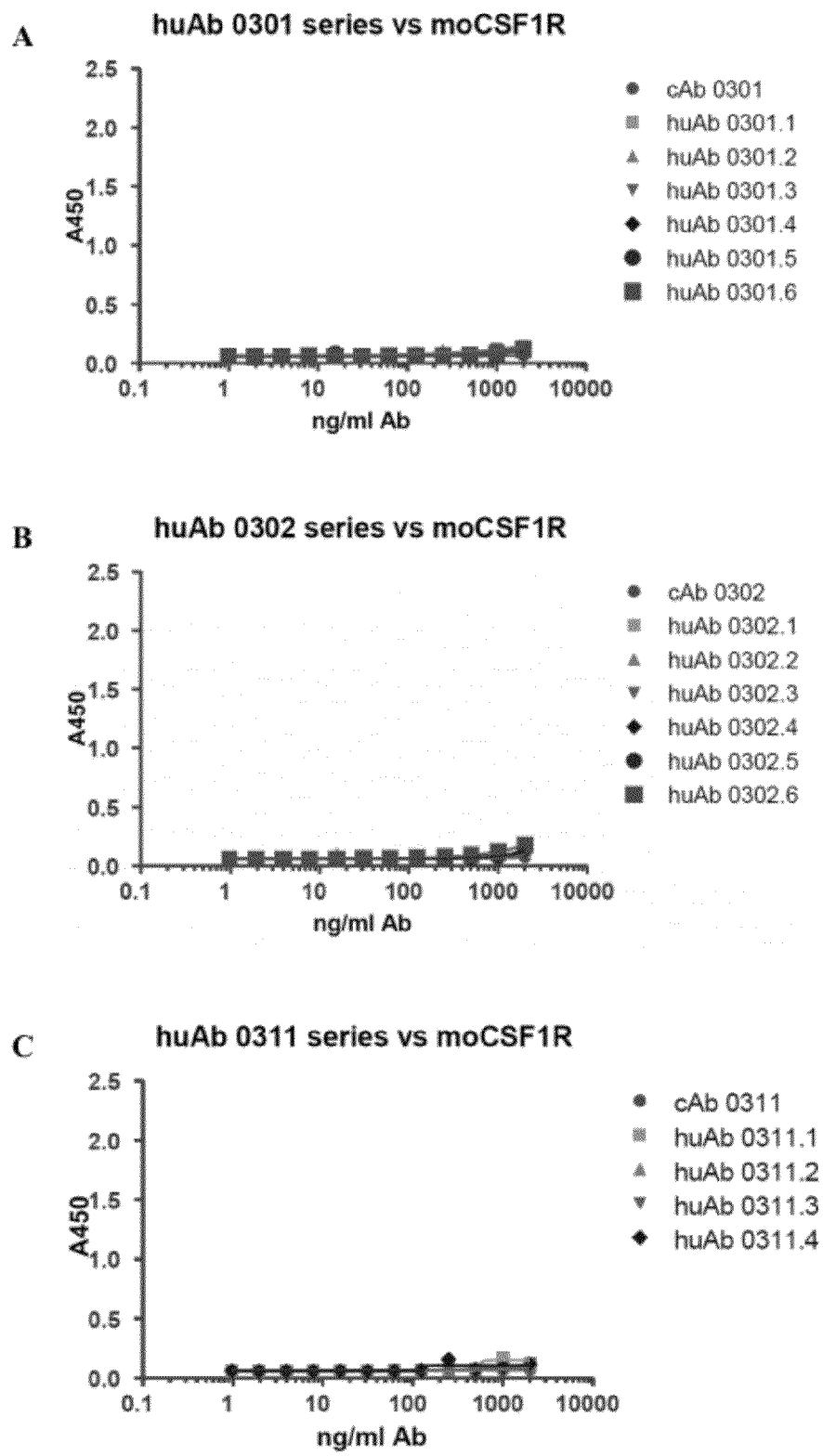
FIGS. 5A-C show binding curves for certain humanized antibodies binding to mouse CSF 1R ECD, as described in Example 5.

The results of that experiment are shown in FIG. 5. None of the humanized antibodies, or the parental chimeric antibodies, detectably bound to mouse CSF1R ECD over the range of concentrations tested.

Calculation of EC50s

Table 3 shows the EC50, calculated using the non-linear regression (curve-fit) analysis algorithm of the GraphPad Prism software (GraphPad Software) for each humanized antibody binding to human CSF1R ECD and cynomolgus CSF1R ECD. Because none of the chimeric antibodies detectably bound to mouse CSF1R ECD, an EC50 could not be calculated from that data. Table 3 also includes the calculated EC50s for the parental chimeric antibodies.

TABLE 3

Binding activity of humanized anti-CSF1R antibodies

| Humanized antibody | Human CSF1R ECD EC50 (ng/ml) | Cynomolgus CSF1R ECD EC50 (ng/ml) |
|---|---|---|
| cAb 0301 | 11.4 | 15.18 |
| h0301-L0H0 | 13.4 | 15.11 |
| h0301-L0H1 | 14.23 | 14.39 |
| h0301-L0H2 | 14.77 | 13.79 |
| h0301-L1H0 | 13.35 | 11.93 |
| h0301-L1H1 | 16.47 | 16.66 |
| h0301-L1H2 | 16.23 | 16.59 |
| cAb 0302 | 15.94 | 17.34 |
| h0302-L0H1 | 14.64 | 466.5 |
| h0302-L1H1 | 21.43 | 1058 |
| h0302-L2H1 | 7.741 | 66.04 |
| h0302-L0H2 | 17.85 | 154.9 |
| h0302-L1H2 | 22.1 | 172.5 |
| h0302-L2H2 | 10.15 | 17.96 |
| cAb 0311 | 17.65 | 20.06 |
| h0311-L0H1 | 13.12 | 21.65 |
| h0311-L1H1 | 14.32 | 30.88 |
| h0311-L0H2 | 11.54 | 17.47 |
| h0311-L1H2 | 13.26 | 20.27 |

Example 6

Humanized Anti-CSF1R Antibodies Inhibit Ligand-Induced CSF1R Phosphorylation

CSF1R is phosphorylated in the presence of ligands CSF1 or IL34. The humanized antibodies, along with their parental chimeric antibodies (cAbs), were tested for their ability to inhibit CSF1R phosphorylation induced by either ligand, as follows.

Inhibition of CSF1-Induced Phosphorylation

CSF1R (SEQ ID NO: 2)-transfected CHO cells were incubated with serial dilutions of each humanized antibody or a parental chimeric antibody, beginning at 8 µg/ml, for 60 min on ice, after which 3.3 nM of human CSF1 (M-CSF, R&D Systems) was added to the cells. (For the 0301 series of humanized antibodies, serial dilutions beginning at 2 µg/ml of humanized antibody and parental chimeric antibody was used.) The cells were incubated for 3 minutes at 37° C., and then lysed by addition of 1/10× volume of 10× cell lysis buffer (Cell Signaling Technology). The amount of phosphorylated CSF1R in the cell lysates was quantified using a human phospho-M-CSF R ELISA kit (R&D Systems) according to the manufacturer's instructions.

Figure 6:
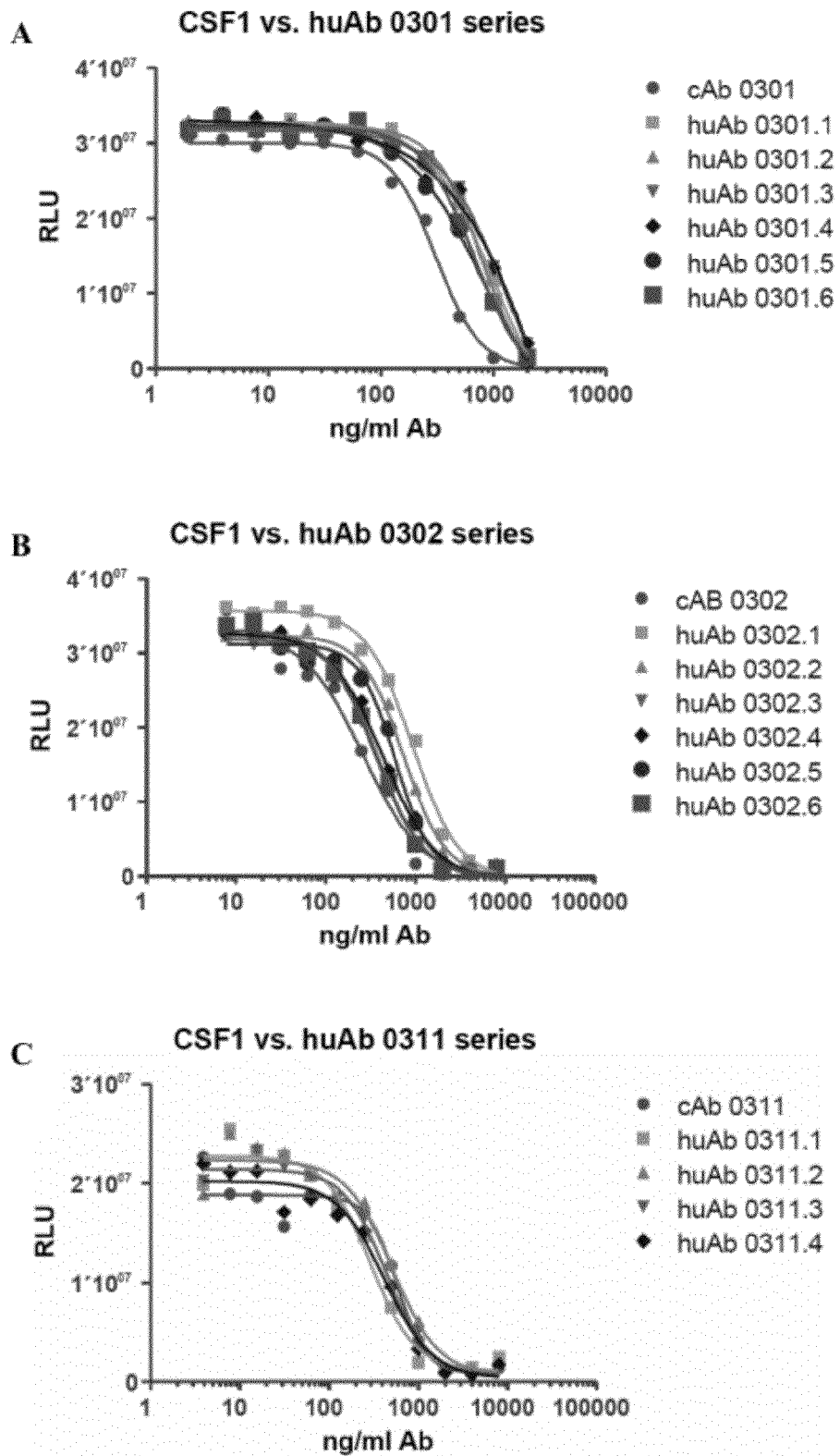
FIGS. 6A-C show inhibition of CSF1 induced CSF1R phosphorylation by certain humanized antibodies, as described in Example 6.

The results of that experiment are shown in FIGS. 6A to 6C. All of the humanized antibodies were able to inhibit human CSF1-induced phosphorylation of human CSF1R ECD within the range of concentrations tested.

Inhibition of IL34-Induced Phosphorylation

CSF1R (SEQ ID NO: 2)-transfected CHO cells were incubated with 0.002 to 8 µg/ml of each humanized antibody or a parental chimeric antibody for 60 min on ice, after which 3.3 nM of human IL34 (FivePrime Therapeutics; SEQ ID NO: 68) was added to the cells. The cells were incubated for 3 minutes at 37° C., and then lysed by addition of 1/10× volume of 10× cell lysis buffer (Cell Signaling Technology). The amount of phosphorylated CSF1R in the cell lysates was quantified using a human phospho-M-CSF R ELISA kit (R&D Systems) according to the manufacturer's instructions.

Figure 7:
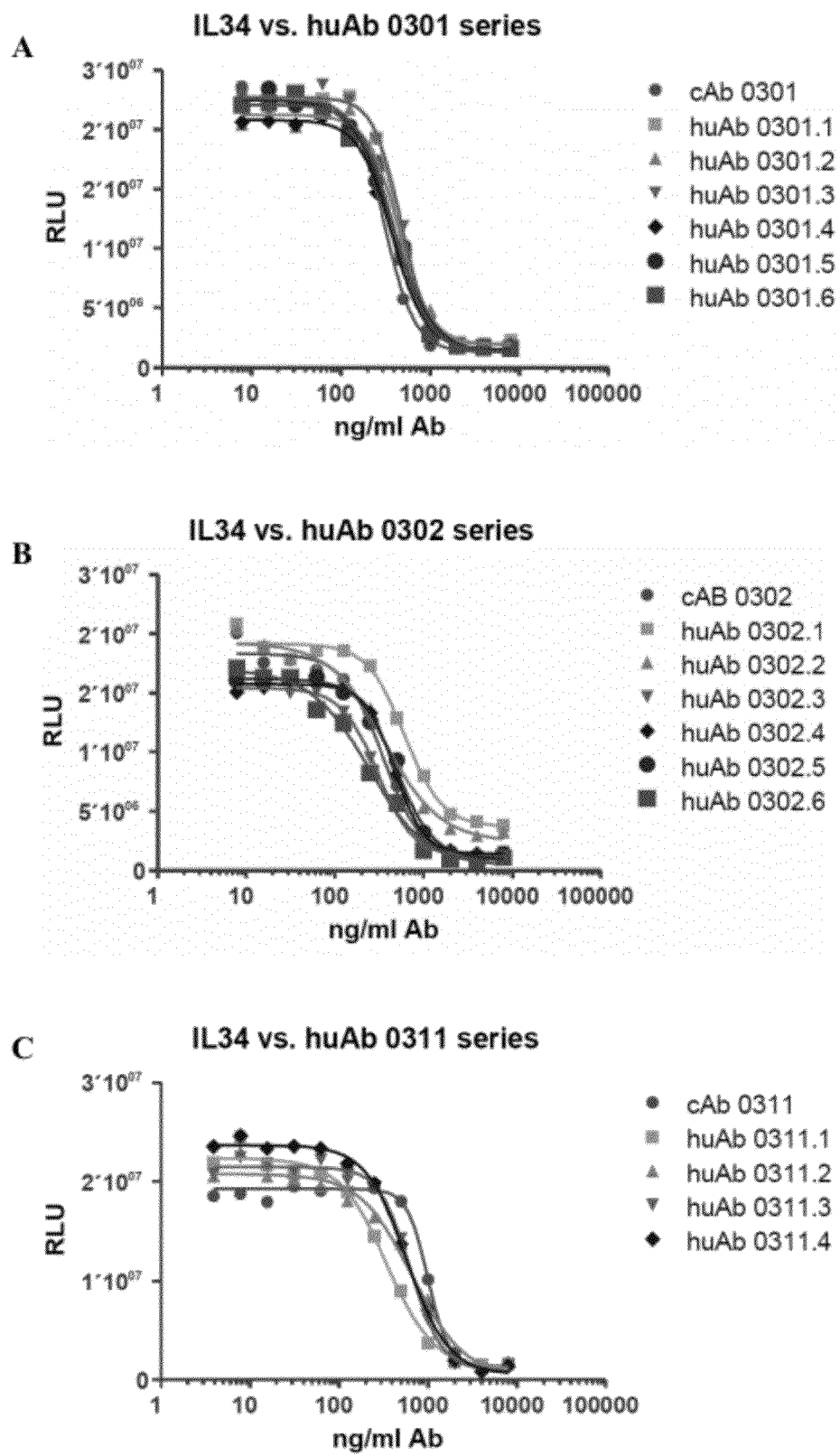
FIGS. 7A-C show inhibition of IL34 induced CSF1R phosphorylation by certain humanized antibodies, as described in Example 6.

The results of that experiment are shown in FIGS. 7A to 7C. All of the humanized antibodies were able to inhibit human IL34-induced phosphorylation of human CSF1R within the range of concentrations tested.

Example 7

Humanized Anti-CSF1R Antibodies Block Human CSF1 and Human IL34 Binding to Human and Cynomolgous CSF1R Human CSF1/CSF1R Blocking Activity The humanized antibodies, along with the parental chimeric antibodies (cAbs), were tested for their ability to block human CSF1 binding to human and cynomolgus CSF1R ECD, as follows.

Recombinant Human CSF1 (M-CSF; R&D Systems) was biotinylated using an NH2-Biotin Labeling Kit (Dojindo Molecular Technologies). One hundred µl of 1 µg/ml biotinylated CSF1 in PBST/0.1% BSA was added to the wells of Reacti-Bind Streptavidin coated plates (Pierce) pre-blocked with SuperBlock blocking buffer (Pierce) according to the manufacturer's instructions. Fifty µl of 0.5× serial dilutions of the humanized antibody or parental chimeric antibody, beginning with 2000 ng/ml, was incubated with 50 ng/ml hCSF1R ECD.506-Fc (SEQ ID NO: 6; FivePrime Therapeutics) or 50 ng/ml cynoCSF1R ECD-Fc (FivePrime Therapeutics, SEQ ID NO: 8, but without the 19 amino acid leader sequence) in 100 µl PBST/0.1% BSA for 90 min at RT, after which the admix was transferred to one or more wells of a ligand-coated plate. After 90 min at RT, wells were washed with PBST, and a 1:5000 dilution of an Fc-fragment-specific peroxidase-conjugated goat anti-human IgG (Jackson Immuno Research) in PBST/0.1% BSA was added to each well. After incubation at RT for 60 min, wells were washed with PBST/0.1% BSA, and o-phenylenediamine dihydrochloride peroxidase substrate (Sigma) was added to each well. After incubation at RT for 30 min, A450 values of each well were read directly on a SpectraMaxPlus spectrophotometer with SoftMaxPro software (Molecular Devices).

Figure 8:
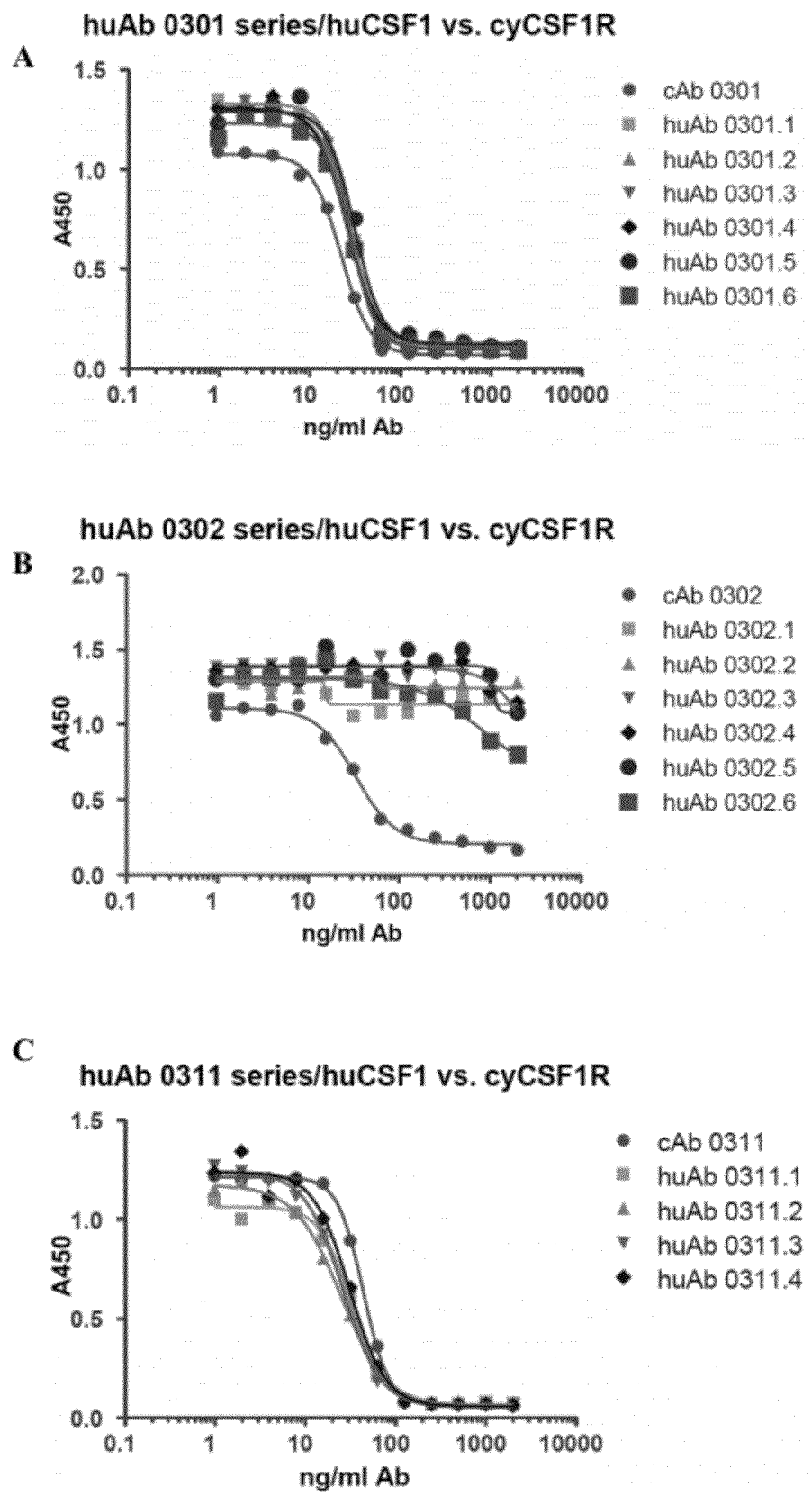
FIGS. 8A-C show blocking of human CSF1 binding to cynomolgus CSF1R ECD by certain humanized antibodies, as described in Example 7.

The results of that experiment for cynomolgus CSF1R are shown in FIGS. 8A to 8C. All of the humanized antibodies based on Fabs 0301 and 0311 were able to block human CSF1 binding to cynomolgus CSF1R ECD within the range of concentrations tested. None of the humanized antibodies based on Fab 0302 showed similar blocking activity in that experiment compared to the blocking activity of cAb 0302.

Human IL34/CSF1R Blocking Activity

The humanized antibodies were tested for their ability to block human IL34 binding to human CSF1R ECD. The blocking activity of each humanized antibody was determined as described above for blocking of CSF1, except recombinant human IL34 (FivePrime Therapeutics; SEQ ID NO: 68) was biotinylated using an NH2-Biotin Labeling Kit (Dojindo Molecular Technologies), and then 100 µl of 1 µg/ml biotinylated recombinant IL34 in PBST/0.1% BSA was added to the wells of Reacti-Bind Streptavidin coated plates (Pierce) pre-blocked with SuperBlock blocking buffer (Pierce) according to the manufacturer's instructions.

Figure 9:
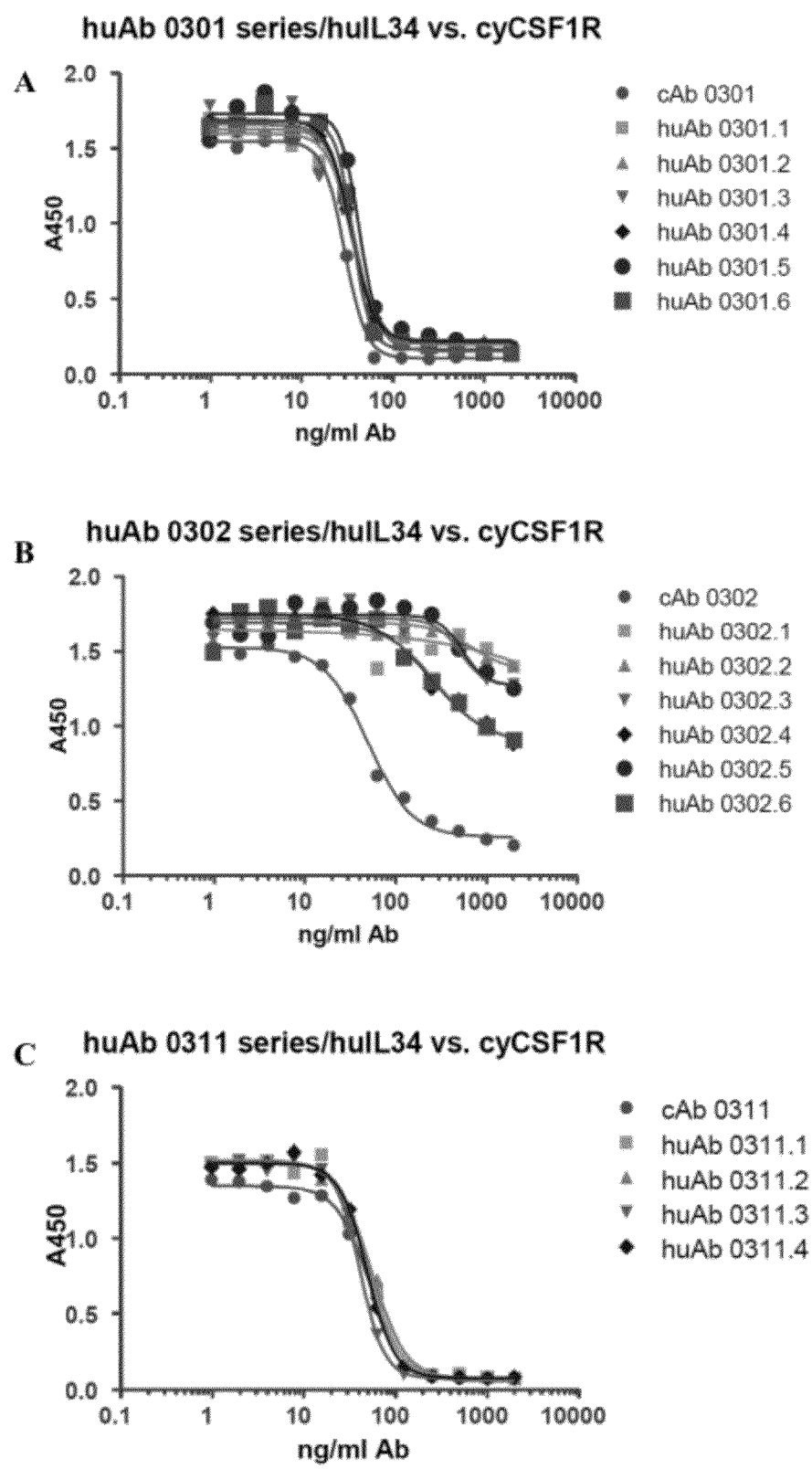
FIGS. 9A-C show blocking of human IL34 binding to cynomolgus CSF1R ECD by certain humanized antibodies, as described in Example 7.

The results of that experiment for cynomolgus CSF1R are shown in FIGS. 9A to 9C. All of the humanized antibodies based on Fabs 0301 and 0311 were able to block human IL34 binding to cynomolgus CSF1R ECD within the range of concentrations tested. None of the humanized antibodies based on Fab 0302 showed similar blocking activity in that experiment compared to the blocking activity of cAb 0302.

Calculation of IC50s

Table 4 shows the IC50, calculated using the non-linear regression (curve-fit) analysis algorithm of the GraphPad Prism software (GraphPad Software), for inhibition of ligand-induced CSF1R phosphorylation by each humanized antibody. Table 4 also shows the IC50, calculated using the non-linear regression (curve-fit) analysis algorithm of the GraphPad Prism software (GraphPad Software), for blocking of ligand binding to CSF1R ECD by each humanized antibody. Finally, Table 4 shows the number of amino acids in the framework regions of the light and heavy chain of each humanized antibody that were back-mutated to the corresponding mouse amino acid residue. For example, humanized antibody h0301L1H1 has one amino acid in a light chain framework region that was back-mutated to the mouse amino acid, and one amino acid in the heavy chain framework regions that was back-mutated to the mouse amino acid.

Figure 2A:
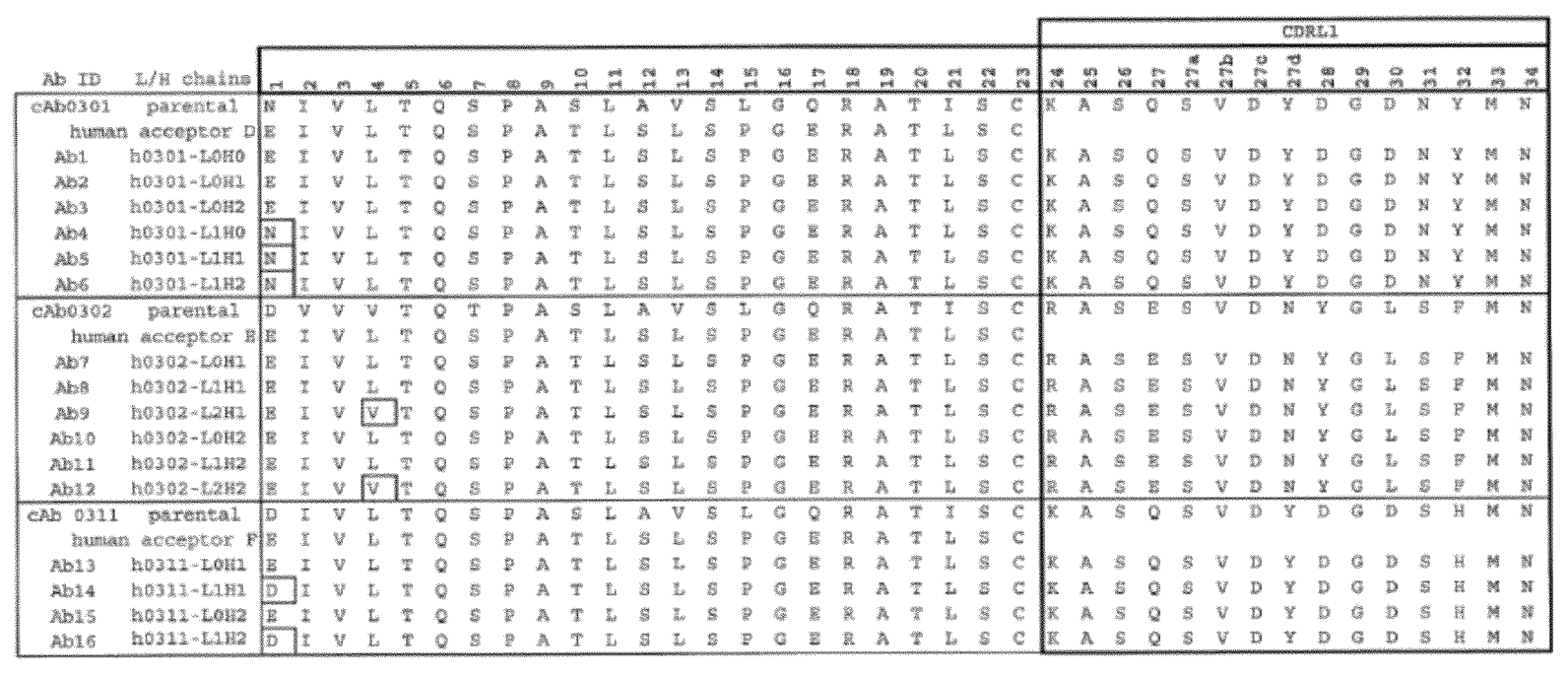

Referring to FIGS. 1 and 2, the back-mutated amino acid in the light chain framework is at position 1 in framework 1, and the back-mutated amino acid in the heavy chain is at position 71 in framework 3 according to Kabat numbering (see FIG. 1B).

TABLE 4

Blocking activity of humanized anti-CSF1R antibodies

| Humanized Antibody | Human CSF1/ Human CSF1R ECD IC50 (ng/ml) | Human IL34/ Human CSF1R ECD IC50 (ng/ml) | Human CSF1/ CynoCSF1R ECD IC50 (ng/ml) | Human IL34/ CynoCSF1R ECD IC50 (ng/ml) | Back-mutated mouse residues in FRs (L + H) |
|---|---|---|---|---|---|
| cAb0301 | 307.2 | 312.2 | 22.01 | 29.53 | |
| h0301-L0H0 | 1031 | 433 | 27.64 | 35.92 | 0 + 0 |
| h0301-L0H1 | 778.1 | 452.6 | 27.45 | 36.43 | 0 + 1 |
| h0301-L0H2 | 1317 | 480.9 | 28.05 | 37.37 | 0 + 4 |
| h0301-L1H0 | 6150 | 378 | 25.53 | 34.84 | 1 + 0 |
| h0301-L1H1 | 814.2 | 384.4 | 31.07 | 42.41 | 1 + 1 |
| h0301-L1H2 | 682.1 | 397.1 | 27.77 | 36.53 | 1 + 4 |
| cAb0302 | 263.5 | 350.8 | 33.09 | 49.38 | |
| h0302-L0H1 | 927.7 | 615 | 15.55 | 2.00E+12 | 0 + 2 |
| h0302-L1H1 | 742 | 363.7 | 60.49 | 676.4 | 1 + 2 |
| h0302-L2H1 | 384 | 303.1 | 89827 | 509.1 | 3 + 2 |
| h0302-L0H2 | 438.2 | 474.2 | none | 248.1 | 0 + 5 |
| h0302-L1H2 | 597.8 | 495.3 | 1085 | 541.3 | 1 + 5 |
| h0302-L2H2 | 354.4 | 240.1 | 837.6 | 278.7 | 3 + 5 |
| cAb 0311 | 577 | 994.2 | 43.47 | 52.1 | |
| h0311-L0H1 | 291.3 | 343.2 | 32.47 | 50.4 | 0 + 2 |
| h0311-L1H1 | 507.5 | 667.4 | 24.68 | 53.69 | 2 + 2 |
| h0311-L0H2 | 435.5 | 633.3 | 25.96 | 40.79 | 0 + 5 |
| h0311-L1H2 | 419 | 578.2 | 30.76 | 48.56 | 2 + 5 |

Example 8

Humanized Anti-CSF1R Antibody Binding Constants

The $k_a$, $k_d$, and $K_D$ for binding to human CSF1R ECD was determined for each of the humanized antibodies as follows.

Binding kinetics of anti-CSF1R humanized antibodies to CSF1R ECD was determined using Biacore T100 Surface Plasmon Resononance (SPR) (GE Healthcare Life Sciences, Piscataway, N.Y.). Each of the humanized anti-CSF1R antibodies was captured on a CM5 sensor chip immobilized with anti-Human IgG antibody using the Human antibody capture kit (GE Healthcare Life Sciences, Piscataway, N.Y.) at 150 RU so that the Rmax value for hCSF1R ECD.506 (SEQ ID NO: 5) binding was 100 RU. Rmax values of less than 150 RU are recommended for accurately determining kinetic values. 10 mM Hepes buffered saline, pH 7.4, with 0.05% Tween20 (HPS-P; GE Healthcare Life Sciences, Piscataway, N.Y.) was used as the running and dilution buffer. hCSF1R ECD.506 was injected at six concentrations (90 nM, 30 nM, 10 nM, 3.33 nM, 1.11 nM, and 0 nM) for 2 minutes and dissociation was observed for 5 minutes to determine humanized antibody/hCSF1R ECD binding kinetic parameters. The association constant, dissociation constant, affinity, and binding capacity of each of the Fabs for human CSF1R ECD was calculated using the Biacore T100 Evaluation software package using the 1:1 binding model.

The results of the kinetic determinations are shown in Table 5.

TABLE 5

Humanised antibody binding affinity for human CSF1R

| huAbAb | $k_a$ (M$^{-1}$s$^{-1}$) | $K_d$ (s$^{-1}$) | $K_D$ (nM) |
|---|---|---|---|
| huAb 0301-L0H0 | 3.22 × 10$^6$ | 1.11 × 10$^{-03}$ | 0.35 |
| huAb 0301-L0H1 | 3.56 × 10$^6$ | 1.22 × 10$^{-03}$ | 0.34 |
| huAb 0301-L0H2 | 2.32 × 10$^6$ | 6.60 × 10$^{-04}$ | 0.28 |
| huAb 0301-L1H0 | 3.29 × 10$^6$ | 1.15 × 10$^{-03}$ | 0.35 |
| huAb 0301-L1H1 | 2.87 × 10$^6$ | 9.21 × 10$^{-04}$ | 0.32 |
| huAb 0301-L1H2 | 2.95 × 10$^6$ | 7.42 × 10$^{-04}$ | 0.25 |
| huAb 0302-L0H1 | 3.54 × 10$^6$ | 3.69 × 10$^{-03}$ | 1.04 |
| huAb 0302-L1H1 | 3.47 × 10$^6$ | 4.04 × 10$^{-03}$ | 1.17 |
| huAb 0302-L2H1 | 1.60 × 10$^6$ | 9.14 × 10$^{-04}$ | 0.57 |
| huAb 0302-L0H2 | 3.40 × 10$^6$ | 1.79 × 10$^{-03}$ | 0.53 |
| huAb 0302-L1H2 | 2.71 × 10$^6$ | 1.53 × 10$^{-03}$ | 0.56 |
| huAb 0302-L2H2 | 1.84 × 10$^6$ | 8.40 × 10$^{-04}$ | 0.46 |
| huAb 0311-L0H1 | 1.22 × 10$^6$ | 5.40 × 10$^{-04}$ | 0.44 |
| huAb 0311-L1H1 | 1.32 × 10$^6$ | 6.64 × 10$^{-04}$ | 0.50 |
| huAb 0311-L0H2 | 1.34 × 10$^6$ | 4.73 × 10$^{-04}$ | 0.35 |
| huAb 0311-L1H2 | 1.51 × 10$^6$ | 6.09 × 10$^{-04}$ | 0.40 |

All but two of the humanized antibodies showed sub-nanomolar binding affinities for human CSF1R ECD, and the remaining two humanized antibodies showed binding affinities for human CSF1R ECD of less than 2 nM.

Example 9

Humanized Anti-CSF1R Antibodies Block Ligand-Induced Phosphorylation

Based on the data above, including CSF1R binding and ligand inhibition, and the likelihood of immunogenicity for each humanized antibody, three humanized antibodies were selected for further study: 0301-L0H0, 0301-L1H0, and 0311-L0H1.

After confirming that 0301-L0H0, 0301-L1H0, and 0311-L0H1 each bind to CSF1R on the surface of cells (data not shown), each of the antibodies was tested for the ability to block ligand-induced CSF1R phosphorylation in CHO cells, as described in Example 6.

Figure 10:
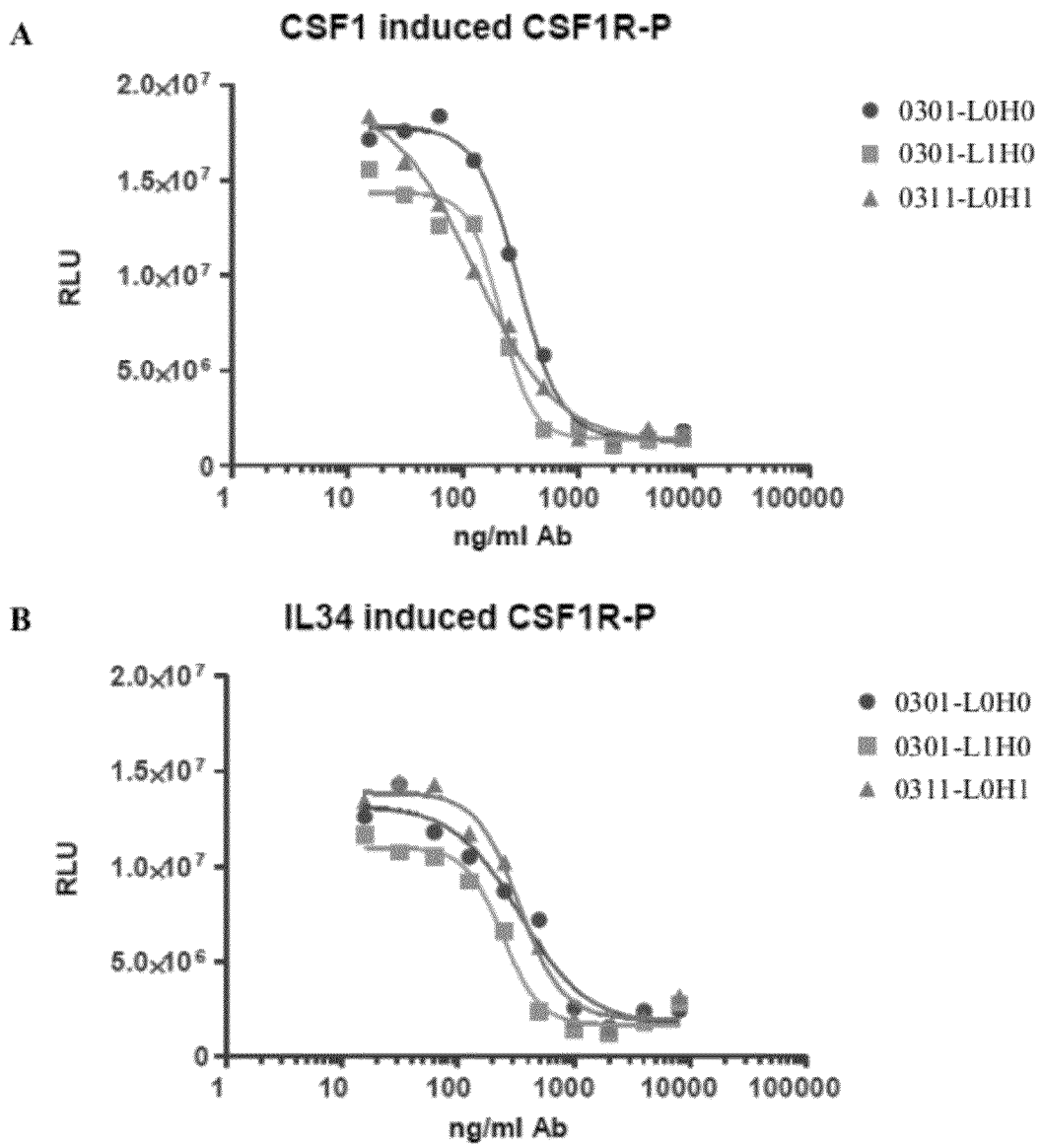
FIGS. 10A and B show blocking of CSF1—(10A) and IL34—(10B) induced CSF1R phosphorylation in CHO cells expressing human CSF1R by humanized antibodies 0301-L0H0, 0301-L1H0, and 0311-L0H1, as described in Example 9.

The results of that experiment are shown in FIG. 10. All three of the humanized antibodies tested blocked both CSF1-induced (A) and IL34-induced (B) phosphorylation of CSF1R in CHO cells. Table 6 shows the IC50 for blocking of ligand-induced CSF1R phosphorylation for each antibody.

TABLE 6

Ligand-induced phosphorylation blocking IC50 for humanized antibodies

| Humanized antibody | CSF1 blocking IC50 (ng/ml) | IL34 blocking IC50 (ng/ml) |
|---|---|---|
| 0301-L0H0 | 305.4 | 340.8 |
| 0301-L1H0 | 213.2 | 242.2 |
| 0311-L0H1 | 127.2 | 337.6 |

Example 10

Humanized Anti-CSF1R Antibodies Block Ligand-Induced Proliferation/Survival Responses of Primary Human Monocytes Humanized antibodies 0301-L0H0, 0301-L1H0, and 0311-L0H1 were tested for their ability to block ligand-induced monocyte proliferation/survival responses as follows.

Human peripheral blood mononuclear cells (PBMCs) were isolated from healthy donor blood by centrifugation onto a Ficoll-Paque cushion (GE Healthcare Bio-Sciences) according to the manufacturer's instructions. Peripheral blood monocytes were subsequently isolated from the recovered PBMC fraction by centrifugation onto a 48.5% Percoll™ cushion (GE Healthcare Bio-Sciences). After recovery from the Percoll™ cushion, the purified peripheral blood monocytes were stimulated with 162 pM recombinant human CSF1 or 1.6 nM recombinant human IL34 (both from R&D Systems) in the presence or absence of serial dilutions of humanised antibody 0301-L0H0, humanised antibody 0301-L1H0, or humanised antibody 0311-L0H1. After incubation at 37° C. for 48 hours, relative cellular ATP content of each individual culture was assessed using CellTiter-Glo® reagent (Promega) according to the manufacturer's instructions. In this assay, relative cellular ATP content is directly proportional to the number of viable cells in culture, and thus reflects monocyte proliferation/survival responses.

Figure 11:
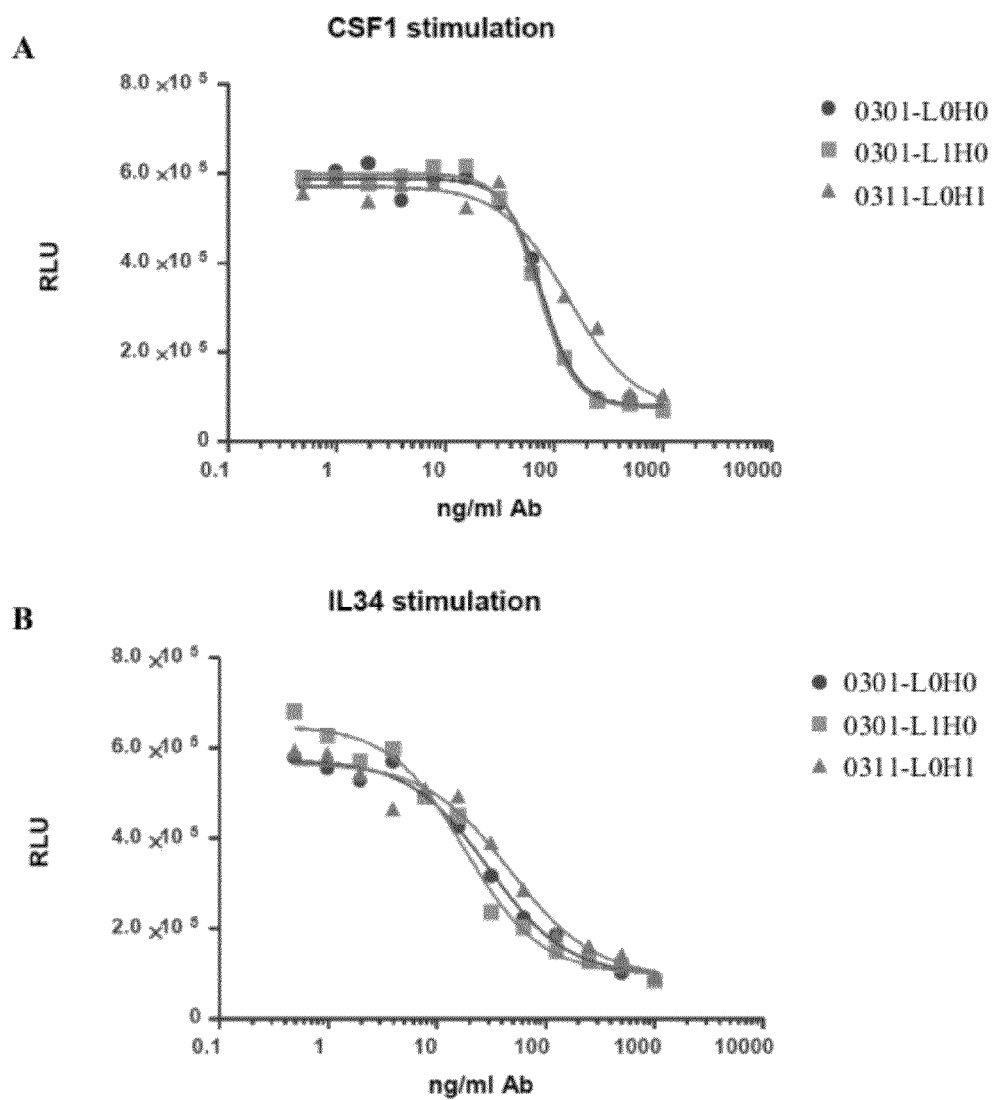
FIGS. 11A and B show blocking of CSF1—(11A) and IL34—(11B) induced monoclyte proliferation/survival responses by humanized antibodies 0301-L0H0, 0301-L1H0, and 0311-L0H1, as described in Example 10.

The results of that experiment are shown in FIG. 11. All three of the humanized antibodies tested were able to block monocyte proliferation/survival responses following CSF1 (A) or IL34 (B) stimulation. Table 7 shows the IC50s for blocking of ligand-induced monocyte proliferation/survival responses for each antibody. The values shown in Table 7 represent the range observed from the three different primary donors tested.

TABLE 7

Monocyte proliferation/survival blocking IC50 for humanized antibodies

| Humanized antibody | CSF1 blocking IC50 (ng/ml) | IL34 blocking IC50 (ng/ml) |
|---|---|---|
| 0301-L0H0 | 31.9-77.5 | 12.2-29.9 |
| 0301-L1H0 | 19.0-71.9 | 10.5-30.6 |
| 0311-L0H1 | 75.9-134.8 | 26.9-152.2 |

Example 11

Humanized Anti-CSF1R Antibodies do not Directly Stimulate Primary Human Monocyte Proliferation or Survival Responses Humanized antibodies 0301-L0H0, 0301-L1H0, and 0311-L0H1 were tested for their ability to directly stimulate primary monocyte proliferation and/or survival, as follows.

Human peripheral blood monocytes were isolated as described in Example 10. Serial dilutions of humanised antibody 0301-L0H0, humanised antibody 0301-L1H0, or humanised antibody 0311-L0H1 were added to the monocytes in the absence of stimulation either by exogenous CSF1 or by exogenous IL34. After incubation at 37° C. for 48 hours, relative ATP content of each individual culture was assessed using CellTiter Glo® reagent (Promega) as in Example 10. The experiment was carried out on peripheral blood monocytes from three different donors.

Figure 12:
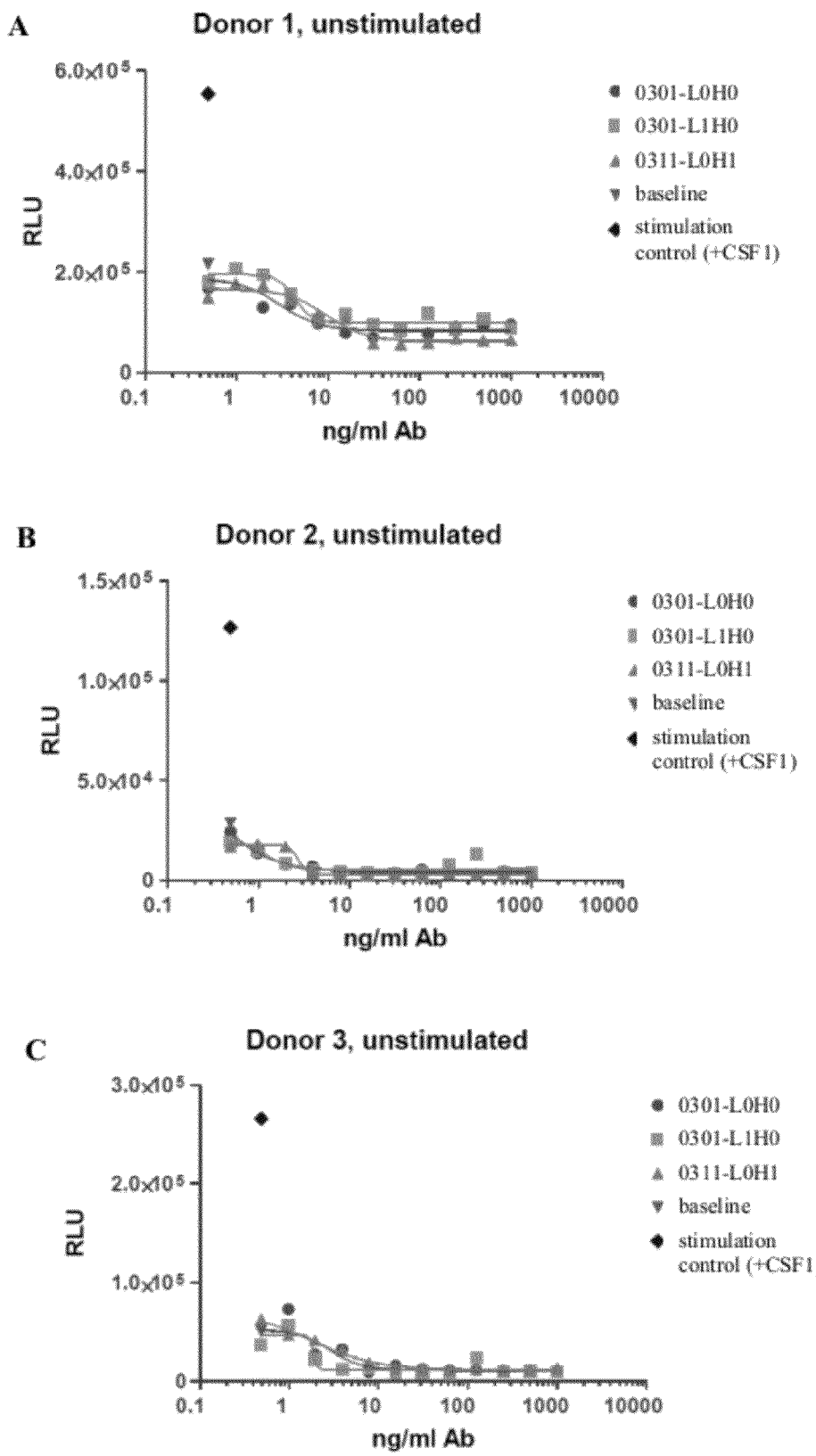
FIGS. 12A-C show that humanized antibodies 0301-L0H0, 0301-L1H0, and 0311-L0H1 do not stimulate primary monocyte proliferation or survival, using monocytes from three different donors, as described in Example 11.

The results of that experiment are shown in FIG. 12. None of the humanized antibodies stimulated primary monocyte proliferation or survival in either of the primary monocyte preparations tested.

TABLE OF SEQUENCES

Table 8 provides certain sequences discussed herein. All polypeptide and antibody sequences are shown without leader sequences, unless otherwise indicated.

TABLE 8

Sequences and Descriptions

| SEQ ID NO | Description | Sequence |
|---|---|---|
| 1 | hCSF1R (full-length, no leader sequence) | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHTHP PDEFLFTPVV VACMSIMALL LLLLLLLYK YKQKPKYQVR WKIIESYEGN SYTFIDPTQL PYNEKWEFPR NNLQFGKTLG AGAFGKVVEA TAFGLGKEDA VLKVAVKMLK STAHADEKEA LMSELKIMSH LGQHENIVNL LGACTHGGPV LVITEYCCYG DLLNFLRRKA EAMLGPSLSP GQDPEGGVDY KNIHLEKKYV RRDSGFSSQG VDTYVEMRPV STSSNDSFSE QDLDKEDGRP LELRDLLHFS SQVAQGMAFL ASKNCIHRDV AARNVLLTNG HVAKIGDFGL ARDIMNDSNY IVKGNARLPV KWMAPESIFD CVYTVQSDVW SYGILLWEIF SLGLNPYPGI LVNSKFYKLV KDGYQMAQPA FAPKNIYSIM QACWALEPTH RPTFQQICSF LQEQAQEDRR ERDYTNLPSS SRSGGSGSSS SELEEESSSE HLTCCEQGDI AQPLLQPNNY QFC |
| 2 | hCSF1R (full-length, + leuler sequence) | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVMSIS IRLKVQKVIP GPPALTLVPA ELVIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHTHPP DEFLFTPVVV ACMSIMALLL LLLLLLYKQ KQKPKYQVRW KIIESYEGNS YTFIDPTQLP YNEKWEFPRN NLQFGKTLGA GAFGKVVEAT AFGLGKEDAV LKVAVKMLKS TAHADEKEAL MSELKIMSHL GQHENIVNLL GACTHGGPVL VITEYCCYGD LLNFLRRKAE AMLGPSLSPG QDPEGGVDYK NIHLEKKYVR RDSGFSSQGV DTYVEMRPVS TSSNDSFSEQ DLDKEDGRPL ELRDLLHFSS QVAQGMAFLA SKNCIHRDVA ARNVLLTNGH VAKIGDFGLA RDIMNDSNYI VKGNARLPVK WMAPESIFDC VYTVQSDVWS YGILLWEIFS LGLNPYPGIL VNSKFYKLVK DGYQMAQPAF APKNIYSIMQ ACWALEPTHR PTFQQICSFL QEQAQEDRRE RDYTNLPSSS RSGGSGSSSE ELEEESSSEH LTCCEQGDIA QPLLQPNNYQ FC |
| 5 | hCSF1R ECD.506 | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAH |
| 6 | hCSF1R ECD.506-Fc | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHEPK SSDKTHTCPP CPAPELLGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSRDEL TKNQVSLTCL VKGFYPSDIA VEWESNGQPE NNYKTTPPVL DSDGSFFLYS KLTVDKSRWQ QGNVFSCSVM HEALHNHYTQ KSLSLSPGK |
| 7 | cyroCSF1R ECD (with leader sequence) | MGPGVLLLLL VVTAWHGQG PVIEPSGPEL VVKPGETVTL RCVGNGSVEW DGPISPHWTL YSDGPSSVLT TNNATFQNTR TYRCTEPGDP LGGSAAIHLY VKDPARPWNV LAKEVVVFED QDALLPCLLT DPVLEAGVSL VRLRGRPLLR HTNYSFSPWH GFTIHRAKFI QGQDYQCSAL MGSRKVMSIS IRLKVQKVIP |

TABLE 8-continued

Sequences and Descriptions

| SEQ ID NO | Description | Sequence |
|---|---|---|
| | | GPPALTLVPA ELVRIRGEAA QIVCSASNID VDFDVFLQHN TTKLAIPQRS DFHDNRYQKV LTLSLGQVDF QHAGNYSCVA SNVQGKHSTS MFFRVVESAY LDLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTS INGSGTLLCA ASGYPQPNVT WLQCAGHTDR CDEAQVLQVW VDPHPEVLSQ EPFQKVTVQS LLTAETLEHN QTYECRAHNS VGSGSWAFIP ISAGAR |
| 8 | cynoCSF1R ECD-Fc (with leader sequence) | MGPGVLLLLL VVTAWHGQGI PVIEPSGPEL VVKPGETVTL RCVGNGSVEW DGPISPHWTL YSDGPSSVLT TTNATFQNTR TYRCTEPGDP LGGSAAIHLY VKDPARPWNV LAKEVVVFED QDALLPCLLT DPVLEAGVSL VRLRGRPLLR HTNYSFSPWH GFTIHRAKFI QGQDYQCSAL MGSRKVMSIS IRLKVQKVIP GPPALTLVPA ELVRIRGEAA QIVCSASNID VDFDVFLQHN TTKLAIPQRS DFHDNRYQKV LTLSLGQVDF QHAGNYSCVA SNVQGKHSTS MFFRVVESAY LDLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTS INGSGTLLCA ASGYPQPNVT WLQCAGHTDR CDEAQVLQVW VDPHPEVLSQ EPFQKVTVQS LLTAETLEHN QTYECRAHNS VGSGSWAFIP ISAGARGSEP KSSDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 3 | Light chain leader sequence | METDTLLLWV LLLWVPGSTG |
| 4 | Heavy chain leader sequence | MAVLGLLLCL VTFPSCVLS |
| 9 | Fab 0301 heavy chain variable region | EVQLQQSGPE LVRPGASVKM SCKASGYTFT DNYMIWVKQS HGKSLEWIGD INPYNGGTTF NQKFKGKATL TVEKSSSTAY MQLNSLTSED SAVYYCARES PYFSNLYVMD YWGQGTSVTV SS |
| 10 | Fab 0301 light chain variable region | NIVLTQSPAS LAVSLGQRAT ISCKASQSVD YDGDNYMNWY QQKPGQPPKL LIYAASNLES GIPARFSGSG SGTDFTLNIH PVEEEDAATY YCHLSNEDLS TFGGGTKLEI K |
| 11 | Fab 0302 heavy chain variable region | EIQLQQSGPE LVKPGASVKM SCKASGYTFS DFNIHWVKQK PGQGLEWIGY INPYTDVTVY NEKFKGKATL TSDRSSSTAY MDLSSLTSED SAVYYCASYF DGTFDYALDY WGQGTSITVS S |
| 12 | Fab 0302 light chain variable region | DVVVTQTPAS LAVSLGQRAT ISCRASESVD NYGLSFMNWF QQKPGQPPKL LIYTASNLES GIPARFSGGG SRTDFTLTID PVEADDAATY FCQQSKELPW TFGGGTRLEI K |
| 13 | Fab 0311 heavy chain variable region | EIQLQQSGPD LMKPGASVKM SCKASGYIFT DYNMHWVKQN QGKSLEWMGE INPNNGVVVY NQKFKGTTTL TVDKSSSTAY MDLHSLTSED SAVYYCTRAL YHSNFGWYFD SWGKGTTLTV SS |
| 14 | Fab 0311 light chain variable region | DIVLTQSPAS LAVSLGQRAT ISCKASQSVD YDGDSHMNWY QQKPGQPPKL LIYTASNLES GIPARFSGSG SGADFTLTIH PVEEEDAATY YCQQGNEDPW TFGGGTRLEI K |
| 15 | 0301 heavy chain CDR1 | GYTFTDNYMI |
| 16 | 0301 heavy chain CDR2 | DINPYNGGTT FNQKFKG |
| 17 | 0301 heavy chain CDR3 | ESPYFSNLYV MDY |
| 18 | 0301 light chain CDR1 | KASQSVDYDG DNYMN |

TABLE 8-continued

Sequences and Descriptions

| SEQ ID NO | Description | Sequence |
|---|---|---|
| 19 | 0301 light chain CDR2 | AASNLES |
| 20 | 0301 light chain CDR3 | HLSNEDLST |
| 21 | 0302 heavy chain CDR1 | GYTFSDFNIH |
| 22 | 0302 heavy chain CDR2 | YINPYTDVTV YNEKFKG |
| 23 | 0302 heavy chain CDR3 | YFDGTFDYAL DY |
| 24 | 0302 light chain CDR1 | RASESVDNYG LSFMN |
| 25 | 0302 light chain CDR2 | TASNLES |
| 26 | 0302 light chain CDR3 | QQSKELPWT |
| 27 | 0311 heavy chain CDR1 | GYIFTDYNMH |
| 28 | 0311 heavy chain CDR2 | EINPNNGVVV YNQKFKG |
| 29 | 0311 heavy chain CDR3 | ALYHSNFGWY FDS |
| 30 | 0311 light chain CDR1 | KASQSVDYDG DSHMN |
| 31 | 0311 light chain CDR2 | TASNLES |
| 32 | 0311 light chain CDR3 | QQGNEDPWT |
| 33 | cAb 0301 heavy chain | EVQLQQSGPE LVRPGASVKM SCKASGYTFT DNYMIWVKQS HGKSLEWIGD INPYNGGTTF NQKFKGKATL TVEKSSSTAY MQLNSLTSED SAVYYCARES PYFSNLYVMD YWGQGTSVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 34 | cAb 0301 light chain | NIVLTQSPAS LAVSLGQRAT ISCKASQSVD YDGDNYMNWY QQKPGQPPKL LIYAASNLES GIPARFSGSG SGTDFTLNIH PVEEEDAATY YCHLSNEDLS TFGGGTKLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 35 | cAb 0302 heavy chain | EIQLQQSGPE LVKPGASVKM SCKASGYTFS DFNIHWVKQK PGQGLEWIGY INPYTDVTVY NEKFKGKATL TSDRSSSTAY MDLSSLTSED SAVYYCASYF DGTFDYALDY WGQGTSITVS SASTKGPSVF PLAPCSRSTS ESTAALGCLV KDYFPEPVTV SWNSGALTSG VHTFPAVLQS SGLYSLSSVV TVPSSSLGTK TYTCNVDHKP SNTKVDKRVE SKYGPPCPPC PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK |
| 36 | cAb 0302 light chain | DVVVTQTPAS LAVSLGQRAT ISCRASESVD NYGLSFMNWF QQKPGQPPKL LIYTASNLES GIPARFSGGG SRTDFTLTID PVEADDAATY FCQQSKELPW TFGGGTRLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |

TABLE 8-continued

Sequences and Descriptions

| SEQ ID NO | Description | Sequence |
|---|---|---|
| 37 | cAb 0311 heavy chain | EIQLQQSGPD LMKPGASVKM SCKASGYIFT DYNMHWVKQN QGKSLEWMGE INPNNGVVVY NQKFKGTTTL TVDKSSSTAY MDLHSLTSED SAVYYCTRAL YHSNFGWYFD SWGKGTTLTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 38 | cAb 0311 light chain | DIVLTQSPAS LAVSLGQRAT ISCKASQSVD YDGDSHMNWY QQKPGQPPKL LIYTASNLES GIPARFSGSG SGADFTLTIH PVEEEDAATY YCQQGNEDPW TFGGGTRLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 39 | h0301-H0 heavy chain variable region | QVQLVQSGAE VKKPGSSVKV SCKASGYTFT DNYMIWVRQA PGQGLEWMGD INPYNGGTTF NQKFKGRVTI TADKSTSTAY MELSSLRSED TAVYYCARES PYFSNLYVMD YWGQGTLVTV SS |
| 40 | h0301-H1 heavy chain variable region | QVQLVQSGAE VKKPGSSVKV SCKASGYTFT DNYMIWVRQA PGQGLEWMGD INPYNGGTTF NQKFKGRVTI TVDKSTSTAY MELSSLRSED TAVYYCARES PYFSNLYVMD YWGQGTLVTV SS |
| 41 | h0301-H2 heavy chain variable region | QVQLVQSGAE VKKPGSSVKV SCKASGYTFT DNYMIWVRQA PGQGLEWIGD INPYNGGTTF NQKFKGRATL TVDKSTSTAY MELSSLRSED TAVYYCARES PYFSNLYVMD YWGQGTLVTV SS |
| 42 | H0302-H1 heavy chain variable region | QVQLVQSGAE VKKPGSSVKV SCKASGYTFS DFNIHWVRQA PGQGLEWMGY INPYTDVTVY NEKFKGRVTI TSDKSTSTAY MELSSLRSED TAVYYCASYF DGTFDYALDY WGQGTLVTVS S |
| 43 | H0302-H2 heavy chain variable region | QVQLVQSGAE VKKPGSSVKV SCKASGYTFS DFNIHWVRQA PGQGLEWIGY INPYTDVTVY NEKFKGRATL TSDKSTSTAY MELSSLRSED TAVYYCASYF DGTFDYALDY WGQGTLVTVS S |
| 44 | H0311-H1 heavy chain variable region | QVQLVQSGAE VKKPGSSVKV SCKASGYIFT DYNMHWVRQA PGQGLEWMGE INPNNGVVVY NQKFKGRVTI TVDKSTSTAY MELSSLRSED TAVYYCTRAL YHSNFGWYFD SWGQGTLVTV SS |
| 45 | H0311-H2 heavy chain variable region | QVQLVQSGAE VKKPGSSVKV SCKASGYIFT DYNMHWVRQA PGQGLEWMGE INPNNGVVVY NQKFKGTTTL TVDKSTSTAY MELSSLRSED TAVYYCTRAL YHSNFGWYFD SWGQGTLVTV SS |
| 46 | h0301-L0 light chain variable region | EIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS TFGGGTKVEI K |
| 47 | h0301-L1 light chain variable region | NIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS TFGGGTKVEI K |
| 48 | H0302-L0 light chain variable region | EIVLTQSPAT LSLSPGERAT LSCRASESVD NYGLSFMNWY QQKPGQAPRL LIYTASNLES GIPARFSGSG SGTDFTLTIS SLEPEDFAVY YCQQSKELPW TFGQGTKVEI K |
| 49 | H0302-L1 light chain variable region | EIVLTQSPAT LSLSPGERAT LSCRASESVD NYGLSFMNWY QQKPGQAPRL LIYTASNLES GIPARFSGSG SRTDFTLTIS SLEPEDFAVY YCQQSKELPW TFGQGTKVEI K |
| 50 | H0302-L2 light chain | EIVVTQSPAT LSLSPGERAT LSCRASESVD NYGLSFMNWF QQKPGQAPRL LIYTASNLES GIPARFSGSG SRTDFTLTIS SLEPEDFAVY YCQQSKELPW |

TABLE 8-continued

Sequences and Descriptions

| SEQ ID NO | Description | Sequence |
|---|---|---|
| | variable region | TFGQGTKVEI K |
| 51 | H0311-L0 light chain variable region | EIVLTQSPAT LSLSPGERAT LSCKASQSVD YDGDSHMNWY QQKPGQAPRL LIYTASNLES GIPARFSGSG SGTDFTLTIS SLEPEDFAVY YCQQGNEDPW TFGQGTKVEI K |
| 52 | H0311-L1 light chain variable region | DIVLTQSPAT LSLSPGERAT LSCKASQSVD YDGDSHMNWY QQKPGQAPRL LIYTASNLES GIPARFSGSG SGADFTLTIS SLEPEDFAVY YCQQGNEDPW TFGQGTKVEI K |
| 53 | h0301-H0 heavy chain | QVQLVQSGAE VKKPGSSVKV SCKASGYTFT DNYMIWVRQA PGQGLEWMGD INPYNGGTTF NQKFKGRVTI TADKSTSTAY MELSSLRSED TAVYYCARES PYFSNLYVMD YWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 54 | h0301-H1 heavy chain | QVQLVQSGAE VKKPGSSVKV SCKASGYTFT DNYMIWVRQA PGQGLEWMGD INPYNGGTTF NQKFKGRVTI TVDKSTSTAY MELSSLRSED TAVYYCARES PYFSNLYVMD YWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 55 | h0301-H2 heavy chain | QVQLVQSGAE VKKPGSSVKV SCKASGYTFT DNYMIWVRQA PGQGLEWIGD INPYNGGTTF NQKFKGRATL TVDKSTSTAY MELSSLRSED TAVYYCARES PYFSNLYVMD YWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 56 | H0302-H1 heavy chain | QVQLVQSGAE VKKPGSSVKV SCKASGYTFS DFNIHWVRQA PGQGLEWMGY INPYTDVTVY NEKFKGRVTI TSDKSTSTAY MELSSLRSED TAVYYCASYF DGTFDYALDY WGQGTLVTVS SASTKGPSVF PLAPCSRSTS ESTAALGCLV KDYFPEPVTV SWNSGALTSG VHTFPAVLQS SGLYSLSSVV TVPSSSLGTK TYTCNVDHKP SNTKVDKRVE SKYGPPCPPC PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK |
| 57 | H0302-H2 heavy chain | QVQLVQSGAE VKKPGSSVKV SCKASGYTFS DFNIHWVRQA PGQGLEWIGY INPYTDVTVY NEKFKGRATL TSDKSTSTAY MELSSLRSED TAVYYCASYF DGTFDYALDY WGQGTLVTVS SASTKGPSVF PLAPCSRSTS ESTAALGCLV KDYFPEPVTV SWNSGALTSG VHTFPAVLQS SGLYSLSSVV TVPSSSLGTK TYTCNVDHKP SNTKVDKRVE SKYGPPCPPC PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK |
| 58 | H0311-H1 heavy chain | QVQLVQSGAE VKKPGSSVKV SCKASGYIFT DYNMHWVRQA PGQGLEWMGE INPNNGVVVY NQKFKGRVTI TVDKSTSTAY MELSSLRSED TAVYYCTRAL YHSNFGWYFD SWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 59 | H0311-H2 heavy chain | QVQLVQSGAE VKKPGSSVKV SCKASGYIFT DYNMHWVRQA PGQGLEWMGE INPNNGVVVY NQKFKGTTTL TVDKSTSTAY MELSSLRSED TAVYYCTRAL |

TABLE 8-continued

Sequences and Descriptions

| SEQ ID NO | Description | Sequence |
|---|---|---|
| | | YHSNFGWYFD SWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 60 | h0301-L0 light chain | EIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS TFGGGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 61 | h0301-L1 light chain | NIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS TFGGGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 62 | H0302-L0 light chain | EIVLTQSPAT LSLSPGERAT LSCRASESVD NYGLSFMNWY QQKPGQAPRL LIYTASNLES GIPARFSGSG SGTDFTLTIS SLEPEDFAVY YCQQSKELPW TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 63 | H0302-L1 light chant | EIVLTQSPAT LSLSPGERAT LSCRASESVD NYGLSFMNWY QQKPGQAPRL LIYTASNLES GIPARFSGSG SRTDFTLTIS SLEPEDFAVY YCQQSKELPW TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 64 | H0302-L2 light chain | EIVVTQSPAT LSLSPGERAT LSCRASESVD NYGLSFMNWF QQKPGQAPRL LIYTASNLES GIPARFSGSG SRTDFTLTIS SLEPEDFAVY YCQQSKELPW TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 65 | H0311-L0 light chain | EIVLTQSPAT LSLSPGERAT LSCKASQSVD YDGDSHMNWY QQKPGQAPRL LIYTASNLES GIPARFSGSG TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 66 | H0311-L1 light chain | DIVLTQSPAT LSLSPGERAT LSCKASQSVD YDGDSHMNWY QQKPGQAPRL LIYTASNLES GIPARFSGSG SGADFTLTIS SLEPEDFAVY YCQQGNEDPW TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 67 | Human CSF1 | EEVSEYCSHM IGSGHLQSLQ RLIDSQMETS CQITFEFVDQ EQLKDPVCYL KKAFLLVQDI MEDTMRFRDN TPNAIAIVQL QELSLRLKSC FTKDYEEHDK ACVRTFYETP LQLLEKVKNV FNETKNLLDK DWNIFSKNCN NSFAECSSQG HERQSEGS |
| 68 | Human IL34 | NEPLEMWPLT QNEECTVTGF LRDKLQYRSR LQYMKHYFPI NYKISVPYEG VFRIANVTRL QRAQVSEREL RYLWVLVSLSATESVQDVLL EGHPSWKYLQ EVQTLLLNVQ QGLTDVEVSP KVESVLSLLN APGPNLKLVR PKALLDNCFR VMELLYCSCC KQSSVLNWQD CEVPSPQSCS PEPSLQYAAT QLYPPPPWSP SSPPHSTGSV RPVRAQGEGL LP |
| 69 | Human acceptor A FR1 | QVQLVQSGAE VKKPGSSVKV SCKAS |
| 70 | Human acceptor A FR2 | WVRQAPGQGL EWMG |
| 71 | Human acceptor A FR3 | RVTITADKST STAYMELSSL RSEDTAVYYC AR |

TABLE 8-continued

Sequences and Descriptions

| SEQ ID NO | Description | Sequence |
|---|---|---|
| 72 | Human acceptor A FR4 | WGQGTLVTVS S |
| 73 | Human acceptor B FR1 | QVQLVQSGAE VKKPGSSVKV SCKAS |
| 74 | Human acceptor B FR2 | WVRQAPGQGL EWMG |
| 75 | Human acceptor B FR3 | RVTITADKST STAYMELSSL RSEDTAVYYC AR |
| 76 | Human acceptor B FR4 | WGQGTLVTVSS |
| 77 | Human acceptor C FR1 | QVQLVQSGAE VKKPGSSVKV SCKAS |
| 78 | Human acceptor C FR2 | WVRQAPGQGL EWMG |
| 79 | Human acceptor C FR3 | RVTITADKST STAYMELSSL RSEDTAVYYC AR |
| 80 | Human acceptor C FR4 | WGQGTLVTVS S |
| 81 | Human acceptor D FR1 | EIVLTQSPAT LSLSPGERAT LSC |
| 82 | Human acceptor D FR2 | WYQQKPGQAP RLLIY |
| 83 | Human acceptor D FR3 | GIPARFSGSG SGTDFTLTIS SLEPEDFAVY YC |
| 84 | Human acceptor D FR4 | FGGGTKVEIK |
| 85 | Human acceptor E FR1 | EIVLTQSPAT LSLSPGERAT LSC |
| 86 | Human acceptor E FR2 | WYQQKPGQAP RLLIY |
| 87 | Human acceptor E FR3 | GIPARFSGSG SGTDFTLTIS SLEPEDFAVY YC |
| 88 | Human acceptor E FR4 | FGQGTKVEIK |
| 89 | Human acceptor F FR1 | EIVLTQSPAT LSLSPGERAT LSC |

TABLE 8-continued

Sequences and Descriptions

| SEQ ID NO | Description | Sequence |
|---|---|---|
| 90 | Human acceptor F FR2 | WYQQKPGQAP RLLIY |
| 91 | Human acceptor F FR3 | GIPARFSGSG SGTDFTLTIS SLEPEDFAVY YC |
| 92 | Human acceptor F FR4 | FGQGTKVEIK |
| 93 | mCSF1R ECD-Fc | APVIEPSGPE LVVEPGETVT LRCVSNGSVE WDGPISPYWT LDPESPGSTL TTRNATFKNT GTYRCTELED PMAGSTTIHL YVKDPAHSWN LLAQEVTVVE GQEAVLPCLI TDPALKDSVS LMREGGRQVL RKTVYFFSPW RGFIIRKAKV LDSNTYVCKT MVNGRESTST GIWLKVNRVH PEPPQIKLEP SKLVRIRGEA AQIVCSATNA EVGFNVILKR GDTKLEIPLN SDFQDNYYKK VRALSLNAVD FQDAGIYSCV ASNDVGTRTA TMNFQVVESA YLNLTSEQSL LQEVSVGDSL ILTVHADAYP SIQHYNWTYL GPFFEDQRKL EFITQRAIYR YTFKLFLNRV KASEAGQYFL MAQNKAGWNN LTFELTLRYP PEVSVTWMPV NGSDVLFCDV SGYPQPSVTW MECRGHTDRC DEAQALQVWN DTHPEVLSQK PFDKVIIQSQ LPIGTLKHNM TYFCKTHNSV GNSSQYFRAV SLGQSKQEPK SSDKTHTCPP CPAPELLGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSRDEL TKNQVSLTCL VKGFYPSDIA VEWESNGQPE NNYKTTPPVL DSDGSFFLYS KLTVDKSRWQ QGNVFSCSVM HEALHNHYTQ KSLSLSPGK |
| 94 | Human IgG4S241P | ASTKGPSVFP LAPCSRSTSE STAALGCLVK DYFPEPVTVS WNSGALTSGV HTFPAVLQSS GLYSLSSVVT VPSSSLGTKT YTCNVDHKPS NTKVDKRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGK |
| 95 | Human Igκ | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |

The invention claimed is:

1. A method of treating a condition selected from multiple sclerosis, rheumatoid arthritis, osteolytic bone loss, systemic lupus erythematosus, and cancer comprising administering to a patient a pharmaceutical composition comprising an antibody that binds colony stimulating factor 1 receptor (CSF1R), wherein the antibody is selected from:

a) an antibody comprising a heavy chain comprising the sequence of SEQ ID NO: 39 and a light chain comprising the sequence of SEQ ID NO: 46;

b) an antibody comprising a heavy chain comprising a heavy chain (HC) CDR1 having the sequence of SEQ ID NO: 15, an HC CDR2 having the sequence of SEQ ID NO: 16, and an HC CDR3 having the sequence of SEQ ID NO: 17, and a light chain comprising a light chain (LC) CDR1 having the sequence of SEQ ID NO: 18, a LC CDR2 having the sequence of SEQ ID NO: 19, and a LC CDR3 having the sequence of SEQ ID NO: 20; and c) an antibody comprising a heavy chain comprising the sequence of SEQ ID NO: 53 and a light chain comprising the sequence of SEQ ID NO: 60.

2. The method of claim 1, wherein the antibody is a humanized antibody.

3. The method of claim 1, wherein the antibody is selected from a Fab, an Fv, an scFv, a Fab', and a (Fab')$_2$.

4. The method of claim 1, wherein the condition is multiple sclerosis.

5. The method of claim 4, wherein the method further comprises administering at least one additional therapeutic agent selected from interferon alpha, interferon beta, prednisone, an anti-alpha4 integrin antibody, an anti-CD20 antibody, fingolimod, and cladribine.

6. The method of claim 1, wherein the condition is rheumatoid arthritis.

7. The method of claim 6, wherein the method further comprises administering at least one additional therapeutic agent selected from methotrexate, an anti-TNF agent, a glucocorticoid, leflunomide, azathioprine, a JAK inhibitor, a SYK inhibitor, an anti-IL-6 antibody, an anti-IL-6R antibody, an anti-CD-20 antibody, an anti-CD19 antibody, an anti-GM-CSF antibody, and an anti-GM-CSF-R antibody.

8. The method of claim 1, wherein the condition is osteolytic bone loss.

9. The method of claim 8, wherein the osteolytic bone loss is selected from osteoporosis, metastasis-induced osteolytic bone loss, and rheumatoid arthritis-induced bone loss.

10. The method of claim 1, wherein the condition is systemic lupus erythematosus.

11. The method of claim 1, wherein the condition is cancer.

12. The method of claim 11, wherein the cancer is selected from breast cancer, prostate cancer, endometrial cancer, bladder cancer, kidney cancer, esophageal cancer, squamous cell carcinoma, uveal melanoma, follicular lymphoma, renal cell carcinoma, cervical cancer, ovarian cancer, lung cancer, colorectal cancer, brain cancer, pancreatic cancer, head and neck cancer, liver cancer, leukemia, lymphoma, Hodgkin's disease, multiple myeloma, melanoma, astrocytoma, stomach cancer, and pulmonary adenocarcinoma.

13. The method of claim 11, wherein the cancer is a solid tumor.

* * * * *

SEQUENCE LISTING

```
<160> NUMBER OF SEQ ID NOS: 95

<210> SEQ ID NO 1
<211> LENGTH: 953
<212> TYPE: PRT
<213> ORGANISM: Homo sapiens
<220> FEATURE:
<221> NAME/KEY: misc_feature
<222> LOCATION: (1)..(953)
<223> OTHER INFORMATION: hCSF1R (full-length, no leader sequence)

<400> SEQUENCE: 1
```

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

```
Cys Thr Glu Pro Gly Asp Pro Leu Gly Gly Ser Ala Ala Ile His Leu
 65                  70                  75                  80

Tyr Val Lys Asp Pro Ala Arg Pro Trp Asn Val Leu Ala Gln Glu Val
                 85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
    290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
    370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
        435                 440                 445

Val Gln Ser Leu Leu Thr Val Glu Thr Leu Glu His Asn Gln Thr Tyr
    450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu Phe Leu Phe
                485                 490                 495
```

```
Thr Pro Val Val Val Ala Cys Met Ser Ile Met Ala Leu Leu Leu Leu
            500                 505                 510

Leu Leu Leu Leu Leu Leu Tyr Lys Tyr Lys Gln Lys Pro Lys Tyr Gln
        515                 520                 525

Val Arg Trp Lys Ile Ile Glu Ser Tyr Glu Gly Asn Ser Tyr Thr Phe
    530                 535                 540

Ile Asp Pro Thr Gln Leu Pro Tyr Asn Glu Lys Trp Glu Phe Pro Arg
545                 550                 555                 560

Asn Asn Leu Gln Phe Gly Lys Thr Leu Gly Ala Gly Ala Phe Gly Lys
                565                 570                 575

Val Val Glu Ala Thr Ala Phe Gly Leu Gly Lys Glu Asp Ala Val Leu
            580                 585                 590

Lys Val Ala Val Lys Met Leu Lys Ser Thr Ala His Ala Asp Glu Lys
        595                 600                 605

Glu Ala Leu Met Ser Glu Leu Lys Ile Met Ser His Leu Gly Gln His
    610                 615                 620

Glu Asn Ile Val Asn Leu Leu Gly Ala Cys Thr His Gly Gly Pro Val
625                 630                 635                 640

Leu Val Ile Thr Glu Tyr Cys Cys Tyr Gly Asp Leu Leu Asn Phe Leu
                645                 650                 655

Arg Arg Lys Ala Glu Ala Met Leu Gly Pro Ser Leu Ser Pro Gly Gln
            660                 665                 670

Asp Pro Glu Gly Gly Val Asp Tyr Lys Asn Ile His Leu Glu Lys Lys
        675                 680                 685

Tyr Val Arg Arg Asp Ser Gly Phe Ser Ser Gln Gly Val Asp Thr Tyr
    690                 695                 700

Val Glu Met Arg Pro Val Ser Thr Ser Ser Asn Asp Ser Phe Ser Glu
705                 710                 715                 720

Gln Asp Leu Asp Lys Glu Asp Gly Arg Pro Leu Glu Leu Arg Asp Leu
                725                 730                 735

Leu His Phe Ser Ser Gln Val Ala Gln Gly Met Ala Phe Leu Ala Ser
            740                 745                 750

Lys Asn Cys Ile His Arg Asp Val Ala Ala Arg Asn Val Leu Leu Thr
        755                 760                 765

Asn Gly His Val Ala Lys Ile Gly Asp Phe Gly Leu Ala Arg Asp Ile
    770                 775                 780

Met Asn Asp Ser Asn Tyr Ile Val Lys Gly Asn Ala Arg Leu Pro Val
785                 790                 795                 800

Lys Trp Met Ala Pro Glu Ser Ile Phe Asp Cys Val Tyr Thr Val Gln
                805                 810                 815

Ser Asp Val Trp Ser Tyr Gly Ile Leu Leu Trp Glu Ile Phe Ser Leu
            820                 825                 830

Gly Leu Asn Pro Tyr Pro Gly Ile Leu Val Asn Ser Lys Phe Tyr Lys
        835                 840                 845

Leu Val Lys Asp Gly Tyr Gln Met Ala Gln Pro Ala Phe Ala Pro Lys
    850                 855                 860

Asn Ile Tyr Ser Ile Met Gln Ala Cys Trp Ala Leu Glu Pro Thr His
865                 870                 875                 880

Arg Pro Thr Phe Gln Gln Ile Cys Ser Phe Leu Gln Glu Gln Ala Gln
                885                 890                 895

Glu Asp Arg Arg Glu Arg Asp Tyr Thr Asn Leu Pro Ser Ser Ser Arg
            900                 905                 910

Ser Gly Gly Ser Gly Ser Ser Ser Ser Glu Leu Glu Glu Glu Ser Ser
```

-continued

```
                915                 920                 925
Ser Glu His Leu Thr Cys Cys Glu Gln Gly Asp Ile Ala Gln Pro Leu
930                 935                 940

Leu Gln Pro Asn Asn Tyr Gln Phe Cys
945                 950

<210> SEQ ID NO 2
<211> LENGTH: 972
<212> TYPE: PRT
<213> ORGANISM: Homo sapiens
<220> FEATURE:
<221> NAME/KEY: misc_feature
<222> LOCATION: (1)..(972)
<223> OTHER INFORMATION: hCSF1R (full-length, + leader sequence)

<400> SEQUENCE: 2

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320
```

```
Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
        515                 520                 525

Leu Leu Leu Leu Leu Leu Leu Leu Tyr Lys Tyr Lys Gln Lys Pro
    530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
    610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
        675                 680                 685

Pro Gly Gln Asp Pro Glu Gly Gly Val Asp Tyr Lys Asn Ile His Leu
    690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750
```

```
Arg Asp Leu Leu His Phe Ser Ser Gln Val Ala Gln Gly Met Ala Phe
        755                 760                 765

Leu Ala Ser Lys Asn Cys Ile His Arg Asp Val Ala Ala Arg Asn Val
    770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
    850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
        915                 920                 925

Ser Ser Arg Ser Gly Gly Ser Gly Ser Ser Ser Glu Leu Glu Glu
    930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970

<210> SEQ ID NO 3
<211> LENGTH: 20
<212> TYPE: PRT
<213> ORGANISM: Mus musculus
<220> FEATURE:
<221> NAME/KEY: misc_feature
<222> LOCATION: (1)..(20)
<223> OTHER INFORMATION: Light chain leader sequence

<400> SEQUENCE: 3

Met Glu Thr Asp Thr Leu Leu Leu Trp Val Leu Leu Leu Trp Val Pro
1               5                   10                  15

Gly Ser Thr Gly
            20

<210> SEQ ID NO 4
<211> LENGTH: 19
<212> TYPE: PRT
<213> ORGANISM: Mus musculus
<220> FEATURE:
<221> NAME/KEY: misc_feature
<222> LOCATION: (1)..(19)
<223> OTHER INFORMATION: Heavy chain leader sequence

<400> SEQUENCE: 4

Met Ala Val Leu Gly Leu Leu Leu Cys Leu Val Thr Phe Pro Ser Cys
1               5                   10                  15

Val Leu Ser

<210> SEQ ID NO 5
```

```
<211> LENGTH: 487
<212> TYPE: PRT
<213> ORGANISM: Homo sapiens
<220> FEATURE:
<221> NAME/KEY: misc_feature
<222> LOCATION: (1)..(487)
<223> OTHER INFORMATION: hCSF1R ECD.506

<400> SEQUENCE: 5

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
        50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
```

```
                    370                 375                 380
Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
                420                 425                 430

Asp Pro Tyr Pro Glu Val Leu Ser Gln Glu Pro Phe His Lys Val Thr
            435                 440                 445

Val Gln Ser Leu Leu Thr Val Glu Thr Leu Glu His Asn Gln Thr Tyr
            450                 455                 460

Glu Cys Arg Ala His Asn Ser Val Gly Ser Gly Ser Trp Ala Phe Ile
465                 470                 475                 480

Pro Ile Ser Ala Gly Ala His
                485

<210> SEQ ID NO 6
<211> LENGTH: 719
<212> TYPE: PRT
<213> ORGANISM: Homo sapiens
<220> FEATURE:
<221> NAME/KEY: misc_feature
<222> LOCATION: (1)..(719)
<223> OTHER INFORMATION: hCSF1R ECD.506-Fc

<400> SEQUENCE: 6

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
        50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240
```

```
Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
    290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
                340                 345                 350

Lys Pro Ser Glu Ala Gly Arg Tyr Ser Phe Leu Ala Arg Asn Pro Gly
            355                 360                 365

Gly Trp Arg Ala Leu Thr Phe Glu Leu Thr Leu Arg Tyr Pro Pro Glu
        370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
                420                 425                 430

Asp Pro Tyr Pro Glu Val Leu Ser Gln Glu Pro Phe His Lys Val Thr
            435                 440                 445

Val Gln Ser Leu Leu Thr Val Glu Thr Leu Glu His Asn Gln Thr Tyr
        450                 455                 460

Glu Cys Arg Ala His Asn Ser Val Gly Ser Gly Ser Trp Ala Phe Ile
465                 470                 475                 480

Pro Ile Ser Ala Gly Ala His Glu Pro Lys Ser Ser Asp Lys Thr His
                485                 490                 495

Thr Cys Pro Pro Cys Pro Ala Pro Glu Leu Leu Gly Gly Pro Ser Val
                500                 505                 510

Phe Leu Phe Pro Pro Lys Pro Lys Asp Thr Leu Met Ile Ser Arg Thr
            515                 520                 525

Pro Glu Val Thr Cys Val Val Val Asp Val Ser His Glu Asp Pro Glu
        530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
                580                 585                 590

Cys Lys Val Ser Asn Lys Ala Leu Pro Ala Pro Ile Glu Lys Thr Ile
            595                 600                 605

Ser Lys Ala Lys Gly Gln Pro Arg Glu Pro Gln Val Tyr Thr Leu Pro
        610                 615                 620

Pro Ser Arg Asp Glu Leu Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
                660                 665                 670
```

-continued

```
Asp Gly Ser Phe Phe Leu Tyr Ser Lys Leu Thr Val Asp Lys Ser Arg
        675                 680                 685

Trp Gln Gln Gly Asn Val Phe Ser Cys Ser Val Met His Glu Ala Leu
690                 695                 700

His Asn His Tyr Thr Gln Lys Ser Leu Ser Leu Ser Pro Gly Lys
705                 710                 715

<210> SEQ ID NO 7
<211> LENGTH: 506
<212> TYPE: PRT
<213> ORGANISM: Macaca cynomolgus
<220> FEATURE:
<221> NAME/KEY: misc_feature
<222> LOCATION: (1)..(506)
<223> OTHER INFORMATION: cynoCSF1R ECD (with leader sequence)

<400> SEQUENCE: 7

Met Gly Pro Gly Val Leu Leu Leu Leu Val Val Thr Ala Trp His
1               5                   10                  15

Gly Gln Gly Ile Pro Val Ile Glu Pro Ser Gly Pro Glu Leu Val Val
            20                  25                  30

Lys Pro Gly Glu Thr Val Thr Leu Arg Cys Val Gly Asn Gly Ser Val
        35                  40                  45

Glu Trp Asp Gly Pro Ile Ser Pro His Trp Thr Leu Tyr Ser Asp Gly
50                  55                  60

Pro Ser Ser Val Leu Thr Thr Thr Asn Ala Thr Phe Gln Asn Thr Arg
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Lys Glu Val Val Phe Glu Asp Gln Asp Ala Leu Leu Pro Cys Leu
        115                 120                 125

Leu Thr Asp Pro Val Leu Glu Ala Gly Val Ser Leu Val Arg Leu Arg
130                 135                 140

Gly Arg Pro Leu Leu Arg His Thr Asn Tyr Ser Phe Ser Pro Trp His
145                 150                 155                 160

Gly Phe Thr Ile His Arg Ala Lys Phe Ile Gln Gly Gln Asp Tyr Gln
                165                 170                 175

Cys Ser Ala Leu Met Gly Ser Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
210                 215                 220

Ser Ala Ser Asn Ile Asp Val Asp Phe Asp Val Phe Leu Gln His Asn
225                 230                 235                 240

Thr Thr Lys Leu Ala Ile Pro Gln Arg Ser Asp Phe His Asp Asn Arg
                245                 250                 255

Tyr Gln Lys Val Leu Thr Leu Ser Leu Gly Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asp Leu Ser
290                 295                 300

Ser Glu Gln Asn Leu Ile Gln Glu Val Thr Val Gly Glu Gly Leu Asn
```

```
            305                 310                 315                 320
Leu Lys Val Met Val Glu Ala Tyr Pro Gly Leu Gln Gly Phe Asn Trp
                        325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
        370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Ser Ile Asn Gly Ser Gly Thr
                405                 410                 415

Leu Leu Cys Ala Ala Ser Gly Tyr Pro Gln Pro Asn Val Thr Trp Leu
                420                 425                 430

Gln Cys Ala Gly His Thr Asp Arg Cys Asp Glu Ala Gln Val Leu Gln
            435                 440                 445

Val Trp Val Asp Pro His Pro Glu Val Leu Ser Gln Glu Pro Phe Gln
    450                 455                 460

Lys Val Thr Val Gln Ser Leu Leu Thr Ala Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala Arg
                500                 505

<210> SEQ ID NO 8
<211> LENGTH: 740
<212> TYPE: PRT
<213> ORGANISM: Macaca cynomolgus
<220> FEATURE:
<221> NAME/KEY: misc_feature
<222> LOCATION: (1)..(740)
<223> OTHER INFORMATION: cynoCSF1R ECD-Fc (with leader sequence)

<400> SEQUENCE: 8

Met Gly Pro Gly Val Leu Leu Leu Leu Val Val Thr Ala Trp His
1               5                   10                  15

Gly Gln Gly Ile Pro Val Ile Glu Pro Ser Gly Pro Glu Leu Val Val
                20                  25                  30

Lys Pro Gly Glu Thr Val Thr Leu Arg Cys Val Gly Asn Gly Ser Val
            35                  40                  45

Glu Trp Asp Gly Pro Ile Ser Pro His Trp Thr Leu Tyr Ser Asp Gly
        50                  55                  60

Pro Ser Ser Val Leu Thr Thr Thr Asn Ala Thr Phe Gln Asn Thr Arg
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Lys Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Leu Arg
    130                 135                 140

Gly Arg Pro Leu Leu Arg His Thr Asn Tyr Ser Phe Ser Pro Trp His
145                 150                 155                 160
```

```
Gly Phe Thr Ile His Arg Ala Lys Phe Ile Gln Gly Gln Asp Tyr Gln
            165                 170                 175

Cys Ser Ala Leu Met Gly Ser Arg Lys Val Met Ser Ile Ser Ile Arg
        180                 185                 190

Leu Lys Val Gln Lys Val Ile Pro Gly Pro Ala Leu Thr Leu Val
        195                 200                 205

Pro Ala Glu Leu Val Arg Ile Arg Gly Glu Ala Ala Gln Ile Val Cys
210                 215                 220

Ser Ala Ser Asn Ile Asp Val Asp Phe Asp Val Phe Leu Gln His Asn
225                 230                 235                 240

Thr Thr Lys Leu Ala Ile Pro Gln Arg Ser Asp Phe His Asp Asn Arg
            245                 250                 255

Tyr Gln Lys Val Leu Thr Leu Ser Leu Gly Gln Val Asp Phe Gln His
        260                 265                 270

Ala Gly Asn Tyr Ser Cys Val Ala Ser Asn Val Gln Gly Lys His Ser
    275                 280                 285

Thr Ser Met Phe Phe Arg Val Val Glu Ser Ala Tyr Leu Asp Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
            325                 330                 335

Thr Tyr Leu Gly Pro Phe Ser Asp His Gln Pro Glu Pro Lys Leu Ala
        340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Ser Ile Asn Gly Ser Gly Thr
            405                 410                 415

Leu Leu Cys Ala Ala Ser Gly Tyr Pro Gln Pro Asn Val Thr Trp Leu
        420                 425                 430

Gln Cys Ala Gly His Thr Asp Arg Cys Asp Glu Ala Gln Val Leu Gln
        435                 440                 445

Val Trp Val Asp Pro His Pro Glu Val Leu Ser Gln Glu Pro Phe Gln
    450                 455                 460

Lys Val Thr Val Gln Ser Leu Leu Thr Ala Glu Thr Leu Glu His Asn
465                 470                 475                 480

Gln Thr Tyr Glu Cys Arg Ala His Asn Ser Val Gly Ser Gly Ser Trp
            485                 490                 495

Ala Phe Ile Pro Ile Ser Ala Gly Ala Arg Gly Ser Glu Pro Lys Ser
        500                 505                 510

Ser Asp Lys Thr His Thr Cys Pro Pro Cys Pro Ala Pro Glu Leu Leu
        515                 520                 525

Gly Gly Pro Ser Val Phe Leu Phe Pro Pro Lys Pro Lys Asp Thr Leu
    530                 535                 540

Met Ile Ser Arg Thr Pro Glu Val Thr Cys Val Val Val Asp Val Ser
545                 550                 555                 560

His Glu Asp Pro Glu Val Lys Phe Asn Trp Tyr Val Asp Gly Val Glu
            565                 570                 575

Val His Asn Ala Lys Thr Lys Pro Arg Glu Glu Gln Tyr Asn Ser Thr
        580                 585                 590
```

```
Tyr Arg Val Val Ser Val Leu Thr Val Leu His Gln Asp Trp Leu Asn
            595                 600                 605
Gly Lys Glu Tyr Lys Cys Lys Val Ser Asn Lys Ala Leu Pro Ala Pro
        610                 615                 620
Ile Glu Lys Thr Ile Ser Lys Ala Lys Gly Gln Pro Arg Glu Pro Gln
625                 630                 635                 640
Val Tyr Thr Leu Pro Pro Ser Arg Asp Glu Leu Thr Lys Asn Gln Val
                645                 650                 655
Ser Leu Thr Cys Leu Val Lys Gly Phe Tyr Pro Ser Asp Ile Ala Val
            660                 665                 670
Glu Trp Glu Ser Asn Gly Gln Pro Glu Asn Asn Tyr Lys Thr Thr Pro
        675                 680                 685
Pro Val Leu Asp Ser Asp Gly Ser Phe Phe Leu Tyr Ser Lys Leu Thr
    690                 695                 700
Val Asp Lys Ser Arg Trp Gln Gln Gly Asn Val Phe Ser Cys Ser Val
705                 710                 715                 720
Met His Glu Ala Leu His Asn His Tyr Thr Gln Lys Ser Leu Ser Leu
                725                 730                 735
Ser Pro Gly Lys
            740

<210> SEQ ID NO 9
<211> LENGTH: 122
<212> TYPE: PRT
<213> ORGANISM: Mus musculus
<220> FEATURE:
<221> NAME/KEY: misc_feature
<222> LOCATION: (1)..(122)
<223> OTHER INFORMATION: Fab 0301 heavy chain variable region

<400> SEQUENCE: 9

Glu Val Gln Leu Gln Gln Ser Gly Pro Glu Leu Val Arg Pro Gly Ala
1               5                   10                  15
Ser Val Lys Met Ser Cys Lys Ala Ser Gly Tyr Thr Phe Thr Asp Asn
            20                  25                  30
Tyr Met Ile Trp Val Lys Gln Ser His Gly Lys Ser Leu Glu Trp Ile
        35                  40                  45
Gly Asp Ile Asn Pro Tyr Asn Gly Gly Thr Thr Phe Asn Gln Lys Phe
    50                  55                  60
Lys Gly Lys Ala Thr Leu Thr Val Glu Lys Ser Ser Ser Thr Ala Tyr
65                  70                  75                  80
Met Gln Leu Asn Ser Leu Thr Ser Glu Asp Ser Ala Val Tyr Tyr Cys
                85                  90                  95
Ala Arg Glu Ser Pro Tyr Phe Ser Asn Leu Tyr Val Met Asp Tyr Trp
            100                 105                 110
Gly Gln Gly Thr Ser Val Thr Val Ser Ser
        115                 120

<210> SEQ ID NO 10
<211> LENGTH: 111
<212> TYPE: PRT
<213> ORGANISM: Mus musculus
<220> FEATURE:
<221> NAME/KEY: misc_feature
<222> LOCATION: (1)..(111)
<223> OTHER INFORMATION: Fab 0301 light chain variable region

<400> SEQUENCE: 10

Asn Ile Val Leu Thr Gln Ser Pro Ala Ser Leu Ala Val Ser Leu Gly
```

```
                1               5                  10                 15
Gln Arg Ala Thr Ile Ser Cys Lys Ala Ser Gln Ser Val Asp Tyr Asp
                                20                 25                 30

Gly Asp Asn Tyr Met Asn Trp Tyr Gln Gln Lys Pro Gly Gln Pro Pro
            35                  40                 45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                      80

Pro Val Glu Glu Glu Asp Ala Ala Thr Tyr Tyr Cys His Leu Ser Asn
                    85                  90                  95

Glu Asp Leu Ser Thr Phe Gly Gly Gly Thr Lys Leu Glu Ile Lys
                100                 105                 110
```

<210> SEQ ID NO 11
<211> LENGTH: 121
<212> TYPE: PRT
<213> ORGANISM: Mus musculus
<220> FEATURE:
<221> NAME/KEY: misc_feature
<222> LOCATION: (1)..(121)
<223> OTHER INFORMATION: Fab 0302 heavy chain variable region

<400> SEQUENCE: 11

```
Glu Ile Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Asp Phe
                20                  25                  30

Asn Ile His Trp Val Lys Gln Lys Pro Gly Gln Gly Leu Glu Trp Ile
            35                  40                  45

Gly Tyr Ile Asn Pro Tyr Thr Asp Val Thr Val Tyr Asn Glu Lys Phe
    50                  55                  60

Lys Gly Lys Ala Thr Leu Thr Ser Asp Arg Ser Ser Thr Ala Tyr
65                  70                  75                  80

Met Asp Leu Ser Ser Leu Thr Ser Glu Asp Ser Ala Val Tyr Tyr Cys
                85                  90                  95

Ala Ser Tyr Phe Asp Gly Thr Phe Asp Tyr Ala Leu Asp Tyr Trp Gly
                100                 105                 110

Gln Gly Thr Ser Ile Thr Val Ser Ser
            115                 120
```

<210> SEQ ID NO 12
<211> LENGTH: 111
<212> TYPE: PRT
<213> ORGANISM: Mus musculus
<220> FEATURE:
<221> NAME/KEY: misc_feature
<222> LOCATION: (1)..(111)
<223> OTHER INFORMATION: Fab 0302 light chain variable region

<400> SEQUENCE: 12

```
Asp Val Val Val Thr Gln Thr Pro Ala Ser Leu Ala Val Ser Leu Gly
1               5                   10                  15

Gln Arg Ala Thr Ile Ser Cys Arg Ala Ser Glu Ser Val Asp Asn Tyr
                20                  25                  30

Gly Leu Ser Phe Met Asn Trp Phe Gln Gln Lys Pro Gly Gln Pro Pro
            35                  40                  45

Lys Leu Leu Ile Tyr Thr Ala Ser Asn Leu Glu Ser Gly Ile Pro Ala
    50                  55                  60
```

Arg Phe Ser Gly Gly Gly Ser Arg Thr Asp Phe Thr Leu Thr Ile Asp
65                  70                  75                  80

Pro Val Glu Ala Asp Asp Ala Ala Thr Tyr Phe Cys Gln Gln Ser Lys
                85                  90                  95

Glu Leu Pro Trp Thr Phe Gly Gly Gly Thr Arg Leu Glu Ile Lys
            100                 105                 110

<210> SEQ ID NO 13
<211> LENGTH: 122
<212> TYPE: PRT
<213> ORGANISM: Mus musculus
<220> FEATURE:
<221> NAME/KEY: misc_feature
<222> LOCATION: (1)..(122)
<223> OTHER INFORMATION: Fab 0311 heavy chain variable region

<400> SEQUENCE: 13

Glu Ile Gln Leu Gln Gln Ser Gly Pro Asp Leu Met Lys Pro Gly Ala
1               5                   10                  15

Ser Val Lys Met Ser Cys Lys Ala Ser Gly Tyr Ile Phe Thr Asp Tyr
                20                  25                  30

Asn Met His Trp Val Lys Gln Asn Gly Lys Ser Leu Glu Trp Met
            35                  40                  45

Gly Glu Ile Asn Pro Asn Asn Gly Val Val Tyr Asn Gln Lys Phe
50                  55                  60

Lys Gly Thr Thr Thr Leu Thr Val Asp Lys Ser Ser Thr Ala Tyr
65                  70                  75                  80

Met Asp Leu His Ser Leu Thr Ser Glu Asp Ser Ala Val Tyr Tyr Cys
                85                  90                  95

Thr Arg Ala Leu Tyr His Ser Asn Phe Gly Trp Tyr Phe Asp Ser Trp
            100                 105                 110

Gly Lys Gly Thr Thr Leu Thr Val Ser Ser
            115                 120

<210> SEQ ID NO 14
<211> LENGTH: 111
<212> TYPE: PRT
<213> ORGANISM: Mus musculus
<220> FEATURE:
<221> NAME/KEY: misc_feature
<222> LOCATION: (1)..(111)
<223> OTHER INFORMATION: Fab 0311 light chain variable region

<400> SEQUENCE: 14

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser His Met Asn Trp Tyr Gln Gln Lys Pro Gly Gln Pro Pro
            35                  40                  45

Lys Leu Leu Ile Tyr Thr Ala Ser Asn Leu Glu Ser Gly Ile Pro Ala
50                  55                  60

Arg Phe Ser Gly Ser Gly Ser Gly Ala Asp Phe Thr Leu Thr Ile His
65                  70                  75                  80

Pro Val Glu Glu Glu Asp Ala Ala Thr Tyr Tyr Cys Gln Gln Gly Asn
                85                  90                  95

Glu Asp Pro Trp Thr Phe Gly Gly Gly Thr Arg Leu Glu Ile Lys
            100                 105                 110

<210> SEQ ID NO 15

```
<211> LENGTH: 10
<212> TYPE: PRT
<213> ORGANISM: Mus musculus
<220> FEATURE:
<221> NAME/KEY: misc_feature
<222> LOCATION: (1)..(10)
<223> OTHER INFORMATION: 0301 heavy chain CDR1

<400> SEQUENCE: 15

Gly Tyr Thr Phe Thr Asp Asn Tyr Met Ile
1               5                   10

<210> SEQ ID NO 16
<211> LENGTH: 17
<212> TYPE: PRT
<213> ORGANISM: Mus musculus
<220> FEATURE:
<221> NAME/KEY: misc_feature
<222> LOCATION: (1)..(17)
<223> OTHER INFORMATION: 0301 heavy chain CDR2

<400> SEQUENCE: 16

Asp Ile Asn Pro Tyr Asn Gly Gly Thr Thr Phe Asn Gln Lys Phe Lys
1               5                   10                  15

Gly

<210> SEQ ID NO 17
<211> LENGTH: 13
<212> TYPE: PRT
<213> ORGANISM: Mus musculus
<220> FEATURE:
<221> NAME/KEY: misc_feature
<222> LOCATION: (1)..(13)
<223> OTHER INFORMATION: 0301 heavy chain CDR3

<400> SEQUENCE: 17

Glu Ser Pro Tyr Phe Ser Asn Leu Tyr Val Met Asp Tyr
1               5                   10

<210> SEQ ID NO 18
<211> LENGTH: 15
<212> TYPE: PRT
<213> ORGANISM: Mus musculus
<220> FEATURE:
<221> NAME/KEY: misc_feature
<222> LOCATION: (1)..(15)
<223> OTHER INFORMATION: 0301 light chain CDR1

<400> SEQUENCE: 18

Lys Ala Ser Gln Ser Val Asp Tyr Asp Gly Asp Asn Tyr Met Asn
1               5                   10                  15

<210> SEQ ID NO 19
<211> LENGTH: 7
<212> TYPE: PRT
<213> ORGANISM: Mus musculus
<220> FEATURE:
<221> NAME/KEY: misc_feature
<222> LOCATION: (1)..(7)
<223> OTHER INFORMATION: 0301 light chain CDR2

<400> SEQUENCE: 19

Ala Ala Ser Asn Leu Glu Ser
1               5

<210> SEQ ID NO 20
<211> LENGTH: 9
<212> TYPE: PRT
<213> ORGANISM: Mus musculus
```

```
<220> FEATURE:
<221> NAME/KEY: misc_feature
<222> LOCATION: (1)..(9)
<223> OTHER INFORMATION: 0301 light chain CDR3

<400> SEQUENCE: 20

His Leu Ser Asn Glu Asp Leu Ser Thr
1               5

<210> SEQ ID NO 21
<211> LENGTH: 10
<212> TYPE: PRT
<213> ORGANISM: Mus musculus
<220> FEATURE:
<221> NAME/KEY: misc_feature
<222> LOCATION: (1)..(10)
<223> OTHER INFORMATION: 0302 heavy chain CDR1

<400> SEQUENCE: 21

Gly Tyr Thr Phe Ser Asp Phe Asn Ile His
1               5                   10

<210> SEQ ID NO 22
<211> LENGTH: 17
<212> TYPE: PRT
<213> ORGANISM: Mus musculus
<220> FEATURE:
<221> NAME/KEY: misc_feature
<222> LOCATION: (1)..(17)
<223> OTHER INFORMATION: 0302 heavy chain CDR2

<400> SEQUENCE: 22

Tyr Ile Asn Pro Tyr Thr Asp Val Thr Val Tyr Asn Glu Lys Phe Lys
1               5                   10                  15

Gly

<210> SEQ ID NO 23
<211> LENGTH: 12
<212> TYPE: PRT
<213> ORGANISM: Mus musculus
<220> FEATURE:
<221> NAME/KEY: misc_feature
<222> LOCATION: (1)..(12)
<223> OTHER INFORMATION: 0302 heavy chain CDR3

<400> SEQUENCE: 23

Tyr Phe Asp Gly Thr Phe Asp Tyr Ala Leu Asp Tyr
1               5                   10

<210> SEQ ID NO 24
<211> LENGTH: 15
<212> TYPE: PRT
<213> ORGANISM: Mus musculus
<220> FEATURE:
<221> NAME/KEY: misc_feature
<222> LOCATION: (1)..(15)
<223> OTHER INFORMATION: 0302 light chain CDR1

<400> SEQUENCE: 24

Arg Ala Ser Glu Ser Val Asp Asn Tyr Gly Leu Ser Phe Met Asn
1               5                   10                  15

<210> SEQ ID NO 25
<211> LENGTH: 7
<212> TYPE: PRT
<213> ORGANISM: Mus musculus
<220> FEATURE:
<221> NAME/KEY: misc_feature
<222> LOCATION: (1)..(7)
```

-continued

```
<223> OTHER INFORMATION: 0302 light chain CDR2

<400> SEQUENCE: 25

Thr Ala Ser Asn Leu Glu Ser
1               5

<210> SEQ ID NO 26
<211> LENGTH: 9
<212> TYPE: PRT
<213> ORGANISM: Mus musculus
<220> FEATURE:
<221> NAME/KEY: misc_feature
<222> LOCATION: (1)..(9)
<223> OTHER INFORMATION: 0302 light chain CDR3

<400> SEQUENCE: 26

Gln Gln Ser Lys Glu Leu Pro Trp Thr
1               5

<210> SEQ ID NO 27
<211> LENGTH: 10
<212> TYPE: PRT
<213> ORGANISM: Mus musculus
<220> FEATURE:
<221> NAME/KEY: misc_feature
<222> LOCATION: (1)..(10)
<223> OTHER INFORMATION: 0311 heavy chain CDR1

<400> SEQUENCE: 27

Gly Tyr Ile Phe Thr Asp Tyr Asn Met His
1               5                   10

<210> SEQ ID NO 28
<211> LENGTH: 17
<212> TYPE: PRT
<213> ORGANISM: Mus musculus
<220> FEATURE:
<221> NAME/KEY: misc_feature
<222> LOCATION: (1)..(17)
<223> OTHER INFORMATION: 0311 heavy chain CDR2

<400> SEQUENCE: 28

Glu Ile Asn Pro Asn Asn Gly Val Val Val Tyr Asn Gln Lys Phe Lys
1               5                   10                  15
Gly

<210> SEQ ID NO 29
<211> LENGTH: 13
<212> TYPE: PRT
<213> ORGANISM: Mus musculus
<220> FEATURE:
<221> NAME/KEY: misc_feature
<222> LOCATION: (1)..(13)
<223> OTHER INFORMATION: 0311 heavy chain CDR3

<400> SEQUENCE: 29

Ala Leu Tyr His Ser Asn Phe Gly Trp Tyr Phe Asp Ser
1               5                   10

<210> SEQ ID NO 30
<211> LENGTH: 15
<212> TYPE: PRT
<213> ORGANISM: Mus musculus
<220> FEATURE:
<221> NAME/KEY: misc_feature
<222> LOCATION: (1)..(15)
<223> OTHER INFORMATION: 0311 light chain CDR1

<400> SEQUENCE: 30
```

-continued

Lys Ala Ser Gln Ser Val Asp Tyr Asp Gly Asp Ser His Met Asn
1               5                   10                  15

<210> SEQ ID NO 31
<211> LENGTH: 7
<212> TYPE: PRT
<213> ORGANISM: Mus musculus
<220> FEATURE:
<221> NAME/KEY: misc_feature
<222> LOCATION: (1)..(7)
<223> OTHER INFORMATION: 0311 light chain CDR2

<400> SEQUENCE: 31

Thr Ala Ser Asn Leu Glu Ser
1               5

<210> SEQ ID NO 32
<211> LENGTH: 9
<212> TYPE: PRT
<213> ORGANISM: Mus musculus
<220> FEATURE:
<221> NAME/KEY: misc_feature
<222> LOCATION: (1)..(9)
<223> OTHER INFORMATION: 0311 light chain CDR3

<400> SEQUENCE: 32

Gln Gln Gly Asn Glu Asp Pro Trp Thr
1               5

<210> SEQ ID NO 33
<211> LENGTH: 449
<212> TYPE: PRT
<213> ORGANISM: Artificial Sequence
<220> FEATURE:
<223> OTHER INFORMATION: Synthetic: cAb 0301 heavy chain

<400> SEQUENCE: 33

Glu Val Gln Leu Gln Gln Ser Gly Pro Glu Leu Val Arg Pro Gly Ala
1               5                   10                  15

Ser Val Lys Met Ser Cys Lys Ala Ser Gly Tyr Thr Phe Thr Asp Asn
            20                  25                  30

Tyr Met Ile Trp Val Lys Gln Ser His Gly Lys Ser Leu Glu Trp Ile
        35                  40                  45

Gly Asp Ile Asn Pro Tyr Asn Gly Gly Thr Thr Phe Asn Gln Lys Phe
    50                  55                  60

Lys Gly Lys Ala Thr Leu Thr Val Glu Lys Ser Ser Thr Ala Tyr
65                  70                  75                  80

Met Gln Leu Asn Ser Leu Thr Ser Glu Asp Ser Ala Val Tyr Tyr Cys
            85                  90                  95

Ala Arg Glu Ser Pro Tyr Phe Ser Asn Leu Tyr Val Met Asp Tyr Trp
        100                 105                 110

Gly Gln Gly Thr Ser Val Thr Val Ser Ser Ala Ser Thr Lys Gly Pro
    115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
    435                 440                 445

Lys

<210> SEQ ID NO 34
<211> LENGTH: 218
<212> TYPE: PRT
<213> ORGANISM: Artificial Sequence
<220> FEATURE:
<223> OTHER INFORMATION: Synthetic: cAb 0301 light chain

<400> SEQUENCE: 34

Asn Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Asn Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys His Leu Ser Asn
                85                  90                  95

Glu Asp Leu Ser Thr Phe Gly Gly Gly Thr Lys Leu Glu Ile Lys Arg
                100                 105                 110

```
Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 35
<211> LENGTH: 448
<212> TYPE: PRT
<213> ORGANISM: Artificial Sequence
<220> FEATURE:
<223> OTHER INFORMATION: Synthetic: cAb 0302 heavy chain

<400> SEQUENCE: 35

Glu Ile Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Asp Phe
                20                  25                  30

Asn Ile His Trp Val Lys Gln Lys Pro Gly Gln Gly Leu Glu Trp Ile
            35                  40                  45

Gly Tyr Ile Asn Pro Tyr Thr Asp Val Thr Val Tyr Asn Glu Lys Phe
50                  55                  60

Lys Gly Lys Ala Thr Leu Thr Ser Asp Arg Ser Ser Thr Ala Tyr
65                  70                  75                  80

Met Asp Leu Ser Ser Leu Thr Ser Glu Asp Ser Ala Val Tyr Tyr Cys
                85                  90                  95

Ala Ser Tyr Phe Asp Gly Thr Phe Asp Tyr Ala Leu Asp Tyr Trp Gly
            100                 105                 110

Gln Gly Thr Ser Ile Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255
```

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 36
<211> LENGTH: 218
<212> TYPE: PRT
<213> ORGANISM: Artificial Sequence
<220> FEATURE:
<223> OTHER INFORMATION: Synthetic: cAb 0302 light chain

<400> SEQUENCE: 36

Asp Val Val Thr Gln Thr Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Leu Ser Phe Met Asn Trp Phe Gln Gln Lys Pro Gly Gln Pro Pro
        35                  40                  45

Lys Leu Leu Ile Tyr Thr Ala Ser Asn Leu Glu Ser Gly Ile Pro Ala
    50                  55                  60

Arg Phe Ser Gly Gly Gly Ser Arg Thr Asp Phe Thr Leu Thr Ile Asp
65                  70                  75                  80

Pro Val Glu Ala Asp Asp Ala Ala Thr Tyr Phe Cys Gln Gln Ser Lys
                85                  90                  95

Glu Leu Pro Trp Thr Phe Gly Gly Gly Thr Arg Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys

His Lys Val Tyr Ala Cys Glu Val Thr His Gln Gly Leu Ser Ser Pro
            180                 185                 190

Val Thr Lys Ser Phe Asn Arg Gly Glu Cys
    195                 200             205
        210                 215

<210> SEQ ID NO 37
<211> LENGTH: 449
<212> TYPE: PRT
<213> ORGANISM: Artificial Sequence
<220> FEATURE:
<223> OTHER INFORMATION: Synthetic: cAb 0311 heavy chain

<400> SEQUENCE: 37

Glu Ile Gln Leu Gln Gln Ser Gly Pro Asp Leu Met Lys Pro Gly Ala
1               5                   10                  15

Ser Val Lys Met Ser Cys Lys Ala Ser Gly Tyr Ile Phe Thr Asp Tyr
            20                  25                  30

Asn Met His Trp Val Lys Gln Asn Gln Gly Lys Ser Leu Glu Trp Met
        35                  40                  45

Gly Glu Ile Asn Pro Asn Asn Gly Val Val Tyr Asn Gln Lys Phe
    50                  55                  60

Lys Gly Thr Thr Thr Leu Thr Val Asp Lys Ser Ser Thr Ala Tyr
65                  70                  75                  80

Met Asp Leu His Ser Leu Thr Ser Glu Asp Ser Ala Val Tyr Tyr Cys
            85                  90                  95

Thr Arg Ala Leu Tyr His Ser Asn Phe Gly Trp Tyr Phe Asp Ser Trp
            100                 105                 110

Gly Lys Gly Thr Thr Leu Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
        210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

```
Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Lys

<210> SEQ ID NO 38
<211> LENGTH: 218
<212> TYPE: PRT
<213> ORGANISM: Artificial Sequence
<220> FEATURE:
<223> OTHER INFORMATION: Synthetic: cAb 0311 light chain

<400> SEQUENCE: 38

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser His Met Asn Trp Tyr Gln Gln Lys Pro Gly Gln Pro Pro
            35                  40                  45

Lys Leu Leu Ile Tyr Thr Ala Ser Asn Leu Glu Ser Gly Ile Pro Ala
        50                  55                  60

Arg Phe Ser Gly Ser Gly Ser Gly Ala Asp Phe Thr Leu Thr Ile His
65                  70                  75                  80

Pro Val Glu Glu Glu Asp Ala Ala Thr Tyr Tyr Cys Gln Gln Gly Asn
                85                  90                  95

Glu Asp Pro Trp Thr Phe Gly Gly Gly Thr Arg Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 39
<211> LENGTH: 122
<212> TYPE: PRT
```

```
<213> ORGANISM: Artificial Sequence
<220> FEATURE:
<223> OTHER INFORMATION: Synthetic: h0301-H0 heavy chain variable region

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Thr Thr Phe Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Leu Val Thr Val Ser Ser
        115                 120

<210> SEQ ID NO 40
<211> LENGTH: 122
<212> TYPE: PRT
<213> ORGANISM: Artificial Sequence
<220> FEATURE:
<223> OTHER INFORMATION: Synthetic: h0301-H1 heavy chain variable region

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Thr Thr Phe Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Leu Val Thr Val Ser Ser
        115                 120

<210> SEQ ID NO 41
<211> LENGTH: 122
<212> TYPE: PRT
<213> ORGANISM: Artificial Sequence
<220> FEATURE:
<223> OTHER INFORMATION: Synthetic: h0301-H2 heavy chain variable region

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
            20                  25                  30
```

```
Tyr Met Ile Trp Val Arg Gln Ala Pro Gly Gln Gly Leu Glu Trp Ile
         35                  40                  45

Gly Asp Ile Asn Pro Tyr Asn Gly Gly Thr Thr Phe Asn Gln Lys Phe
 50                  55                  60

Lys Gly Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ser Pro Tyr Phe Ser Asn Leu Tyr Val Met Asp Tyr Trp
                100                 105                 110

Gly Gln Gly Thr Leu Val Thr Val Ser Ser
                115                 120
```

<210> SEQ ID NO 42
<211> LENGTH: 121
<212> TYPE: PRT
<213> ORGANISM: Artificial Sequence
<220> FEATURE:
<223> OTHER INFORMATION: Synthetic: H0302-H1 heavy chain variable region

<400> SEQUENCE: 42

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Ser Asp Phe
                 20                  25                  30

Asn Ile His Trp Val Arg Gln Ala Pro Gly Gln Gly Leu Glu Trp Met
             35                  40                  45

Gly Tyr Ile Asn Pro Tyr Thr Asp Val Thr Val Tyr Asn Glu Lys Phe
 50                  55                  60

Lys Gly Arg Val Thr Ile Thr Ser Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Tyr Phe Asp Gly Thr Phe Asp Tyr Ala Leu Asp Tyr Trp Gly
                100                 105                 110

Gln Gly Thr Leu Val Thr Val Ser Ser
            115                 120
```

<210> SEQ ID NO 43
<211> LENGTH: 121
<212> TYPE: PRT
<213> ORGANISM: Artificial Sequence
<220> FEATURE:
<223> OTHER INFORMATION: Synthetic: H0302-H2 heavy chain variable region

<400> SEQUENCE: 43

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Ser Asp Phe
                 20                  25                  30

Asn Ile His Trp Val Arg Gln Ala Pro Gly Gln Gly Leu Glu Trp Ile
             35                  40                  45

Gly Tyr Ile Asn Pro Tyr Thr Asp Val Thr Val Tyr Asn Glu Lys Phe
 50                  55                  60

Lys Gly Arg Ala Thr Leu Thr Ser Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

Ala Ser Tyr Phe Asp Gly Thr Phe Asp Tyr Ala Leu Asp Tyr Trp Gly
            100                 105                 110

Gln Gly Thr Leu Val Thr Val Ser Ser
        115                 120

<210> SEQ ID NO 44
<211> LENGTH: 122
<212> TYPE: PRT
<213> ORGANISM: Artificial Sequence
<220> FEATURE:
<223> OTHER INFORMATION: Synthetic: H0311-H1 heavy chain variable region

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Asn Gly Val Val Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ala Leu Tyr His Ser Asn Phe Gly Trp Tyr Phe Asp Ser Trp
            100                 105                 110

Gly Gln Gly Thr Leu Val Thr Val Ser Ser
        115                 120

<210> SEQ ID NO 45
<211> LENGTH: 122
<212> TYPE: PRT
<213> ORGANISM: Artificial Sequence
<220> FEATURE:
<223> OTHER INFORMATION: Synthetic: H0311-H2 heavy chain variable region

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Asn Gly Val Val Tyr Asn Gln Lys Phe
    50                  55                  60

Lys Gly Thr Thr Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ala Leu Tyr His Ser Asn Phe Gly Trp Tyr Phe Asp Ser Trp
            100                 105                 110

Gly Gln Gly Thr Leu Val Thr Val Ser Ser
        115                 120

<210> SEQ ID NO 46
<211> LENGTH: 111
<212> TYPE: PRT
<213> ORGANISM: Artificial Sequence
<220> FEATURE:

<223> OTHER INFORMATION: Synthetic: h0301-L0 light chain variable region

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys
            100                 105                 110

<210> SEQ ID NO 47
<211> LENGTH: 111
<212> TYPE: PRT
<213> ORGANISM: Artificial Sequence
<220> FEATURE:
<223> OTHER INFORMATION: Synthetic: h0301-L1 light chain variable region

<400> SEQUENCE: 47

Asn Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys
            100                 105                 110

<210> SEQ ID NO 48
<211> LENGTH: 111
<212> TYPE: PRT
<213> ORGANISM: Artificial Sequence
<220> FEATURE:
<223> OTHER INFORMATION: Synthetic: H0302-L0 light chain variable region

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Met Asn Trp Tyr Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

```
Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys
            100                 105                 110

<210> SEQ ID NO 49
<211> LENGTH: 111
<212> TYPE: PRT
<213> ORGANISM: Artificial Sequence
<220> FEATURE:
<223> OTHER INFORMATION: Synthetic: H0302-L1 light chain variable region

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Met Asn Trp Tyr Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys
            100                 105                 110

<210> SEQ ID NO 50
<211> LENGTH: 111
<212> TYPE: PRT
<213> ORGANISM: Artificial Sequence
<220> FEATURE:
<223> OTHER INFORMATION: Synthetic: H0302-L2 light chain variable region

<400> SEQUENCE: 50

Glu Ile Val Val Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Met Asn Trp Phe Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys
            100                 105                 110

<210> SEQ ID NO 51
<211> LENGTH: 111
<212> TYPE: PRT
<213> ORGANISM: Artificial Sequence
<220> FEATURE:
<223> OTHER INFORMATION: Synthetic: H0311-L0 light chain variable region

<400> SEQUENCE: 51

Glu Ile Val Leu Thr Gln Ser Pro Ala Thr Leu Ser Leu Ser Pro Gly
```

```
                 1               5                  10                  15
Glu Arg Ala Thr Leu Ser Cys Lys Ala Ser Gln Ser Val Asp Tyr Asp
                20                  25                  30

Gly Asp Ser His Met Asn Trp Tyr Gln Gln Lys Pro Gly Gln Ala Pro
                35                  40                  45

Arg Leu Leu Ile Tyr Thr Ala Ser Asn Leu Glu Ser Gly Ile Pro Ala
                50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Gly Asn
                85                  90                  95

Glu Asp Pro Trp Thr Phe Gly Gln Gly Thr Lys Val Glu Ile Lys
                100                 105                 110

<210> SEQ ID NO 52
<211> LENGTH: 111
<212> TYPE: PRT
<213> ORGANISM: Artificial Sequence
<220> FEATURE:
<223> OTHER INFORMATION: Synthetic: H0311-L1 light chain variable region

<400> SEQUENCE: 52

Asp Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
                20                  25                  30

Gly Asp Ser His Met Asn Trp Tyr Gln Gln Lys Pro Gly Gln Ala Pro
                35                  40                  45

Arg Leu Leu Ile Tyr Thr Ala Ser Asn Leu Glu Ser Gly Ile Pro Ala
                50                  55                  60

Arg Phe Ser Gly Ser Gly Ser Gly Ala Asp Phe Thr Leu Thr Ile Ser
65                  70                  75                  80

Ser Leu Glu Pro Glu Asp Phe Ala Val Tyr Tyr Cys Gln Gln Gly Asn
                85                  90                  95

Glu Asp Pro Trp Thr Phe Gly Gln Gly Thr Lys Val Glu Ile Lys
                100                 105                 110

<210> SEQ ID NO 53
<211> LENGTH: 449
<212> TYPE: PRT
<213> ORGANISM: Artificial Sequence
<220> FEATURE:
<223> OTHER INFORMATION: Synthetic: h0301-H0 heavy chain

<400> SEQUENCE: 53

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
                20                  25                  30

Tyr Met Ile Trp Val Arg Gln Ala Pro Gly Gln Gly Leu Glu Trp Met
                35                  40                  45

Gly Asp Ile Asn Pro Tyr Asn Gly Gly Thr Thr Phe Asn Gln Lys Phe
                50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
```

```
                100              105              110
Gly Gln Gly Thr Leu Val Thr Val Ser Ser Ala Ser Thr Lys Gly Pro
            115              120              125

Ser Val Phe Pro Leu Ala Pro Cys Ser Arg Ser Thr Ser Glu Ser Thr
130              135              140

Ala Ala Leu Gly Cys Leu Val Lys Asp Tyr Phe Pro Glu Pro Val Thr
145              150              155              160

Val Ser Trp Asn Ser Gly Ala Leu Thr Ser Gly Val His Thr Phe Pro
            165              170              175

Ala Val Leu Gln Ser Ser Gly Leu Tyr Ser Leu Ser Ser Val Val Thr
            180              185              190

Val Pro Ser Ser Ser Leu Gly Thr Lys Thr Tyr Thr Cys Asn Val Asp
            195              200              205

His Lys Pro Ser Asn Thr Lys Val Asp Lys Arg Val Glu Ser Lys Tyr
            210              215              220

Gly Pro Pro Cys Pro Pro Cys Pro Ala Pro Glu Phe Leu Gly Gly Pro
225              230              235              240

Ser Val Phe Leu Phe Pro Pro Lys Pro Lys Asp Thr Leu Met Ile Ser
            245              250              255

Arg Thr Pro Glu Val Thr Cys Val Val Val Asp Val Ser Gln Glu Asp
            260              265              270

Pro Glu Val Gln Phe Asn Trp Tyr Val Asp Gly Val Glu Val His Asn
            275              280              285

Ala Lys Thr Lys Pro Arg Glu Glu Gln Phe Asn Ser Thr Tyr Arg Val
            290              295              300

Val Ser Val Leu Thr Val Leu His Gln Asp Trp Leu Asn Gly Lys Glu
305              310              315              320

Tyr Lys Cys Lys Val Ser Asn Lys Gly Leu Pro Ser Ser Ile Glu Lys
            325              330              335

Thr Ile Ser Lys Ala Lys Gly Gln Pro Arg Glu Pro Gln Val Tyr Thr
            340              345              350

Leu Pro Pro Ser Gln Glu Glu Met Thr Lys Asn Gln Val Ser Leu Thr
            355              360              365

Cys Leu Val Lys Gly Phe Tyr Pro Ser Asp Ile Ala Val Glu Trp Glu
370              375              380

Ser Asn Gly Gln Pro Glu Asn Asn Tyr Lys Thr Thr Pro Pro Val Leu
385              390              395              400

Asp Ser Asp Gly Ser Phe Phe Leu Tyr Ser Arg Leu Thr Val Asp Lys
            405              410              415

Ser Arg Trp Gln Glu Gly Asn Val Phe Ser Cys Ser Val Met His Glu
            420              425              430

Ala Leu His Asn His Tyr Thr Gln Lys Ser Leu Ser Leu Ser Leu Gly
            435              440              445

Lys

<210> SEQ ID NO 54
<211> LENGTH: 449
<212> TYPE: PRT
<213> ORGANISM: Artificial Sequence
<220> FEATURE:
<223> OTHER INFORMATION: Synthetic: h0301-H1 heavy chain

<400> SEQUENCE: 54

Gln Val Gln Leu Val Gln Ser Gly Ala Glu Val Lys Lys Pro Gly Ser
1               5               10              15
```

-continued

```
Ser Val Lys Val Ser Cys Lys Ala Ser Gly Tyr Thr Phe Thr Asp Asn
         20                  25                  30

Tyr Met Ile Trp Val Arg Gln Ala Pro Gly Gln Gly Leu Glu Trp Met
     35                  40                  45

Gly Asp Ile Asn Pro Tyr Asn Gly Gly Thr Thr Phe Asn Gln Lys Phe
 50                  55                  60

Lys Gly Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ser Pro Tyr Phe Ser Asn Leu Tyr Val Met Asp Tyr Trp
             100                 105                 110

Gly Gln Gly Thr Leu Val Thr Val Ser Ser Ala Ser Thr Lys Gly Pro
         115                 120                 125

Ser Val Phe Pro Leu Ala Pro Cys Ser Arg Ser Thr Ser Glu Ser Thr
         130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                 165                 170                 175

Ala Val Leu Gln Ser Ser Gly Leu Tyr Ser Leu Ser Ser Val Val Thr
             180                 185                 190

Val Pro Ser Ser Ser Leu Gly Thr Lys Thr Tyr Thr Cys Asn Val Asp
         195                 200                 205

His Lys Pro Ser Asn Thr Lys Val Asp Lys Arg Val Glu Ser Lys Tyr
         210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser Gln Glu Asp
             260                 265                 270

Pro Glu Val Gln Phe Asn Trp Tyr Val Asp Gly Val Glu Val His Asn
         275                 280                 285

Ala Lys Thr Lys Pro Arg Glu Glu Gln Phe Asn Ser Thr Tyr Arg Val
         290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Gln Glu Glu Met Thr Lys Asn Gln Val Ser Leu Thr
         355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                 405                 410                 415

Ser Arg Trp Gln Glu Gly Asn Val Phe Ser Cys Ser Val Met His Glu
             420                 425                 430

Ala Leu His Asn His Tyr Thr Gln Lys Ser Leu Ser Leu Ser Leu Gly
         435                 440                 445
```

Lys

<210> SEQ ID NO 55
<211> LENGTH: 449
<212> TYPE: PRT
<213> ORGANISM: Artificial Sequence
<220> FEATURE:
<223> OTHER INFORMATION: Synthetic: h0301-H2 heavy chain

<400> SEQUENCE: 55

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
            20                  25                  30

Tyr Met Ile Trp Val Arg Gln Ala Pro Gly Gln Gly Leu Glu Trp Ile
        35                  40                  45

Gly Asp Ile Asn Pro Tyr Asn Gly Gly Thr Thr Phe Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
```

```
                  355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Lys

<210> SEQ ID NO 56
<211> LENGTH: 448
<212> TYPE: PRT
<213> ORGANISM: Artificial Sequence
<220> FEATURE:
<223> OTHER INFORMATION: Synthetic: H0302-H1 heavy chain

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Phe
                20                  25                  30

Asn Ile His Trp Val Arg Gln Ala Pro Gly Gln Gly Leu Glu Trp Met
            35                  40                  45

Gly Tyr Ile Asn Pro Tyr Thr Asp Val Thr Val Tyr Asn Glu Lys Phe
        50                  55                  60

Lys Gly Arg Val Thr Ile Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Phe Asp Gly Thr Phe Asp Tyr Ala Leu Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270
```

-continued

Glu Val Gln Phe Asn Trp Tyr Val Asp Gly Val Glu Val His Asn Ala
    275                 280                 285
Lys Thr Lys Pro Arg Glu Glu Gln Phe Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
            420                 425                 430
Leu His Asn His Tyr Thr Gln Lys Ser Leu Ser Leu Ser Leu Gly Lys
        435                 440                 445

<210> SEQ ID NO 57
<211> LENGTH: 448
<212> TYPE: PRT
<213> ORGANISM: Artificial Sequence
<220> FEATURE:
<223> OTHER INFORMATION: Synthetic: H0302-H2 heavy chain

<400> SEQUENCE: 57

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Ser Asp Phe
            20                  25                  30
Asn Ile His Trp Val Arg Gln Ala Pro Gly Gln Gly Leu Glu Trp Ile
        35                  40                  45
Gly Tyr Ile Asn Pro Tyr Thr Asp Val Thr Val Tyr Asn Glu Lys Phe
    50                  55                  60
Lys Gly Arg Ala Thr Leu Thr Ser Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Ser Tyr Phe Asp Gly Thr Phe Asp Tyr Ala Leu Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His

```
              195                 200                 205
Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 58
<211> LENGTH: 449
<212> TYPE: PRT
<213> ORGANISM: Artificial Sequence
<220> FEATURE:
<223> OTHER INFORMATION: Synthetic: H0311-H1 heavy chain

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Asn Gly Val Val Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ala Leu Tyr His Ser Asn Phe Gly Trp Tyr Phe Asp Ser Trp
            100                 105                 110

Gly Gln Gly Thr Leu Val Thr Val Ser Ser Ala Ser Thr Lys Gly Pro
        115                 120                 125
```

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 59
<211> LENGTH: 449
<212> TYPE: PRT
<213> ORGANISM: Artificial Sequence
<220> FEATURE:
<223> OTHER INFORMATION: Synthetic: H0311-H2 heavy chain

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Asp Tyr
            20                  25                  30

Asn Met His Trp Val Arg Gln Ala Pro Gly Gln Gly Leu Glu Trp Met

```
              35                  40                  45
Gly Glu Ile Asn Pro Asn Asn Gly Val Val Tyr Asn Gln Lys Phe
 50                  55                  60

Lys Gly Thr Thr Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Ala Leu Tyr His Ser Asn Phe Gly Trp Tyr Phe Asp Ser Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
        210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
        420                 425                 430

Ala Leu His Asn His Tyr Thr Gln Lys Ser Leu Ser Leu Ser Leu Gly
        435                 440                 445

Lys
```

```
<210> SEQ ID NO 60
<211> LENGTH: 218
<212> TYPE: PRT
<213> ORGANISM: Artificial Sequence
<220> FEATURE:
<223> OTHER INFORMATION: Synthetic: h0301-L0 light chain

<400> SEQUENCE: 60

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 61
<211> LENGTH: 218
<212> TYPE: PRT
<213> ORGANISM: Artificial Sequence
<220> FEATURE:
<223> OTHER INFORMATION: Synthetic: h0301-L1 light chain

<400> SEQUENCE: 61

Asn Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys Arg
```

```
                        100                 105                 110
Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 62
<211> LENGTH: 218
<212> TYPE: PRT
<213> ORGANISM: Artificial Sequence
<220> FEATURE:
<223> OTHER INFORMATION: Synthetic: H0302-L0 light chain

<400> SEQUENCE: 62

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Met Asn Trp Tyr Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 63
<211> LENGTH: 218
<212> TYPE: PRT
<213> ORGANISM: Artificial Sequence
```

<220> FEATURE:
<223> OTHER INFORMATION: Synthetic: H0302-L1 light chain

<400> SEQUENCE: 63

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Met Asn Trp Tyr Gln Gln Lys Pro Gly Gln Ala Pro
        35                  40                  45

Arg Leu Leu Ile Tyr Thr Ala Ser Asn Leu Glu Ser Gly Ile Pro Ala
50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 64
<211> LENGTH: 218
<212> TYPE: PRT
<213> ORGANISM: Artificial Sequence
<220> FEATURE:
<223> OTHER INFORMATION: Synthetic: H0302-L2 light chain

<400> SEQUENCE: 64

Glu Ile Val Val Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Met Asn Trp Phe Gln Gln Lys Pro Gly Gln Ala Pro
        35                  40                  45

Arg Leu Leu Ile Tyr Thr Ala Ser Asn Leu Glu Ser Gly Ile Pro Ala
50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 65
<211> LENGTH: 218
<212> TYPE: PRT
<213> ORGANISM: Artificial Sequence
<220> FEATURE:
<223> OTHER INFORMATION: Synthetic: H0311-L0 light chain

<400> SEQUENCE: 65

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
                20                  25                  30

Gly Asp Ser His Met Asn Trp Tyr Gln Gln Lys Pro Gly Gln Ala Pro
            35                  40                  45

Arg Leu Leu Ile Tyr Thr Ala Ser Asn Leu Glu Ser Gly Ile Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Gly Asn
                85                  90                  95

Glu Asp Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 66
<211> LENGTH: 218
<212> TYPE: PRT
<213> ORGANISM: Artificial Sequence
<220> FEATURE:
<223> OTHER INFORMATION: Synthetic: H0311-L1 light chain

<400> SEQUENCE: 66

```
Asp Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Ser His Met Asn Trp Tyr Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Gly Ala Asp Phe Thr Leu Thr Ile Ser
65              70                  75                  80

Ser Leu Glu Pro Glu Asp Phe Ala Val Tyr Tyr Cys Gln Gln Gly Asn
                85                  90                  95

Glu Asp Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 67
<211> LENGTH: 158
<212> TYPE: PRT
<213> ORGANISM: Homo sapiens
<220> FEATURE:
<221> NAME/KEY: misc_feature
<222> LOCATION: (1)..(158)
<223> OTHER INFORMATION: Human CSF1

<400> SEQUENCE: 67

Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Cys Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Thr
    50                  55                  60

Met Arg Phe Arg Asp Asn Thr Pro Asn Ala Ile Ala Ile Val Gln Leu
65              70                  75                  80

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu
            115                 120                 125

Asp Lys Asp Trp Asn Ile Phe Ser Lys Asn Cys Asn Asn Ser Phe Ala
```

```
                130                 135                 140
Glu Cys Ser Ser Gln Gly His Glu Arg Gln Ser Glu Gly Ser
145                 150                 155

<210> SEQ ID NO 68
<211> LENGTH: 222
<212> TYPE: PRT
<213> ORGANISM: Homo sapiens
<220> FEATURE:
<221> NAME/KEY: misc_feature
<222> LOCATION: (1)..(222)
<223> OTHER INFORMATION: Human IL34

<400> SEQUENCE: 68

Asn Glu Pro Leu Glu Met Trp Pro Leu Thr Gln Asn Glu Glu Cys Thr
1               5                   10                  15

Val Thr Gly Phe Leu Arg Asp Lys Leu Gln Tyr Arg Ser Arg Leu Gln
            20                  25                  30

Tyr Met Lys His Tyr Phe Pro Ile Asn Tyr Lys Ile Ser Val Pro Tyr
        35                  40                  45

Glu Gly Val Phe Arg Ile Ala Asn Val Thr Arg Leu Gln Arg Ala Gln
    50                  55                  60

Val Ser Glu Arg Glu Leu Arg Tyr Leu Trp Val Leu Val Ser Leu Ser
65                  70                  75                  80

Ala Thr Glu Ser Val Gln Asp Val Leu Leu Glu Gly His Pro Ser Trp
                85                  90                  95

Lys Tyr Leu Gln Glu Val Gln Thr Leu Leu Leu Asn Val Gln Gln Gly
            100                 105                 110

Leu Thr Asp Val Glu Val Ser Pro Lys Val Glu Ser Val Leu Ser Leu
        115                 120                 125

Leu Asn Ala Pro Gly Pro Asn Leu Lys Leu Val Arg Pro Lys Ala Leu
    130                 135                 140

Leu Asp Asn Cys Phe Arg Val Met Glu Leu Leu Tyr Cys Ser Cys Cys
145                 150                 155                 160

Lys Gln Ser Ser Val Leu Asn Trp Gln Asp Cys Glu Val Pro Ser Pro
                165                 170                 175

Gln Ser Cys Ser Pro Glu Pro Ser Leu Gln Tyr Ala Ala Thr Gln Leu
            180                 185                 190

Tyr Pro Pro Pro Pro Trp Ser Pro Ser Ser Pro Pro His Ser Thr Gly
        195                 200                 205

Ser Val Arg Pro Val Arg Ala Gln Gly Glu Gly Leu Leu Pro
    210                 215                 220

<210> SEQ ID NO 69
<211> LENGTH: 25
<212> TYPE: PRT
<213> ORGANISM: Homo sapiens
<220> FEATURE:
<221> NAME/KEY: misc_feature
<222> LOCATION: (1)..(25)
<223> OTHER INFORMATION: Human acceptor A FR1

<400> SEQUENCE: 69

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 70
<211> LENGTH: 14
```

```
<212> TYPE: PRT
<213> ORGANISM: Homo sapiens
<220> FEATURE:
<221> NAME/KEY: misc_feature
<222> LOCATION: (1)..(14)
<223> OTHER INFORMATION: Human acceptor A FR2

<400> SEQUENCE: 70

Trp Val Arg Gln Ala Pro Gly Gln Gly Leu Glu Trp Met Gly
1               5                   10

<210> SEQ ID NO 71
<211> LENGTH: 32
<212> TYPE: PRT
<213> ORGANISM: Homo sapiens
<220> FEATURE:
<221> NAME/KEY: misc_feature
<222> LOCATION: (1)..(32)
<223> OTHER INFORMATION: Human acceptor A FR3

<400> SEQUENCE: 71

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 72
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Human acceptor A FR4

<400> SEQUENCE: 72

Trp Gly Gln Gly Thr Leu Val Thr Val Ser Ser
1               5                   10

<210> SEQ ID NO 73
<211> LENGTH: 25
<212> TYPE: PRT
<213> ORGANISM: Homo sapiens
<220> FEATURE:
<221> NAME/KEY: misc_feature
<222> LOCATION: (1)..(25)
<223> OTHER INFORMATION: Human acceptor B FR1

<400> SEQUENCE: 73

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 74
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: Human acceptor B FR2

<400> SEQUENCE: 74

Trp Val Arg Gln Ala Pro Gly Gln Gly Leu Glu Trp Met Gly
1               5                   10

<210> SEQ ID NO 75
```

```
<211> LENGTH: 32
<212> TYPE: PRT
<213> ORGANISM: Homo sapiens
<220> FEATURE:
<221> NAME/KEY: misc_feature
<222> LOCATION: (1)..(32)
<223> OTHER INFORMATION: Human acceptor B FR3

<400> SEQUENCE: 75
```

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

```
<210> SEQ ID NO 76
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Human acceptor B FR4

<400> SEQUENCE: 76
```

Trp Gly Gln Gly Thr Leu Val Thr Val Ser Ser
1               5                   10

```
<210> SEQ ID NO 77
<211> LENGTH: 25
<212> TYPE: PRT
<213> ORGANISM: Homo sapiens
<220> FEATURE:
<221> NAME/KEY: misc_feature
<222> LOCATION: (1)..(25)
<223> OTHER INFORMATION: Human acceptor C FR1

<400> SEQUENCE: 77
```

Gln Val Gln Leu Val Gln Ser Gly Ala Glu Val Lys Lys Pro Gly Ser
1               5                   10                  15

Ser Val Lys Val Ser Cys Lys Ala Ser
            20                  25

```
<210> SEQ ID NO 78
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: Human acceptor C FR2

<400> SEQUENCE: 78
```

Trp Val Arg Gln Ala Pro Gly Gln Gly Leu Glu Trp Met Gly
1               5                   10

```
<210> SEQ ID NO 79
<211> LENGTH: 32
<212> TYPE: PRT
<213> ORGANISM: Homo sapiens
<220> FEATURE:
<221> NAME/KEY: misc_feature
<222> LOCATION: (1)..(32)
<223> OTHER INFORMATION: Human acceptor C FR3

<400> SEQUENCE: 79
```

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg

```
<210> SEQ ID NO 80
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Human acceptor C FR4

<400> SEQUENCE: 80

Trp Gly Gln Gly Thr Leu Val Thr Val Ser Ser
1               5                   10

<210> SEQ ID NO 81
<211> LENGTH: 23
<212> TYPE: PRT
<213> ORGANISM: Homo sapiens
<220> FEATURE:
<221> NAME/KEY: misc_feature
<222> LOCATION: (1)..(23)
<223> OTHER INFORMATION: Human acceptor D FR1

<400> SEQUENCE: 81

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 82
<211> LENGTH: 15
<212> TYPE: PRT
<213> ORGANISM: Homo sapiens
<220> FEATURE:
<221> NAME/KEY: misc_feature
<222> LOCATION: (1)..(15)
<223> OTHER INFORMATION: Human acceptor D FR2

<400> SEQUENCE: 82

Trp Tyr Gln Gln Lys Pro Gly Gln Ala Pro Arg Leu Leu Ile Tyr
1               5                   10                  15

<210> SEQ ID NO 83
<211> LENGTH: 32
<212> TYPE: PRT
<213> ORGANISM: Homo sapiens
<220> FEATURE:
<221> NAME/KEY: misc_feature
<222> LOCATION: (1)..(32)
<223> OTHER INFORMATION: Human acceptor D FR3

<400> SEQUENCE: 83

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 84
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Human acceptor D FR4

<400> SEQUENCE: 84
```

```
Phe Gly Gly Gly Thr Lys Val Glu Ile Lys
1               5                   10

<210> SEQ ID NO 85
<211> LENGTH: 23
<212> TYPE: PRT
<213> ORGANISM: Homo sapiens
<220> FEATURE:
<221> NAME/KEY: misc_feature
<222> LOCATION: (1)..(23)
<223> OTHER INFORMATION: Human acceptor E FR1

<400> SEQUENCE: 85

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 86
<211> LENGTH: 15
<212> TYPE: PRT
<213> ORGANISM: Homo sapiens
<220> FEATURE:
<221> NAME/KEY: misc_feature
<222> LOCATION: (1)..(15)
<223> OTHER INFORMATION: Human acceptor E FR2

<400> SEQUENCE: 86

Trp Tyr Gln Gln Lys Pro Gly Gln Ala Pro Arg Leu Leu Ile Tyr
1               5                   10                  15

<210> SEQ ID NO 87
<211> LENGTH: 32
<212> TYPE: PRT
<213> ORGANISM: Homo sapiens
<220> FEATURE:
<221> NAME/KEY: misc_feature
<222> LOCATION: (1)..(32)
<223> OTHER INFORMATION: Human acceptor E FR3

<400> SEQUENCE: 87

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 88
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Human acceptor E FR4

<400> SEQUENCE: 88

Phe Gly Gln Gly Thr Lys Val Glu Ile Lys
1               5                   10

<210> SEQ ID NO 89
<211> LENGTH: 23
<212> TYPE: PRT
<213> ORGANISM: Homo sapiens
<220> FEATURE:
<221> NAME/KEY: misc_feature
<222> LOCATION: (1)..(23)
<223> OTHER INFORMATION: Human acceptor F FR1

<400> SEQUENCE: 89
```

```
Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 90
<211> LENGTH: 15
<212> TYPE: PRT
<213> ORGANISM: Homo sapiens
<220> FEATURE:
<221> NAME/KEY: misc_feature
<222> LOCATION: (1)..(15)
<223> OTHER INFORMATION: Human acceptor F FR2

<400> SEQUENCE: 90

Trp Tyr Gln Gln Lys Pro Gly Gln Ala Pro Arg Leu Leu Ile Tyr
1               5                   10                  15

<210> SEQ ID NO 91
<211> LENGTH: 32
<212> TYPE: PRT
<213> ORGANISM: Homo sapiens
<220> FEATURE:
<221> NAME/KEY: misc_feature
<222> LOCATION: (1)..(32)
<223> OTHER INFORMATION: Human acceptor F FR3

<400> SEQUENCE: 91

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 92
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Human acceptor F FR4

<400> SEQUENCE: 92

Phe Gly Gln Gly Thr Lys Val Glu Ile Lys
1               5                   10

<210> SEQ ID NO 93
<211> LENGTH: 719
<212> TYPE: PRT
<213> ORGANISM: Mus musculus
<220> FEATURE:
<221> NAME/KEY: misc_feature
<222> LOCATION: (1)..(719)
<223> OTHER INFORMATION: mCSF1R ECD-Fc

<400> SEQUENCE: 93

Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
            20                  25                  30

Gly Pro Ile Ser Pro Tyr Trp Thr Leu Asp Pro Glu Ser Pro Gly Ser
        35                  40                  45

Thr Leu Thr Thr Arg Asn Ala Thr Phe Lys Asn Thr Gly Thr Tyr Arg
    50                  55                  60

Cys Thr Glu Leu Glu Asp Pro Met Ala Gly Ser Thr Thr Ile His Leu
```

```
                65                  70                  75                  80
Tyr Val Lys Asp Pro Ala His Ser Trp Asn Leu Leu Ala Gln Glu Val
                 85                  90                  95

Thr Val Val Glu Gly Gln Glu Ala Val Leu Pro Cys Leu Ile Thr Asp
                100                 105                 110

Pro Ala Leu Lys Asp Ser Val Ser Leu Met Arg Glu Gly Arg Gln
                115                 120                 125

Val Leu Arg Lys Thr Val Tyr Phe Phe Ser Pro Trp Arg Gly Phe Ile
130                 135                 140

Ile Arg Lys Ala Lys Val Leu Asp Ser Asn Thr Tyr Val Cys Lys Thr
145                 150                 155                 160

Met Val Asn Gly Arg Glu Ser Thr Ser Thr Gly Ile Trp Leu Lys Val
                165                 170                 175

Asn Arg Val His Pro Glu Pro Pro Gln Ile Lys Leu Glu Pro Ser Lys
                180                 185                 190

Leu Val Arg Ile Arg Gly Glu Ala Ala Gln Ile Val Cys Ser Ala Thr
                195                 200                 205

Asn Ala Glu Val Gly Phe Asn Val Ile Leu Lys Arg Gly Asp Thr Lys
210                 215                 220

Leu Glu Ile Pro Leu Asn Ser Asp Phe Gln Asp Asn Tyr Tyr Lys Lys
225                 230                 235                 240

Val Arg Ala Leu Ser Leu Asn Ala Val Asp Phe Gln Asp Ala Gly Ile
                245                 250                 255

Tyr Ser Cys Val Ala Ser Asn Asp Val Gly Thr Arg Thr Ala Thr Met
                260                 265                 270

Asn Phe Gln Val Val Glu Ser Ala Tyr Leu Asn Leu Thr Ser Glu Gln
                275                 280                 285

Ser Leu Leu Gln Glu Val Ser Val Gly Asp Ser Leu Ile Leu Thr Val
                290                 295                 300

His Ala Asp Ala Tyr Pro Ser Ile Gln His Tyr Asn Trp Thr Tyr Leu
305                 310                 315                 320

Gly Pro Phe Phe Glu Asp Gln Arg Lys Leu Glu Phe Ile Thr Gln Arg
                325                 330                 335

Ala Ile Tyr Arg Tyr Thr Phe Lys Leu Phe Leu Asn Arg Val Lys Ala
                340                 345                 350

Ser Glu Ala Gly Gln Tyr Phe Leu Met Ala Gln Asn Lys Ala Gly Trp
                355                 360                 365

Asn Asn Leu Thr Phe Glu Leu Thr Leu Arg Tyr Pro Pro Glu Val Ser
                370                 375                 380

Val Thr Trp Met Pro Val Asn Gly Ser Asp Val Leu Phe Cys Asp Val
385                 390                 395                 400

Ser Gly Tyr Pro Gln Pro Ser Val Thr Trp Met Glu Cys Arg Gly His
                405                 410                 415

Thr Asp Arg Cys Asp Glu Ala Gln Ala Leu Gln Val Trp Asn Asp Thr
                420                 425                 430

His Pro Glu Val Leu Ser Gln Lys Pro Phe Asp Lys Val Ile Ile Gln
                435                 440                 445

Ser Gln Leu Pro Ile Gly Thr Leu Lys His Asn Met Thr Tyr Phe Cys
450                 455                 460

Lys Thr His Asn Ser Val Gly Asn Ser Ser Gln Tyr Phe Arg Ala Val
465                 470                 475                 480

Ser Leu Gly Gln Ser Lys Gln Glu Pro Lys Ser Ser Asp Lys Thr His
                485                 490                 495
```

```
Thr Cys Pro Cys Pro Ala Pro Glu Leu Leu Gly Gly Pro Ser Val
            500                 505                 510

Phe Leu Phe Pro Pro Lys Pro Lys Asp Thr Leu Met Ile Ser Arg Thr
        515                 520                 525

Pro Glu Val Thr Cys Val Val Val Asp Val Ser His Glu Asp Pro Glu
    530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
        595                 600                 605

Ser Lys Ala Lys Gly Gln Pro Arg Glu Pro Gln Val Tyr Thr Leu Pro
    610                 615                 620

Pro Ser Arg Asp Glu Leu Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
            660                 665                 670

Asp Gly Ser Phe Phe Leu Tyr Ser Lys Leu Thr Val Asp Lys Ser Arg
        675                 680                 685

Trp Gln Gln Gly Asn Val Phe Ser Cys Ser Val Met His Glu Ala Leu
    690                 695                 700

His Asn His Tyr Thr Gln Lys Ser Leu Ser Leu Ser Pro Gly Lys
705                 710                 715

<210> SEQ ID NO 94
<211> LENGTH: 327
<212> TYPE: PRT
<213> ORGANISM: Artificial sequence
<220> FEATURE:
<223> OTHER INFORMATION: Synthetic: Human IgG4 S241P

<400> SEQUENCE: 94

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 95
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: Human Igk

<400> SEQUENCE: 95

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```